US008673904B2

(12) United States Patent
Bogyo et al.

(10) Patent No.: US 8,673,904 B2
(45) Date of Patent: Mar. 18, 2014

(54) EPOXIDE INHIBITORS OF CYSTEINE PROTEASES

(75) Inventors: Matthew S. Bogyo, Redwood City, CA (US); Amir M. Sadaghiani, Palo Alto, CA (US); Steven Verhelst, Palo Alto, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 226 days.

(21) Appl. No.: 11/762,735

(22) Filed: Jun. 13, 2007

(65) Prior Publication Data

US 2008/0176841 A1    Jul. 24, 2008

Related U.S. Application Data

(60) Provisional application No. 60/813,639, filed on Jun. 13, 2006.

(51) Int. Cl.
| | |
|---|---|
| C07D 303/48 | (2006.01) |
| C07D 401/12 | (2006.01) |
| A61K 31/5377 | (2006.01) |
| A61K 31/336 | (2006.01) |
| A61K 31/40 | (2006.01) |
| A61K 31/4427 | (2006.01) |
| A61K 31/4523 | (2006.01) |
| A61K 31/403 | (2006.01) |
| A61K 31/496 | (2006.01) |
| A61P 37/06 | (2006.01) |
| A61P 35/00 | (2006.01) |
| A61P 19/02 | (2006.01) |
| A61P 21/00 | (2006.01) |
| A61P 25/00 | (2006.01) |
| A61P 11/00 | (2006.01) |
| A61P 1/00 | (2006.01) |
| A61P 31/00 | (2006.01) |
| A61P 29/00 | (2006.01) |
| C07D 303/02 | (2006.01) |
| C07D 213/02 | (2006.01) |
| C07D 209/02 | (2006.01) |
| C07D 221/00 | (2006.01) |
| C07D 207/00 | (2006.01) |
| C07D 295/00 | (2006.01) |

(52) U.S. Cl.
USPC ............ 514/231.5; 514/254.1; 514/326; 514/336; 514/414; 514/422; 514/475; 544/147; 544/374; 546/207; 546/281.7; 549/548; 548/465; 548/517

(58) Field of Classification Search
None
See application file for complete search history.

(56) References Cited

U.S. PATENT DOCUMENTS

| | | | |
|---|---|---|---|
| 4,064,241 | A | 12/1977 | Ross et al. |
| 4,333,879 | A | 6/1982 | Tamai et al. |
| 4,418,075 | A | 11/1983 | Tamai et al. |
| 4,507,297 | A | 3/1985 | Masaki et al. |
| 4,596,803 | A | 6/1986 | Masaki et al. |
| 4,732,910 | A | 3/1988 | Yaginuma et al. |
| 5,281,717 | A | 1/1994 | Murata et al. |
| 5,556,853 | A | 9/1996 | Tsubotani et al. |
| 5,679,708 | A | 10/1997 | Tsubotani et al. |
| 5,883,121 | A | 3/1999 | Yamashita et al. |
| 6,110,967 | A | 8/2000 | Asao et al. |
| 2003/0212003 | A1 | 11/2003 | Lubbert et al. |
| 2004/0180981 | A1 | 9/2004 | Lopez et al. |
| 2006/0154325 | A1 | 7/2006 | Bogyo et al. |

FOREIGN PATENT DOCUMENTS

| | | |
|---|---|---|
| JP | 55-115878 A | 9/1980 |
| JP | 4-139182 A | 5/1992 |
| JP | 8-104683 A | 4/1996 |
| JP | 8-104684 A | 4/1996 |
| JP | 11263783 A | 9/1999 |
| WO | WO-97/21694 A1 | 6/1997 |
| WO | WO-98/47887 A1 | 10/1998 |
| WO | WO-02/38540 | 5/2002 |

OTHER PUBLICATIONS

Antiviral Medications, http://www.netdoctor.co.uk/medicines/effect/infections.shtml, 1998.*
Murata et al, caplus an 1999:620488.*
Hacks Chemical Dictionary, Fourth Edition, Julius Grant, 1972, p. 203.*
Buttle et al., caplus an 1992:81839.*
Sadaghiani et al., Chemistry&Biology, 14, 2007, 499-511.*
Tamai et al., caplus an 1981:157259.*
Immunosuppression, 2013, http://en.wikipedia.org/wiki/Immunosuppression.*
Helali et al, 2013, http://www.ncbi.nlm.nih.gov/pubmed/23957815.*
RA, 2013, http://www.mayoclinic.com/health/rheumatoid-arthritis/DS00020/DSECTION=treatments-and-drugs.*
AD, 2013, http://www.webmd.com/alzheimers/guide/treatment-overview.*
AD-prevention, 2013, http://www.nia.nih.gov/alzheimers/publication/preventing-alzheimers-disease.*
RA-prevention, 2013, http://www.medicinenet.com/rheumatoid_arthritis/page10.htm.*
Barrett et al., "L-trans-Epoxysuccinyl-leucylamido(4-guanidino)butane (E-64) and its analogues as inhibitors of cysteine proteinases including cathepsins B, H and L," Biochem. J., 201:189-198 (1982).

(Continued)

*Primary Examiner* — Sun Jae Loewe
(74) *Attorney, Agent, or Firm* — Ropes & Gray LLP

(57) ABSTRACT

Provided herein are novel epoxide inhibitors of cysteine proteases, compositions comprising the epoxide inhibitors, and packaged pharmaceuticals. Also provided are methods of inhibiting a papain-family cysteine protease and methods of treating or preventing a disease by administering a composition containing an epoxide inhibitor of the invention. The compositions may be administered in combination with another therapeutic agent.

3 Claims, 4 Drawing Sheets

(56) References Cited

OTHER PUBLICATIONS

Figure 1A:
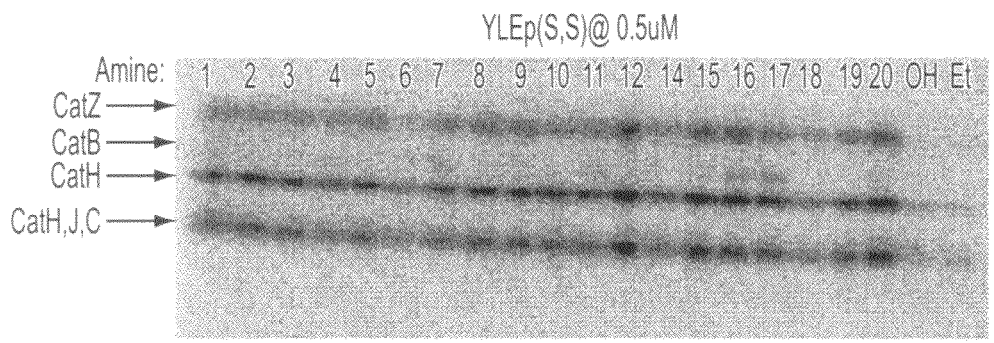

Buttle et al., "Inhibition of interleukin 1-stimulated cartilage proteoglycan degradation by a lipophilic inactivator of cysteine endopeptidases," Biochem. J., 281:175-177 (1992).

Giordano et al., "Iodo and diiodotyrosine epoxysuccinyl derivatives as selective inhibitors of cathepsin B," Eur. J. Med. Chem., 28:917-926 (1993).

Golde et al., "Processing of the Amyloid Protein Precursor to Potentially Amyloidogenic Derivatives," Science, 255:728-730 (1992).

Hashida et al., "Inhibitions by E-64 Derivatives of Rat Liver Cathepsin B and Cathepsin L In Vitro and In Vivo," J. Biochem., 88:1805-1811 (1980).

Iwata et al., "Macrophage Cathepsin L, a Factor in the Erosion of Subchondral Bone in Rheumatoid Arthritis," Arthritis & Rheumatism, 40:499-509 (1997).

Joyce et al., "Cathepsin cystein proteases are effectors of invasive growth and angiogenesis during multistage tumorigenesis," Cancer Cell, 5:443-453 (2004).

Katunuma et al., "Structure based development of novel specific inhibitors for cathepsin L and cathepsin S in vitro and in vivo," FEBS Letters, 458:6-10 (1999).

Korn et al., "A Convenient Synthesis of Optically Pure (2R,3R)-2,3-Epoxysuccinyl-Dipeptides," Tetrahedron, 50:8381-8392 (1994).

Meara et al., "Mechanistic Studies on the Inactivation of Papain by Epoxysuccinyl Inhibitors," J. Med. Chem., 39:3357-3366 (1996).

Munger et al., "Lysosomal processing of amyloid precursor protein to Aβ peptides: a distinct role for cathepsin S," Biochem. J., 311:299-305 (1995).

Schaschke et al., "Substrate/propeptide-derived endo-epoxysuccinyl peptides as highly potent and selective cathepsin B inhibitors," FEBS Letters, 421:80-82 (1998).

Schaschke et al., "E-64 Analogues as Inhibitors of Cathepsin B. On the Role of the Absolute Configuration of the Epoxysuccinyl Group," Bioorg. Med. Chem., 5:1789-1797 (1997).

Schirmeister "New Peptidic Cysteine Protease Inhibitors Derived from the Electrophilic α-Amino Acid Aziridine-2,3-dicarboxylic Acid," J. Med. Chem., 42:560-572 (1999).

Schirmeister et al., "Cysteine Protease Inhibitors Containing Small Rings," Mini Reviews in Medicinal Chemistry, 3:585-596 (2003).

Verhelst et al., "Solid-Phase Synthesis of Double-Headed Epoxysuccinyl Activity-Based Probes for Selective Targeting of Papain Family Cysteine Proteases," ChemBioChem, 6:824-827 (2005).

Yan et al., "Cathepsin B and human tumor progression," Biol. Chem., 379:113-123 (1998).

International Search Report for PCT/US2007/071145 dated May 5, 2008.

Supplementary European Search Report for European Application No. EP 07 86 3360 mailed Jul. 18, 2011.

Joiakim et al., "Superinduction of CYP1A1 in MCF10A Cultures by Cycloheximide, Anisomycin, and Puromycin: A Process Independent of Effects on Protein Translation and Unrelated to Suppression of Aryl Hydrocarbon Receptor Proteolysis by the Proteasome," Molecular Pharmacology, 66(4):936-947 (2004).

Roush et al., "A New Synthesis of Peptidyl Epoxysuccinates for Probing Cysteine Protease-Inhibitor P3/S3 Binding Interactions," Synthesis, 1999(S1):1500-1504 (1999).

Roush et al., "Design, Synthesis and Evaluation of D-Homophenylalanyl Epoxysuccinate Inhibitors of the Trypanosomal Cysteine Protease Cruzain," Tetrahedron, 56(50):9747-9762 (2000).

* cited by examiner

EPOXIDE INHIBITORS OF CYSTEINE PROTEASES

CROSS-REFERENCE TO RELATED APPLICATIONS

This application claims the benefit of U.S. Provisional Application No. 60/813,639, filed Jun. 13, 2006, the disclosure of which is incorporated herein by reference in its entirety.

FEDERALLY-SPONSORED RESEARCH OR DEVELOPMENT

This invention was made with Government support under contracts CA072006 and RR020843 awarded by the National Institutes of Health. The Government has certain rights in this invention.

BACKGROUND

Cysteine proteases and peptidases are defined by their use of an active-site cysteine as a nucleophile. Cysteine proteases are divided into clans (proteins which are evolutionary related), and further sub-divided into families, on the basis of the architecture of their catalytic dyad or triad. Barrett and Rawlings, *Biol. Chem.* 382:727-733, 2001. Members of the papain family of cysteine proteases display a wide variety of activities, including broad-range and narrow-range endopeptidases, aminopeptidases, dipeptidyl peptidases, and enzymes with both exo- and endo-peptidase activity. Members of this family are widespread and may be found in baculovirus, eubacteria, yeast, and practically all protozoa, plants, and mammals. The enzymes are typically lysosomal or secreted. They are often synthesized as inactive proenzymes with N-terminal propeptide regions that are proteolytically cleaved to activate the enzymatic activity.

Examples of enzymes belonging to the papain family of cysteine proteases include papain, bromelain, bleomycin hydrolase, and the cathepsins. There are at least 11 cathepsins encoded in the human genome and 19 in mouse, and each of these proteins displays different expression patterns, levels, and specificities. Turk et al., *Cancer Cell* 5:409-410, 2004. Several of these proteases are key players in normal physiological processes such as antigen presentation (Villadangos et al, *Immun. Rev.* 172:109-120, 1999), bone remodeling (Gelb et al., *Science* 273:1236-1238, 1996), and prohormone processing (Beinfeld, *Endocrine* 8:1-5, 1998). In addition, several of these proteases are involved in pathological processes such as rheumatoid arthritis (Iwata et al., *Arthritis and Rheumatism* 40:499-509, 1997), cancer invasion and metastasis (Yan et al., *Biol. Chem.* 379: 113-123, 1998; Joyce et al., *Cancer Cell* 5:443-453, 2004), and Alzheimer's disease (Golde et al., *Science* 255:728-730, 1992; Munger et al., *Biochem. J.* 311:299-305, 1995).

The enzymatic mechanism used by the papain family of cysteine proteases has been well studied and is highly conserved. Thus, electrophilic substrate analogs that are only reactive in the context of this conserved active site can be used as general probes of function. A wide range of electrophiles have been developed as mechanism-based, cysteine protease inhibitors, including diazomethyl ketones (Shaw, *Meth. Enzymol.* 244:649-656, 1986), fluoromethyl ketones (Shaw et al. *Biomedica Biochimica Acta* 45:1397-1403, 1986), acyloxymethyl ketones (Pliura et al., *Biochem. J.* 288:759-762, 1992), O-acylhydroxylamines (Brömme et al., *Biochem. J.* 263:861-866, 1989), and vinyl sulfones (Palmer et al, *J. Med. Chem.* 38:3193-3196, 1995). These inhibitors typically consist of a peptide specificity determinant attached to an electrophile that irreversibly alkylates the enzyme when bound in close proximity to an attacking nucleophile.

A naturally-occurring epoxysuccinyl peptide capable of irreversibly inhibiting cysteine proteases, including cathepsins B, H, and L, was isolated from *Aspergillus japonicus* in the late 1970s. Barrett et al., *Biochem. J.* 201:189-198, 1982.

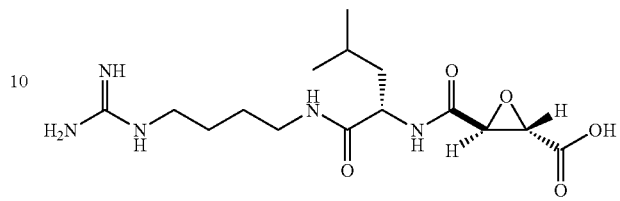

L-trans-epoxysuccinyl-leucylamido-(4-guanidino) butane ("E-64")

Although E-64 is a powerful inhibitor of various cysteine proteases, its selectivity is limited. A number of additional epoxysuccinyl peptide inhibitors have subsequently been reported and at least partly characterized. See, e.g., U.S. Pat. Nos. 4,333,879; 4,418,075; 4,507,297; 4,596,803; 4,732,910; 5,556,853; 5,679,708; 5,883,121; 6,110,967; U.S. Patent Application Publication No. 2003/212003; PCT International Publication No. WO02/38540. See also Hashida et al., *J. Biochem.* (Tokyo) 88:1805-1811, 1980; Buttle et al., *Biochem. J.* 281:175-177, 1992; Giordano et al., *Eur. J. Med. Chem.* 28:917-926, 1993; Korn et al., *Tetrahedron* 50:8381-8392, 1994; Meara and Rich, *J. Med. Chem.* 39:3357-3366, 1996; Schaschke et al., *Bioorg. & Med. Chem.* 5:1789-1797, 1997; Schaschke et al, *FEBS Lett.* 421:80-82, 1998; Katunuma et al., *FEBS Lett.* 458:6-10, 1999; Schirmeister, *J. Med. Chem.* 42:560-572, 1999, Bogyo et al., *Chem. Biol.* 7:27-38, 2000; Greenbaum et al., *Chem. Biol.* 9:1085-1094, 2002; Schirmeister and Klockow, *Mini Reviews Med. Chem.* 3:585-596, 2003.

Due to the importance of the cysteine proteases, and in particular the papain family of cysteine proteases, in pathological processes, there is great interest in developing additional inhibitors with defined specificities against these enzymes. Such inhibitors can help to identify target enzymes in cells, particularly where the cells are associated with particular indications, and can provide new drug candidates. There is thus a need for additional inhibitors of cysteine proteases and novel methods of inhibiting those enzymes.

SUMMARY OF THE INVENTION

The present invention addresses these problems by providing novel epoxide inhibitors of cysteine proteases, compositions, packaged pharmaceuticals, and methods of use thereof. In one aspect, the invention provides compounds represented by structural formula (I):

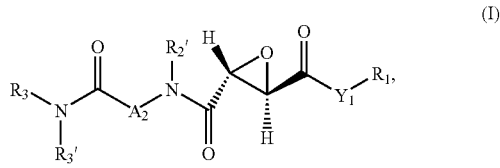

(I)

or a pharmaceutically acceptable derivative or prodrug thereof, wherein:

$Y_1$ is O or N—$R_1'$;

$A_2$ is —C($R_2$)($R_2''$)—, arylene, cycloalkylene, heteroarylene, or heterocycloalkylene, optionally substituted with 1-3 J groups;

R₂ and R₂" are independently H, alkyl, alkenyl, alkynyl, aryl, aralkyl, aralkenyl, cycloalkyl, cycloalkenyl, heterocyclyl, heterocyclylalkyl, heterocyclylalkenyl, heteroaryl, heteroaralkyl, carboxyalkyl, or carboxamidoalkyl, R₂ and R₂" taken together with the C atom to which they are attached complete a cyclic structure having from 4 to 8 atoms in the ring, or R₂ and R₂" taken together with the C atom to which they are attached form an alkene; wherein R₂ and R₂" are independently optionally substituted with 1-3 J groups and wherein any alkyl carbon atom may be replaced by a heteroatom;

R₁, R₁', R₂', R₃, and R₃' are independently H, alkyl, alkenyl, alkynyl, aryl, aralkyl, aralkenyl, cycloalkyl, cycloalkenyl, heterocyclyl, heterocyclylalkyl, heterocyclylalkenyl, heteroaryl, heteroaralkyl, carboxyalkyl, or carboxamidoalkyl, and are optionally substituted with 1-3 J groups, wherein any alkyl carbon atom may be replaced by a heteroatom and wherein R₃ and R₃' taken together with the N atom to which they are attached complete a cyclic structure having from 4 to 8 atoms in the ring;

J is alkyl, aryl, aralkyl, alkoxy, aryloxy, aralkoxy, cycloalkyl, cycloalkoxy, heterocyclyl, heterocyclyloxy, heterocyclylalkyl, heteroaryl, heteroaralkyl, keto, hydroxy, thio, amino, alkylamino, alkanoylamino, aroylamino, aralkanoylamino, carboxy, carbonate, carbamate, guanidinyl, urea, halo, cyano, nitro, formyl, acyl, phosphoryl, sulfonyl, or sulfonamido and is optionally substituted with 1-3 $J^1$ groups;

$J^1$ is alkyl, aryl, aralkyl, alkoxy, aryloxy, heterocyclyl, heterocyclyloxy, keto, hydroxy, thio, amino, alkanoylamino, aroylamino, carboxy, carbonate, carbamate, guanidinyl, urea, halo, cyano, nitro, formyl, acyl, phosphoryl, sulfonyl, or sulfonamido;

provided that when A₂ is —C(R₂)(R₂")—, R₂ is a naturally-occurring amino acid side chain, and R₂" is H, then —Y₁—R₁ is not —OH, —OCH₃, or —OCH₂CH₃;

when A₂ is —C(R₂)(R₂")—, R₂ is —CH₂—CH(CH₃)₂, and R₂" is H, then R₃ is not —CH₂—CH₂—CH₂—NH—C(=NH)—NH₂ or —C(H)(NH₂)—CH₂—CH₂—CH₂—NH—C(=NH)—NH₂, and R₃ and R₃' together with the N atom to which they are attached do not form a 5-membered ring substituted with carboxy;

when A₂ is —C(R₂)(R₂")—, R₂ is —CH₂-Phenyl, and R₂" is H, then R₃ and R₃' are not both —CH₃; and when A₂ is —C(R₂)(R₂")—, R₂ is —CH₂—CH₂—CH₂—CH₂—CH₂—NH₂, and R₂" is H, then R₃ is not naphthyl.

The invention also provides compounds represented by structural formula (II):

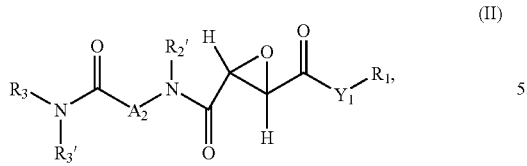

(II)

or a pharmaceutically acceptable derivative or prodrug thereof, wherein:

Y₁ is O or N—H;

A₂ is —C(R₂)(R₂")—, arylene, cycloalkylene, heteroarylene, or heterocycloalkylene, optionally substituted with 1-3 J groups;

R₂ and R₂" are independently H, alkyl, alkenyl, alkynyl, aryl, aralkyl, aralkenyl, cycloalkyl, cycloalkenyl, heterocyclyl, heterocyclylalkyl, heterocyclylalkenyl, heteroaryl, heteroaralkyl, carboxyalkyl, or carboxamidoalkyl, R₂ and R₂" taken together with the C atom to which they are attached complete a cyclic structure having from 4 to 8 atoms in the ring, or R₂ and R₂" taken together with the C atom to which they are attached form an alkene; wherein R₂ and R₂" are independently optionally substituted with 1-3 J groups and wherein any alkyl carbon atom may be replaced by a heteroatom;

R₁ is selected from the group consisting of:

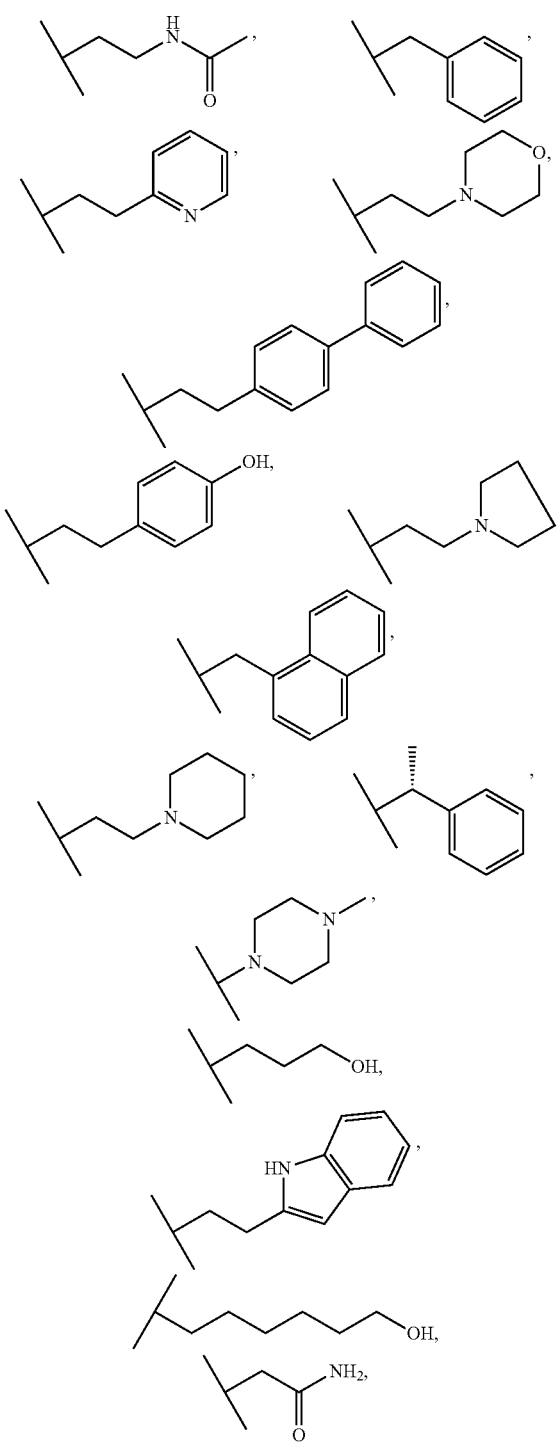

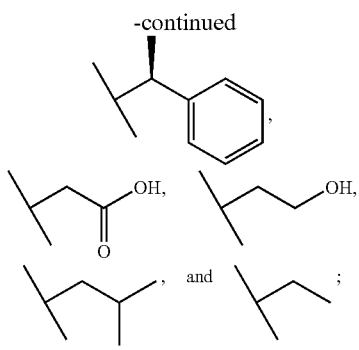

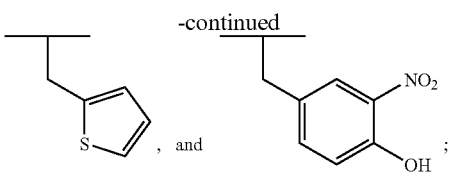

$R_2'$, $R_3$, and $R_3'$ are independently H, alkyl, alkenyl, alkynyl, aryl, aralkyl, aralkenyl, cycloalkyl, cycloalkenyl, heterocyclyl, heterocyclylalkyl, heterocyclylalkenyl, heteroaryl, heteroaralkyl, carboxyalkyl, or carboxamidoalkyl, and are optionally substituted with 1-3 J groups, wherein any alkyl carbon atom may be replaced by a heteroatom;

J is alkyl, aryl, aralkyl, alkoxy, aryloxy, aralkoxy, cycloalkyl, cycloalkoxy, heterocyclyl, heterocyclyloxy, heterocyclylalkyl, heteroaryl, heteroaralkyl, keto, hydroxy, thio, amino, alkylamino, alkanoylamino, aroylamino, aralkanoylamino, carboxy, carbonate, carbamate, guanidinyl, urea, halo, cyano, nitro, formyl, acyl, phosphoryl, sulfonyl, or sulfonamido and is optionally substituted with 1-3 $J^1$ groups;

$J^1$ is alkyl, aryl, aralkyl, alkoxy, aryloxy, heterocyclyl, heterocyclyloxy, keto, hydroxy, thio, amino, alkanoylamino, aroylamino, carboxy, carbonate, carbamate, guanidinyl, urea, halo, cyano, nitro, formyl, acyl, phosphoryl, sulfonyl, or sulfonamido;

provided that when $Y_1$ is O, $R_1$ is not

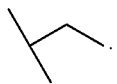

In other embodiments, the invention provides compounds represented by structural formula (II):

$$\text{(II)}$$

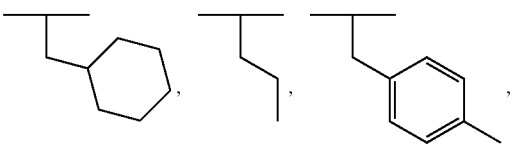

or a pharmaceutically acceptable derivative or prodrug thereof, wherein:

$Y_1$ is O or N—$R_1'$;

$A_2$ is —C($R_2$)($R_2''$)—, arylene, cycloalkylene, heteroarylene, or heterocycloalkylene, optionally substituted with 1-3 J groups;

$R_2''$ is H;

$R_2$ is selected from the group consisting of:

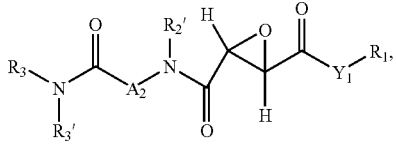

$R_1$, $R_1'$, $R_2'$, $R_3$, and $R_3'$ are independently H, alkyl, alkenyl, alkynyl, aryl, aralkyl, aralkenyl, cycloalkyl, cycloalkenyl, heterocyclyl, heterocyclylalkyl, heterocyclylalkenyl, heteroaryl, heteroaralkyl, carboxyalkyl, or carboxamidoalkyl, and are optionally substituted with 1-3 J groups, wherein any alkyl carbon atom may be replaced by a heteroatom and wherein $R_3$ and $R_3'$ taken together with the N atom to which they are attached complete a cyclic structure having from 4 to 8 atoms in the ring;

J is alkyl, aryl, aralkyl, alkoxy, aryloxy, aralkoxy, cycloalkyl, cycloalkoxy, heterocyclyl, heterocyclyloxy, heterocyclylalkyl, heteroaryl, heteroaralkyl, keto, hydroxy, thio, amino, alkylamino, alkanoylamino, aroylamino, aralkanoylamino, carboxy, carbonate, carbamate, guanidinyl, urea, halo, cyano, nitro, formyl, acyl, phosphoryl, sulfonyl, or sulfonamido and is optionally substituted with 1-3 $J^1$ groups;

$J^1$ is alkyl, aryl, aralkyl, alkoxy, aryloxy, heterocyclyl, heterocyclyloxy, keto, hydroxy, thio, amino, alkanoylamino, aroylamino, carboxy, carbonate, carbamate, guanidinyl, urea, halo, cyano, nitro, formyl, acyl, phosphoryl, sulfonyl, or sulfonamido;

In still other embodiments, the invention provides compounds represented by structural formula (II):

$$\text{(II)}$$

or a pharmaceutically acceptable derivative or prodrug thereof, wherein:

$Y_1$ is O or N—$R_1'$;

$A_2$ is —C($R_2$)($R_2''$)—, arylene, cycloalkylene, heteroarylene, or heterocycloalkylene, optionally substituted with 1-3 J groups;

$R_2$ and $R_2''$ are independently H, alkyl, alkenyl, alkynyl, aryl, aralkyl, aralkenyl, cycloalkyl, cycloalkenyl, heterocyclyl, heterocyclylalkyl, heterocyclylalkenyl, heteroaryl, heteroaralkyl, carboxyalkyl, or carboxamidoalkyl, $R_2$ and $R_2''$ taken together with the C atom to which they are attached complete a cyclic structure having from 4 to 8 atoms in the ring, or $R_2$ and $R_2''$ taken together with the C atom to which they are attached form an alkene; wherein $R_2$ and $R_2''$ are independently optionally substituted with 1-3 J groups and wherein any alkyl carbon atom may be replaced by a heteroatom;

R₃ is selected from the group consisting of:

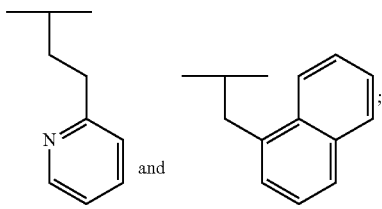

and

R₃' is H;
R₁, R₁', and R₂' are independently H, alkyl, alkenyl, alkynyl, aryl, aralkyl, aralkenyl, cycloalkyl, cycloalkenyl, heterocyclyl, heterocyclylalkyl, heterocyclylalkenyl, heteroaryl, heteroaralkyl, carboxyalkyl, or carboxamidoalkyl, and are optionally substituted with 1-3 J groups, wherein any alkyl carbon atom may be replaced by a heteroatom;
J is alkyl, aryl, aralkyl, alkoxy, aryloxy, aralkoxy, cycloalkyl, cycloalkoxy, heterocyclyl, heterocyclyloxy, heterocyclylalkyl, heteroaryl, heteroaralkyl, keto, hydroxy, thio, amino, alkylamino, alkanoylamino, aroylamino, aralkanoylamino, carboxy, carbonate, carbamate, guanidinyl, urea, halo, cyano, nitro, formyl, acyl, phosphoryl, sulfonyl, or sulfonamido and is optionally substituted with 1-3 J¹ groups;
J¹ is alkyl, aryl, aralkyl, alkoxy, aryloxy, heterocyclyl, heterocyclyloxy, keto, hydroxy, thio, amino, alkanoylamino, aroylamino, carboxy, carbonate, carbamate, guanidinyl, urea, halo, cyano, nitro, formyl, acyl, phosphoryl, sulfonyl, or sulfonamido;

In still other embodiments, the invention provides, compounds represented by structural formula (II):

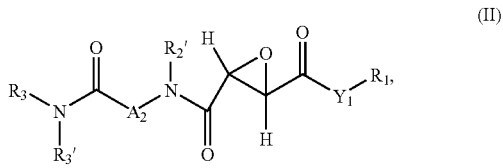

(II)

or a pharmaceutically acceptable derivative or prodrug thereof, wherein:
Y₁ is O or N—R₁';
A₂ is —C(R₂)(R₂")—, arylene, cycloalkylene, heteroarylene, or heterocycloalkylene, optionally substituted with 1-3 J groups;
R₂ and R₂" are independently H, alkyl, alkenyl, alkynyl, aryl, aralkyl, aralkenyl, cycloalkyl, cycloalkenyl, heterocyclyl, heterocyclylalkyl, heterocyclylalkenyl, heteroaryl, heteroaralkyl, carboxyalkyl, or carboxamidoalkyl, R₂ and R₂" taken together with the C atom to which they are attached complete a cyclic structure having from 4 to 8 atoms in the ring, or R₂ and R₂" taken together with the C atom to which they are attached form an alkene; wherein R₂ and R₂" are independently optionally substituted with 1-3 J groups and wherein any alkyl carbon atom may be replaced by a heteroatom;
R₁, R₁', R₃, and R₃' are independently H, alkyl, alkenyl, alkynyl, aryl, aralkyl, aralkenyl, cycloalkyl, cycloalkenyl, heterocyclyl, heterocyclylalkyl, heterocyclylalkenyl, heteroaryl, heteroaralkyl, carboxyalkyl, or carboxamidoalkyl, and are optionally substituted with 1-3 J groups, wherein any alkyl carbon atom may be replaced by a heteroatom and wherein R₃ and R₃' taken together with the N atom to which they are attached complete a cyclic structure having from 4 to 8 atoms in the ring;
R₂' is alkyl, alkenyl, alkynyl, aryl, aralkyl, aralkenyl, cycloalkyl, cycloalkenyl, heterocyclyl, heterocyclylalkyl, heterocyclylalkenyl, heteroaryl, heteroaralkyl, carboxyalkyl, or carboxamidoalkyl, and are optionally substituted with 1-3 J groups, wherein any alkyl carbon atom may be replaced by a heteroatom;
J is alkyl, aryl, aralkyl, alkoxy, aryloxy, aralkoxy, cycloalkyl, cycloalkoxy, heterocyclyl, heterocyclyloxy, heterocyclylalkyl, heteroaryl, heteroaralkyl, keto, hydroxy, thio, amino, alkylamino, alkanoylamino, aroylamino, aralkanoylamino, carboxy, carbonate, carbamate, guanidinyl, urea, halo, cyano, nitro, formyl, acyl, phosphoryl, sulfonyl, or sulfonamido and is optionally substituted with 1-3 J¹ groups;
J¹ is alkyl, aryl, aralkyl, alkoxy, aryloxy, heterocyclyl, heterocyclyloxy, keto, hydroxy, thio, amino, alkanoylamino, aroylamino, carboxy, carbonate, carbamate, guanidinyl, urea, halo, cyano, nitro, formyl, acyl, phosphoryl, sulfonyl, or sulfonamide.

The invention also encompasses pharmaceutical compositions comprising a compound of the invention and a pharmaceutically acceptable carrier.

In another aspect, the invention provides packaged pharmaceuticals comprising the pharmaceutical composition of the invention and instructions for using the composition in a mammalian host.

The invention also encompasses methods for inhibiting a papain-family cysteine protease in a mammalian host, comprising administering to the mammalian host in need thereof a pharmaceutical composition of the invention.

In another aspect, methods are provided for treating or preventing a disease associated with a papain-family cysteine protease in a mammalian host, comprising administering to the mammalian host in need thereof a therapeutically-effective amount of a pharmaceutical composition of the invention.

In yet another aspect, the invention provides methods for suppressing the immune system in a mammalian host, comprising administering to the mammalian host in need thereof a pharmaceutical composition of the invention.

In still yet another aspect, the invention provides methods for treating or preventing an immune-related disease, an inflammatory disease, a tissue remodeling disease, cancer, or an infectious disease in a mammalian host, comprising administering to a mammalian host in need thereof a therapeutically-effective amount of a pharmaceutical composition of the invention.

In certain embodiments, the immune-related disease is an allergic disease, asthma, organ/tissue rejection, or an autoimmune disease. In more specific embodiments, the autoimmune disease is diabetes, lupus, rheumatoid arthritis, psoriasis, multiple sclerosis, or inflammatory bowel disease. In even more specific embodiments, the inflammatory bowel disease is ulcerative colitis or Crohn's disease.

In certain embodiments, the inflammatory disease is psoriasis, a lung disease, a progressive neurodegenerative disorder, or atherosclerosis. In more specific embodiments, the lung disease is chronic obstructive pulmonary disease, bronchitis, emphysema, acute respiratory syndrome, cystic fibrosis, or asthma. In other more specific embodiments, the progressive neurodegenerative disorder is Alzheimer's disease.

In certain embodiments, the tissue remodeling disease is a muscle-wasting disease, osteoporosis, Paget's disease, bone fractures, abnormally increased bone turnover, an arthritis, perprosthetic osteolysis, osteogenesis imperfecta, metastatic bone disease, or hypercalcemia of malignancy. In more specific embodiments, the muscle-wasting disease is muscular dystrophy or cachexia. In other more specific embodiments, the arthritis is osteoarthritis or rheumatoid arthritis.

In some embodiments, the disease is cancer. In specific embodiments, the cancer is pancreatic adenocarcinoma or breast cancer. In some embodiments, the method further comprises administration of a chemotherapeutic agent.

In some embodiments, the infectious disease is a viral infection or a parasitic infection. In specific embodiments, the viral infection is a coronavirus infection. In other specific embodiments, the parasitic infection is a plasmodial infection, a trypanosomal infection, a leishmanial infection, a pneumocystis infection, a toxoplasma infection, an entamoeba infection, or a giardial infection. In even more specific embodiments, the infection is a *P. falciparum* infection, a *P. vivax* infection, a *P. malariae* infection, a *P. ovale* infection, a *T. cruzi* infection, a *T. brucei* infection, a *L. amazonensis* infection, a *L. donovani* infection, a *L. infantum* infection, a *L. mexicana* infection, a *Pneumocystis carinii* infection, a *Toxoplasma gondii* infection, an *Entamoeba histolytica* infection, an *Entamoeba invadens* infection, or a *Giardia lamblia* infection.

The details of various aspects of the invention are set forth in the accompanying drawings and the description below. Other features, objects, and advantages of the invention will be apparent from the description and claims.

LISTING OF DRAWINGS

Figure 1B:
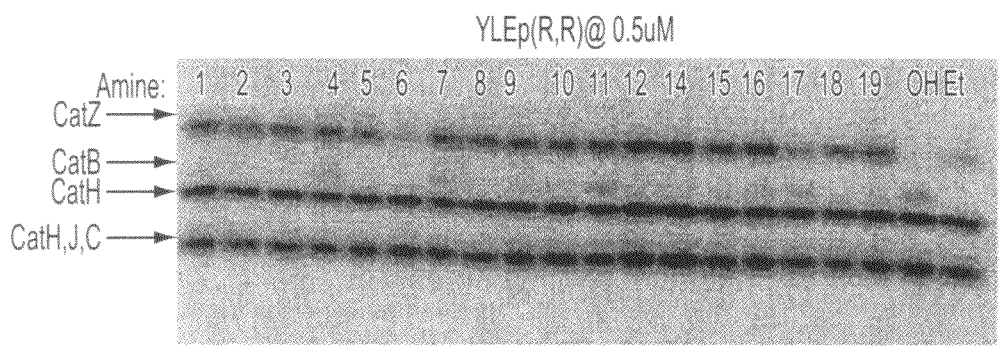
Figure 1C:
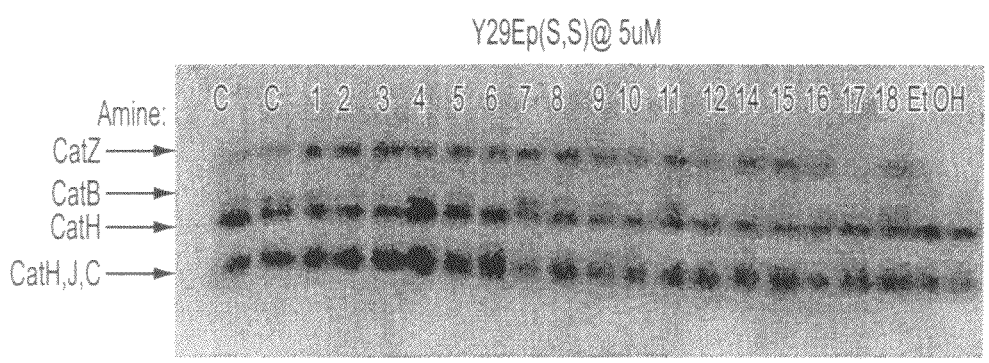
Figure 2A:
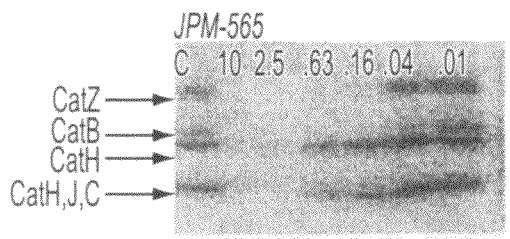
Figure 2B:
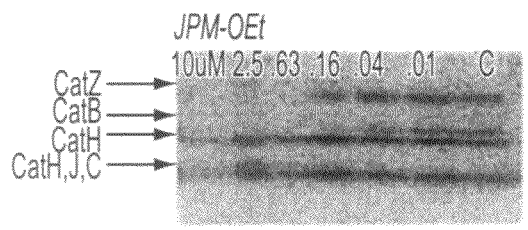
Figure 2C:
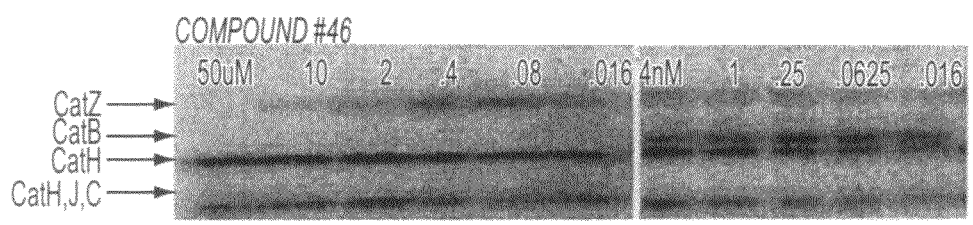
Figure 2D:
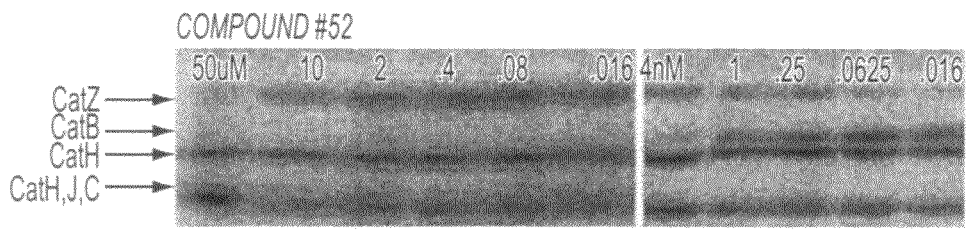

FIG. 1. Profiling of libraries in crude rat liver extracts.

FIG. 2. Competition in rat liver homogenates for two cathepsin B-specific compounds.

Figure 3A:
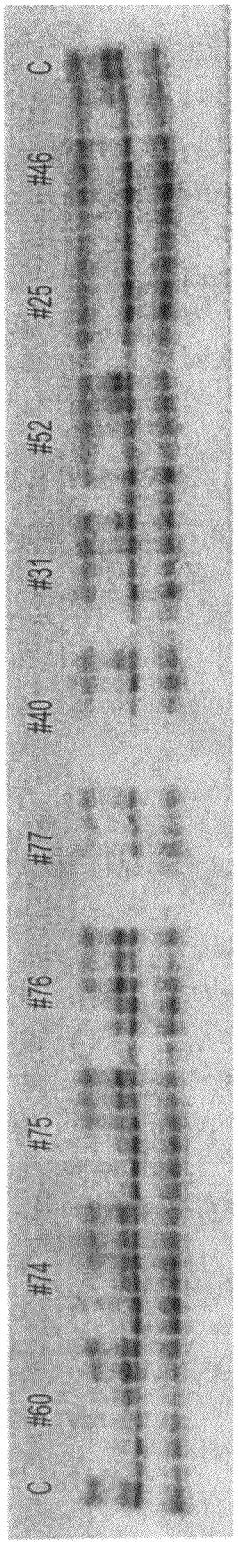
Figure 3B:
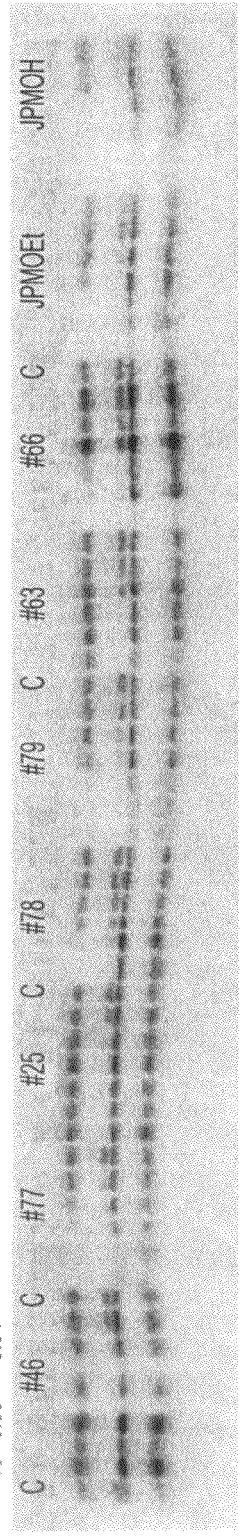
Figure 3C:
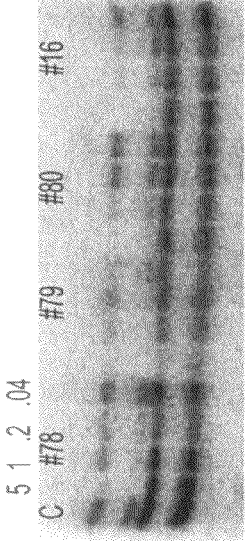

FIG. 3. Competition assays in rat liver homogenates with various inhibitors. The indicated compounds were assayed at 25, 5, 1, 0.2 0.04, and 0.008 µM (panel A); 10, 2.5, 0.63, 0.04, and 0.01 µM (panel B); and 5, 1, 0.2, and 0.04 µM (panel C).

Figure 4A:
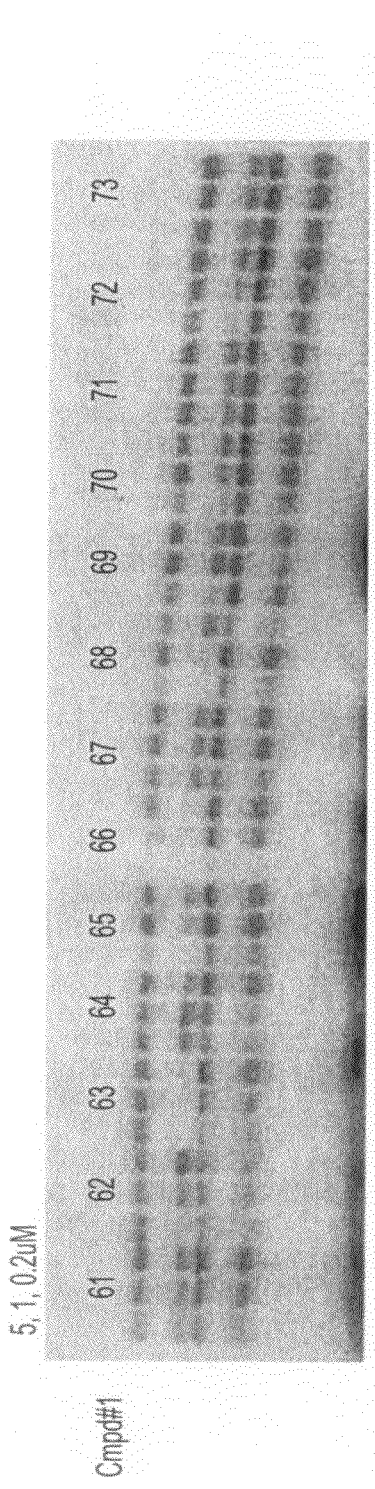
Figure 4B:
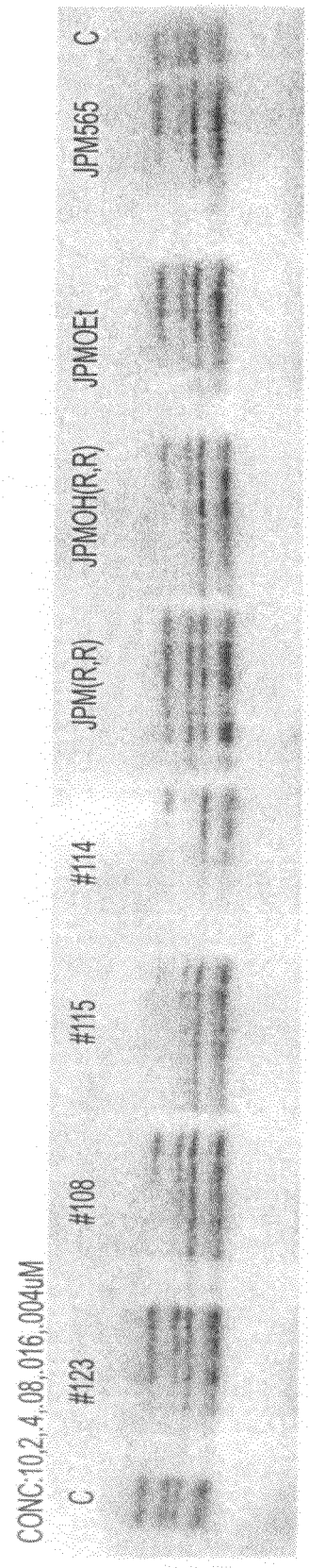

FIG. 4. Competition assays in rat liver homogenates with various inhibitors. The indicated compounds were assayed at 5, 1, and 0.2 µM (panel A); and 10, 2, 0.4, 0.08, 0.016, and 0.004 µM (panel B).

DETAILED DESCRIPTION OF THE INVENTION

The present invention relates to compounds that inhibit cysteine protease activity. Among the compounds of the present invention are peptidyl epoxide inhibitor compounds. The invention also relates to pharmaceutical compositions comprising an epoxide inhibitor compound of the invention and a pharmaceutically acceptable carrier or diluent and to packaged pharmaceuticals. The invention also relates to methods for inhibiting a papain-family cathepsin and to methods for treating or preventing disease.

Before further description of the invention, certain terms employed in the specification, examples and appended claims are, for convenience, collected here.

The term "alkoxy" refers to an alkyl group, in certain specific embodiments, a lower alkyl group, having an oxygen attached thereto. Representative alkoxy groups include methoxy, ethoxy, propoxy, tert-butoxy, and the like.

The term "alkenyl", as used herein, refers to an aliphatic group containing at least one double bond and is intended to include both "unsubstituted alkenyls" and "substituted alkenyls", the latter of which refers to alkenyl moieties having substituents replacing a hydrogen on one or more carbons of the alkenyl group. Such substituents may occur on one or more carbons that are included or not included in one or more double bonds. Moreover, such substituents include all those contemplated for alkyl groups, as discussed below, except where stability is prohibitive. For example, substitution of alkenyl groups by one or more alkyl, cycloalkyl, heterocyclyl, aryl, or heteroaryl groups is contemplated.

The term "alkyl" refers to the radical of saturated aliphatic groups, including straight-chain alkyl groups, branched-chain alkyl groups, cycloalkyl (alicyclic) groups, alkyl-substituted cycloalkyl groups, and cycloalkyl-substituted alkyl groups. In some embodiments, a straight chain or branched chain alkyl has 30 or fewer carbon atoms in its backbone (e.g., $C_1$-$C_{30}$ for straight chains, $C_3$-$C_{30}$ for branched chains), and more specifically 20 or fewer. In specific embodiments, the alkyl group contains 10 or fewer carbon atoms. In even more specific embodiments, the alkyl group contains 6 or fewer carbon atoms. Likewise, some cycloalkyls have from 3-10 carbon atoms in their ring structure, and more specifically have 5, 6 or 7 carbons in the ring structure.

Moreover, the term "alkyl" (or "lower alkyl") as used throughout the specification, examples, and claims is intended to include both "unsubstituted alkyls" and "substituted alkyls", the latter of which refers to alkyl moieties having substituents replacing a hydrogen on one or more carbons of the hydrocarbon backbone. Such substituents can include, for example, a halo, a hydroxyl, a carbonyl (such as a keto, a carboxy, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a thio, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —$CF_3$, —CN and the like. Exemplary substituted alkyls are described below. Cycloalkyls can be further substituted with alkyls, alkenyls, alkoxys, alkylthios, aminoalkyls, carbonyl-substituted alkyls, —$CF_3$, —CN, and the like.

The term "$C_{x-y}$" when used in conjunction with a chemical moiety, such as, acyl, acyloxy, alkyl, alkenyl, alkynyl, or alkoxy is meant to include groups that contain from x to y carbons in the chain. For example, the term "$C_{x-y}$alkyl" refers to substituted or unsubstituted saturated hydrocarbon groups, including straight-chain alkyl and branched-chain alkyl groups that contain from x to y carbons in the chain, including haloalkyl groups such as trifluoromethyl and 2,2,2-trifluoroethyl, etc. "Co-alkyl" indicates a hydrogen where the group is in a terminal position, or is a bond if internal. The terms "$C_{2-y}$-alkenyl" and "$C_{2-y}$-alkynyl" refer to substituted or unsubstituted unsaturated aliphatic groups analogous in length and possible substitution to the alkyls described above, but that contain at least one double or triple bond, respectively.

The term "alkylamino", as used herein, refers to an amino group substituted with at least one alkyl group.

The term "alkylthio", as used herein, refers to a thiol group substituted with an alkyl group and may be represented by the general formula alkyl-S—.

The term "alkynyl", as used herein, refers to an aliphatic group containing at least one triple bond and is intended to include both "unsubstituted alkynyls" and "substituted alkynyls", the latter of which refers to alkynyl moieties having substituents replacing a hydrogen on one or more carbons of the alkynyl group. Such substituents may occur on one or more carbons that are included or not included in one or more triple bonds. Moreover, such substituents include all those contemplated for alkyl groups, as discussed above, except where stability is prohibitive. For example, substitution of alkynyl groups by one or more alkyl, cycloalkyl, heterocyclyl, aryl, or heteroaryl groups is contemplated.

The term "amide", as used herein, refers to a group

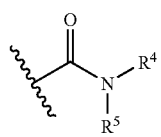

wherein $R^4$ and $R^5$ each independently represent a hydrogen or hydrocarbyl group, or $R^4$ and $R^5$ taken together with the N atom to which they are attached complete a heterocycle having from 4 to 8 atoms in the ring structure.

The terms "amine" and "amino" are art-recognized and refer to both unsubstituted and substituted amines and salts thereof, e.g., a moiety that can be represented by

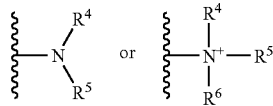

wherein $R^4$, $R^5$, and $R^6$ each independently represent a hydrogen or a hydrocarbyl group, or $R^4$ and $R^5$ taken together with the N atom to which they are attached complete a heterocycle having from 4 to 8 atoms in the ring structure.

The term "aminoalkyl", as used herein, refers to an alkyl group substituted with an amino group.

The term "aralkyl", as used herein, refers to an alkyl group substituted with an aryl group.

The term "aryl" as used herein includes substituted or unsubstituted single-ring aromatic groups in which each atom of the ring is carbon. In certain embodiments, the ring is a 5- to 7-membered ring, and in more specific embodiments is a 6-membered ring. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Aryl groups include benzene, naphthalene, phenanthrene, phenol, aniline, and the like.

The term "carbamate" is art-recognized and refers to a group

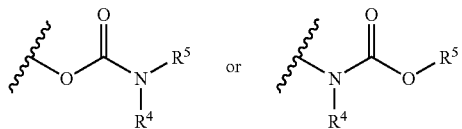

wherein $R^4$ and $R^5$ independently represent hydrogen or a hydrocarbyl group, or $R^4$ and $R^5$ taken together with the atoms to which they are attached complete a heterocycle having from 4 to 8 atoms in the ring structure.

The term "cycloalkyl", as used herein, refers to a non-aromatic saturated or unsaturated ring in which each atom of the ring is carbon. In certain embodiments, a cycloalkyl ring contains from 3 to 10 atoms, and in more specific embodiments from 5 to 7 atoms.

The term "carbonate" is art-recognized and refers to a group $—OCO_2—R^4$, wherein $R^4$ represents a hydrocarbyl group.

The term "carboxy", as used herein, refers to a group represented by the formula $—CO_2H$.

The term "ester", as used herein, refers to a group $—C(O)OR^4$ wherein $R^4$ represents a hydrocarbyl group.

The term "ether", as used herein, refers to a hydrocarbyl group linked through an oxygen to another hydrocarbyl group. Accordingly, an ether substituent of a hydrocarbyl group may be hydrocarbyl-O—. Ethers may be either symmetrical or unsymmetrical. Examples of ethers include, but are not limited to, heterocycle-O-heterocycle and aryl-O-heterocycle. Ethers include "alkoxyalkyl" groups, which may be represented by the general formula alkyl-O-alkyl.

The term "guanidinyl" is art-recognized and may be represented by the general formula

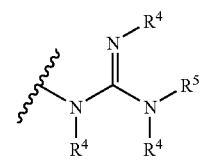

wherein $R^4$ and $R^5$ independently represent hydrogen or a hydrocarbyl.

The terms "halo" and "halogen" as used herein mean halogen and include chloro, fluoro, bromo, and iodo.

The terms "hetaralkyl" and "heteroaralkyl", as used herein, refer to an alkyl group substituted with a hetaryl group.

The terms "heteroaryl" and "hetaryl" include substituted or unsubstituted aromatic single ring structures, in certain specific embodiments 5- to 7-membered rings, more specifically 5- to 6-membered rings, whose ring structures include at least one heteroatom, in some embodiments one to four heteroatoms, and in more specific embodiments one or two heteroatoms. The terms "heteroaryl" and "hetaryl" also include polycyclic ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. Heteroaryl groups include, for example, pyrrole, furan, thiophene, imidazole, oxazole, thiazole, pyrazole, pyridine, pyrazine, pyridazine, and pyrimidine, and the like.

The term "heteroatom" as used herein means an atom of any element other than carbon or hydrogen. Typical heteroatoms are nitrogen, oxygen, and sulfur.

The terms "heterocyclyl", "heterocycle", and "heterocyclic" refer to substituted or unsubstituted non-aromatic ring structures, in certain specific embodiments 3- to 10-membered rings, more specifically 3- to 7-membered rings, whose ring structures include at least one heteroatom, in some embodiments one to four heteroatoms, and in more specific embodiments one or two heteroatoms. The terms "heterocyclyl" and "heterocyclic" also include polycyclic ring systems having two or more cyclic rings in which two or more carbons are common to two adjoining rings wherein at least one of the rings is heterocyclic, e.g., the other cyclic rings can be cycloalkyls, cycloalkenyls, cycloalkynyls, aryls, heteroaryls, and/or heterocyclyls. Heterocyclyl groups include, for example, piperidine, piperazine, pyrrolidine, morpholine, lactones, lactams, and the like.

The term "heterocyclylalkyl", as used herein, refers to an alkyl group substituted with a heterocycle group.

The term "hydrocarbyl", as used herein, refers to a group that is bonded through a carbon atom that does not have a =O or =S substituent, and typically has at least one carbon-hydrogen bond and a primarily carbon backbone, but may optionally include heteroatoms. Thus, groups like methyl, ethoxyethyl, 2-pyridyl, and trifluoromethyl are considered to be hydrocarbyl for the purposes herein, but substituents such as acetyl (which has a =O substituent on the linking carbon) and ethoxy (which is linked through oxygen, not carbon) are not. Hydrocarbyl groups include, but are not limited to aryl, heteroaryl, carbocycle, heterocycle, alkyl, alkenyl, alkynyl, and combinations thereof.

The term "hydroxyalkyl", as used herein, refers to an alkyl group substituted with a hydroxy group.

The term "lower" when used in conjunction with a chemical moiety, such as, acyl, acyloxy, alkyl, alkenyl, alkynyl, or alkoxy is meant to include groups where there are ten or fewer non-hydrogen atoms in the substituent, and in certain embodiments, six or fewer. A "lower alkyl", for example, refers to an alkyl group that contains ten or fewer carbon atoms, in specific embodiments six or fewer. In certain embodiments, acyl, acyloxy, alkyl, alkenyl, alkynyl, or alkoxy substituents defined herein are respectively lower acyl, lower acyloxy, lower alkyl, lower alkenyl, lower alkynyl, or lower alkoxy, whether they appear alone or in combination with other substituents, such as in the recitations hydroxyalkyl and aralkyl (in which case, for example, the atoms within the aryl group are not counted when counting the carbon atoms in the alkyl substituent).

The terms "polycyclyl", "polycycle", and "polycyclic" refer to two or more rings (e.g., cycloalkyls, cycloalkenyls, cycloalkynyls, aryls, heteroaryls, and/or heterocyclyls) in which two or more atoms are common to two adjoining rings, e.g., the rings are "fused rings". Each of the rings of the polycycle can be substituted or unsubstituted. In certain embodiments, each ring of the polycycle contains from 3 to 10 atoms in the ring, more specifically from 5 to 7.

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc., under conditions in which the compound is to be used. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. Substituents may include any substituents described herein, for example, a halogen, a hydroxyl, a carbonyl (such as a keto, a carboxy, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain may themselves be substituted, if appropriate.

Unless specifically described as "unsubstituted", references to chemical moieties herein are understood to include substituted variants. For example, reference to an "aryl" group or moiety implicitly includes both substituted and unsubstituted variants.

The term "sulfate" is art-recognized and refers to the group —OSO$_3$H, or a pharmaceutically acceptable salt thereof.

The term "sulfonamide" is art-recognized and refers to the group represented by the general formulae

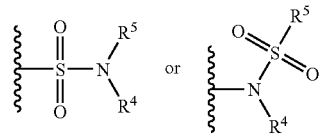

wherein $R^4$ and $R^5$ independently represent hydrogen or hydrocarbyl.

The term "sulfoxide" is art-recognized and refers to the group —S(O)—$R^4$, wherein $R^4$ represents a hydrocarbyl.

The term "sulfonate" is art-recognized and refers to the group SO$_3$H, or a pharmaceutically acceptable salt thereof.

The term "sulfone" is art-recognized and refers to the group —S(O)$_2$—$R^4$, wherein $R^4$ represents a hydrocarbyl.

The term "thioalkyl", as used herein, refers to an alkyl group substituted with a thiol group.

The term "thioester", as used herein, refers to a group —C(O)S$R^4$ or —SC(O)$R^4$ wherein $R^4$ represents a hydrocarbyl.

The term "thioether", as used herein, is equivalent to an ether, wherein the oxygen is replaced with a sulfur.

The term "urea" is art-recognized and may be represented by the general formula

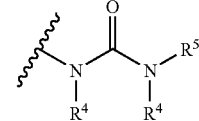

wherein $R^4$ and $R^5$ independently represent hydrogen or a hydrocarbyl.

Epoxide Inhibitor Compounds

In one aspect, the invention provides novel epoxide inhibitor compounds. In some embodiments, the epoxide inhibitors are represented by structural formula (I):

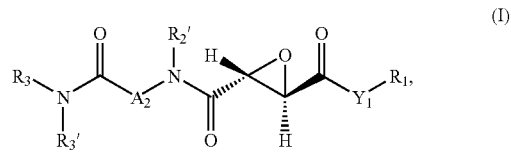

or a pharmaceutically acceptable derivative or prodrug thereof, wherein:
  $Y_1$ is O or N—$R_1$';
  $A_2$ is —C($R_2$')($R_2$")—, arylene, cycloalkylene, heteroarylene, or heterocycloalkylene, optionally substituted with 1-3 J groups;

R₂ and R₂" are independently H, alkyl, alkenyl, alkynyl, aryl, aralkyl, aralkenyl, cycloalkyl, cycloalkenyl, heterocyclyl, heterocyclylalkyl, heterocyclylalkenyl, heteroaryl, heteroaralkyl, carboxyalkyl, or carboxamidoalkyl, R₂ and R₂" taken together with the C atom to which they are attached complete a cyclic structure having from 4 to 8 atoms in the ring, or R₂ and R₂" taken together with the C atom to which they are attached form an alkene; wherein R₂ and R₂" are independently optionally substituted with 1-3 J groups and wherein any alkyl carbon atom may be replaced by a heteroatom;

$R_1$, $R_1'$, $R_2'$, $R_3$, and $R_3'$ are independently H, alkyl, alkenyl, alkynyl, aryl, aralkyl, aralkenyl, cycloalkyl, cycloalkenyl, heterocyclyl, heterocyclylalkyl, heterocyclylalkenyl, heteroaryl, heteroaralkyl, carboxyalkyl, or carboxamidoalkyl, and are optionally substituted with 1-3 J groups, wherein any alkyl carbon atom may be replaced by a heteroatom and wherein $R_3$ and $R_3'$ taken together with the N atom to which they are attached complete a cyclic structure having from 4 to 8 atoms in the ring;

J is alkyl, aryl, aralkyl, alkoxy, aryloxy, aralkoxy, cycloalkyl, cycloalkoxy, heterocyclyl, heterocyclyloxy, heterocyclylalkyl, heteroaryl, heteroaralkyl, keto, hydroxy, thio, amino, alkylamino, alkanoylamino, aroylamino, aralkanoylamino, carboxy, carbonate, carbamate, guanidinyl, urea, halo, cyano, nitro, formyl, phosphoryl, sulfonyl, or sulfonamido and is optionally substituted with 1-3 $J^1$ groups;

$J^1$ is alkyl, aryl, aralkyl, alkoxy, aryloxy, heterocyclyl, heterocyclyloxy, keto, hydroxy, thio, amino, alkanoylamino, aroylamino, carboxy, carbonate, carbamate, guanidinyl, urea, halo, cyano, nitro, formyl, phosphoryl, sulfonyl, or sulfonamido;

provided that when $A_2$ is —C(R₂)(R₂")—, R₂ is a naturally-occurring amino acid side chain, and R₂" is H, then —Y₁—R₁ is not —OH, —OCH₃, or —OCH₂CH₃;

provided that when $A_2$ is —C(R₂)(R₂")—, R₂ is —CH₂—CH(CH₃)₂, and R₂" is H, then R₃ is not —CH₂—CH₂—CH₂—NH—C(═NH)—NH₂ or —C(H)(NH₂)—CH₂—CH₂—CH₂—NH—C(═NH)—NH₂, and R₃ and R₃' together with the N atom to which they are attached do not form a 5-membered ring substituted with carboxy;

when $A_2$ is —C(R₂)(R₂")—, R₂ is —CH₂-Phenyl, and R₂" is H, then R₃ and R₃' are not both —CH₃; and when $A_2$ is —C(R₂)(R₂")—, R₂ is —CH₂—CH₂—CH₂—CH₂—CH₂—NH₂, and R₂" is H, then R₃ is not naphthyl.

In some embodiments of the invention, the epoxide inhibitors are represented by structural formula (II):

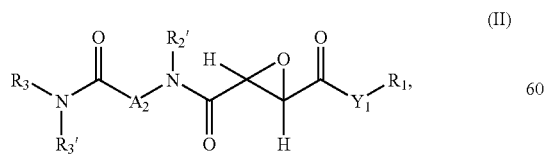

(II)

or a pharmaceutically acceptable derivative or prodrug thereof, wherein the substituents are all as defined above, except that R₁ is selected from the group consisting of:

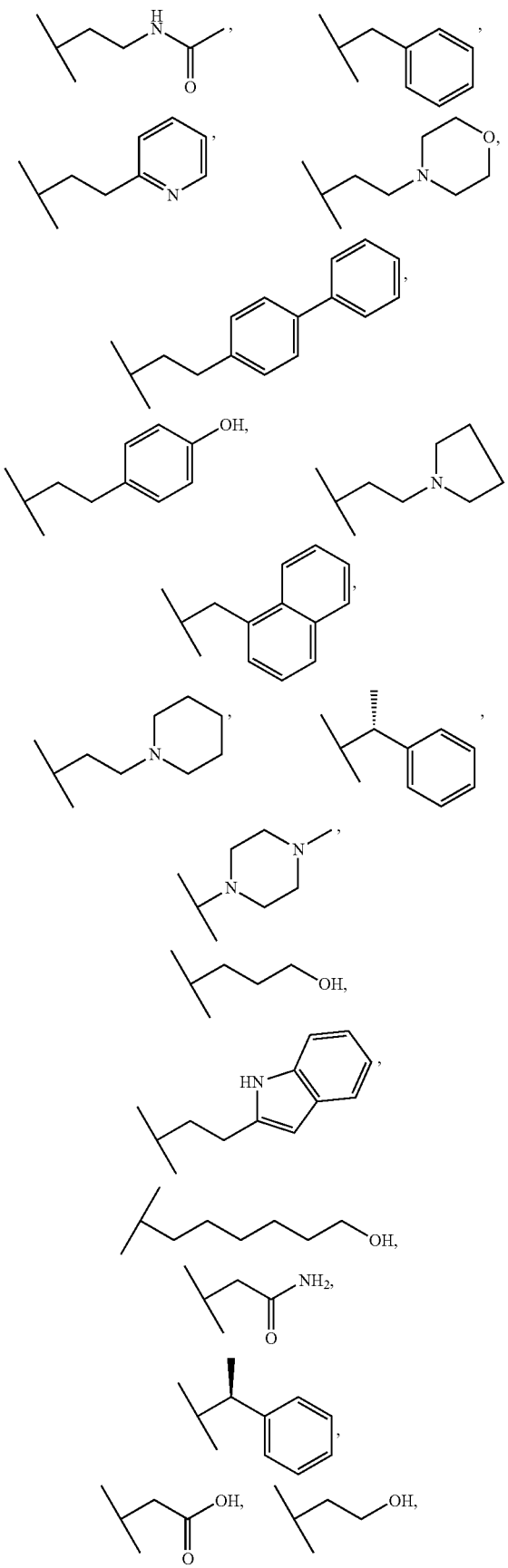

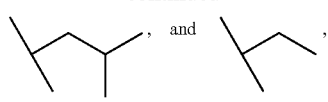

R₃ and R₃' are independently H, alkyl, alkenyl, alkynyl, aryl, aralkyl, aralkenyl, cycloalkyl, cycloalkenyl, heterocyclyl, heterocyclylalkyl, heterocyclylalkenyl, heteroaryl, heteroaralkyl, carboxyalkyl, or carboxamidoalkyl, and are optionally substituted with 1-3 J groups, wherein any alkyl carbon atom may be replaced by a heteroatom, and provided that when $Y_1$ is O, $R_1$ is not

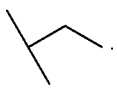

In other embodiments of the invention, the inhibitors are represented by structural formula (II), or a pharmaceutically acceptable derivative or prodrug thereof, and the substituents are all as defined above, except that $R_2''$ is H and $R_2$ is selected from the group consisting of:

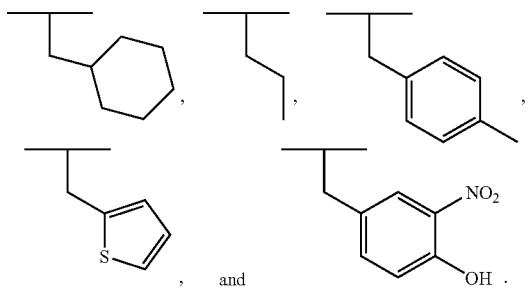

In still other embodiments of the invention, the inhibitors are represented by structural formula (II), or a pharmaceutically acceptable derivative or prodrug thereof, and the substituents are all as defined above, except that $R_3'$ is H and $R_3$ is selected from the group consisting of:

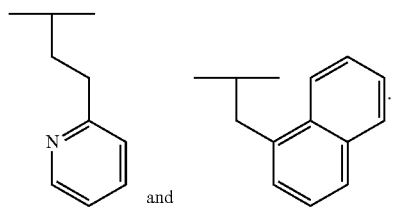

In yet still other embodiments of the invention, the inhibitors are represented by structural formula (II), or a pharmaceutically acceptable derivative or prodrug thereof, and the substituents are all as defined above, except that $R_2'$ is not H.

In some of the above embodiments, $R_2$ and $R_2''$ taken together with the C atom to which they are attached complete a cyclic structure having from 5, 6, or 7 atoms in the ring. In more specific embodiments, $R_2$ and $R_2''$ taken together with the C atom to which they are attached complete a cyclic structure having 5 or 6 atoms in the ring.

In some of the above embodiments, $R_3$ and $R_3'$ taken together with the N atom to which they are attached complete a cyclic structure having 5, 6, or 7 atoms in the ring. In more specific embodiments, $R_3$ and $R_3'$ taken together with the N atom to which they are attached complete a cyclic structure having 5 or 6 atoms in the ring.

In some of the above embodiments of the invention, $R_1$ and $R_3$ are independently varied through the use of different $R_1$—$NH_2$ and $R_3$—$NH_2$ reagents in the synthesis scheme shown below or by other means. For example, any commercially-available primary amine may be used to generate additional diversity in the epoxide inhibitor structures. Amines showing activity in the diversity set may be used to synthesize extended libraries using other members of the structurally related cluster containing the amine hit. This approach allows further optimization of leads to identify compounds with optimal potency, selectivity and drug-likeness.

In certain specific embodiments, $R_1$ and $R_3$ are independently selected from the groups shown in Table 1, where the structures shown correspond to $R_1$—$NH_2$ and $R_3$—$NH_2$. In certain specific embodiments, $R_3'$ is H. One of skill in the art would recognize that compounds of the invention with $R_1$ or $R_3$ selected from those shown in Table 1 may be synthesized by any method, not just the synthetic scheme provided below.

TABLE 1

Examples of $R_1$ and $R_3$. The structures shown correspond to either $R_1$—$NH_2$ or $R_3$—$NH_2$.

| A1: N-Acetylethylenediamine | A2: Benzylamine | A3: 2-(2-Aminoethyl)pyridine | A4: 4-(2-Aminoethyl)morpholine |
|---|---|---|---|
| $C_4H_{10}N_2O$<br>Exact Mass: 102.08<br>Mol. Wt.: 102.13 | $C_7H_9N$<br>Exact Mass: 107.07<br>Mol. Wt.: 107.15 | $C_7H_{10}N_2$<br>Exact Mass: 122.08<br>Mol. Wt.: 122.17 | $C_6H_{14}N_2O$<br>Exact Mass: 130.11<br>Mol. Wt.: 130.19 |

TABLE 1-continued

Examples of $R_1$ and $R_3$. The structures shown correspond to either $R_1$—$NH_2$ or $R_3$—$NH_2$.

| A5: 2-(4-Biphenyl)ethylamine | A6: Tyramine | A7: 1-(2-Aminoethyl)pyrrolidine | A8: 1-Naphthalenemethylamine |
|---|---|---|---|
| 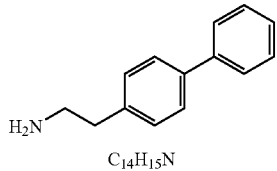<br>$C_{14}H_{15}N$<br>Exact Mass: 197.12<br>Mol. Wt.: 197.28 | 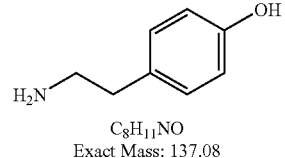<br>$C_8H_{11}NO$<br>Exact Mass: 137.08<br>Mol. Wt.: 137.18 | 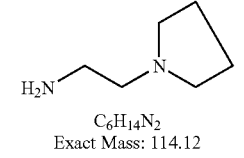<br>$C_6H_{14}N_2$<br>Exact Mass: 114.12<br>Mol. Wt.: 114.19 | 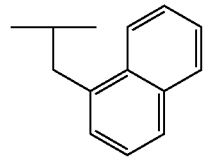<br>$C_{11}H_{11}N$<br>Exact Mass: 157.09<br>Mol. Wt.: 157.21 |

| A9: 1-(2-Aminoethyl)piperdine | A10: R-(+)alphamethylbenzylamine | A11: 1-Amino-4methylpiperzine | A12: 3amino1OTr-1-propanol |
|---|---|---|---|
| 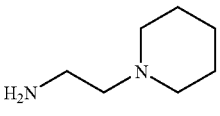<br>$C_7H_{16}N_2$<br>Exact Mass: 128.13<br>Mol. Wt.: 128.22 | 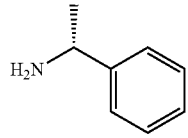<br>$C_8H_{11}N$<br>Exact Mass: 121.09<br>Mol. Wt.: 121.18 | 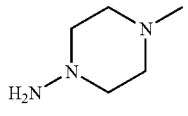<br>$C_5H_{13}N_3$<br>Exact Mass: 115.11<br>Mol. Wt.: 115.18 | 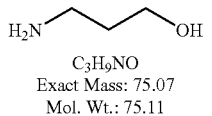<br>$C_3H_9NO$<br>Exact Mass: 75.07<br>Mol. Wt.: 75.11 |

| A13: Tryptamine | A14: 6-Amino-1-OTr-1-hexanol | A15: EthylamineHCl | A16: H-Gly-NH2-HCl |
|---|---|---|---|
| 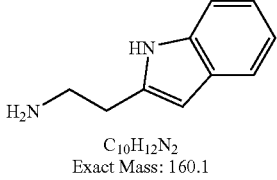<br>$C_{10}H_{12}N_2$<br>Exact Mass: 160.1<br>Mol. Wt.: 160.22 | 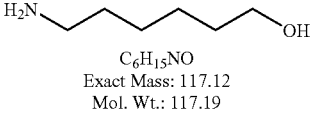<br>$C_6H_{15}NO$<br>Exact Mass: 117.12<br>Mol. Wt.: 117.19 | 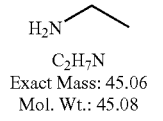<br>$C_2H_7N$<br>Exact Mass: 45.06<br>Mol. Wt.: 45.08 | 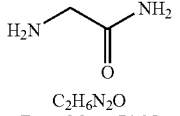<br>$C_2H_6N_2O$<br>Exact Mass: 74.05<br>Mol. Wt.: 74.08 |

| A17: H-Gly-OBut-Hcl | A18: Isobutylamine | A19: L(−)Alphamethylbenzylamine | A20: 2-Amino-1-OTr-1-ethanol |
|---|---|---|---|
| 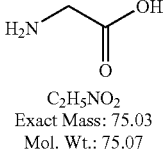<br>$C_2H_5NO_2$<br>Exact Mass: 75.03<br>Mol. Wt.: 75.07 | 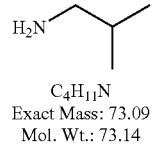<br>$C_4H_{11}N$<br>Exact Mass: 73.09<br>Mol. Wt.: 73.14 | 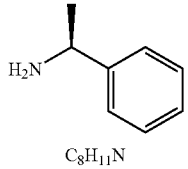<br>$C_8H_{11}N$<br>Exact Mass: 121.09<br>Mol. Wt.: 121.18 | 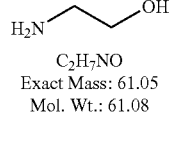<br>$C_2H_7NO$<br>Exact Mass: 61.05<br>Mol. Wt.: 61.08 |

In some embodiments, $Y_1$ is O. One of skill in the art would recognize that when $Y_1$ is O, an $R_1$ radical may nevertheless be selected from the examples of $R_1$ shown in Table 1. In other embodiments, $Y_1$ is N—$R_1'$.

In some embodiments of the invention, $A_2$ is —C($R_2$)($R_2''$)—, wherein $R_2$ and $R_2''$ are as defined above. For example, the following structures represent examples of epoxide inhibitors of the invention, wherein the $A_2$ moiety is an α-L-amino acid residue.

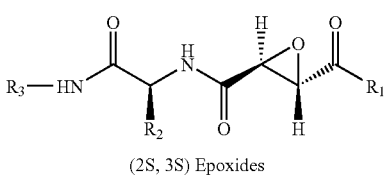

(2S, 3S) Epoxides

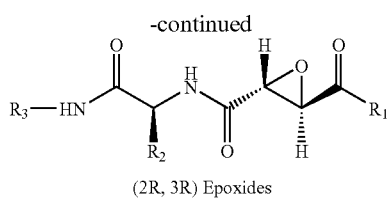

(2R, 3R) Epoxides

Compounds with these structures include those wherein $R_2$ is a naturally-occurring amino acid side chain. Naturally-occurring amino acid side chains are well known in the art. See, e.g., Stryer, *Biochemistry*, 4th ed., 1995, W.H. Freeman and Co., New York. They correspond to the side chains of glycine, alanine, valine, leucine, isoleucine, methionine, phenylalanine, tryptophan, tyrosine, serine, threonine, cysteine, asparagine, glutamine, aspartic acid, glutamic acid, histidine, lysine, and arginine. Proline is not considered to have a side chain within this definition. In alternative embodiments, the $R_2$ group may be the side chain of a non-naturally-occurring amino acid or may be another group. In some embodiments, for example, in the structures shown above, the amino acid is the L-stereoisomer. In other embodiments, the amino acid is the D-stereoisomer.

In some embodiments of the invention, the $A_2$ moiety is arylene, cycloalkylene, heteroarylene, or heterocycloalkylene. In other embodiments, the $A_2$ moiety is —C($R_2$)($R_2''$)—, wherein $R_2$ and $R_2''$ are taken together with the C atom to which they are attached to complete a cyclic structure having from 4 to 8 atoms in the ring. In still other embodiments, or $R_2$ and $R_2''$ are taken together with the C atom to which they are attached to form an alkene.

In some specific embodiments of the invention, the $A_2$ moiety is selected from the groups shown in Table 2, wherein the structures shown correspond to Fmoc-NH-$A_2$-COOH. One of skill in the art would appreciate that other Fmoc-amino acids may be used as building blocks in the synthetic scheme shown below. The skilled artisan would also appreciate that compounds of the invention having an $A_2$ moiety selected from the groups shown in Table 2 may be synthesized by any method, not just by the synthetic scheme shown below.

TABLE 2

Examples of natural and non-natural amino acid building blocks.
The structures shown correspond to Fmoc-NH-$A_2$-COOH.

| Amino Acid | Structure |
| --- | --- |
| (2furyl)alanine | 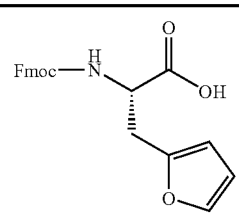 |
| (2thienyl)alanine | 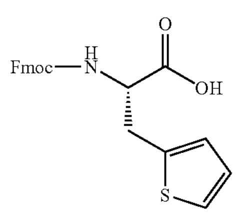 |
| 2pyridylAla | 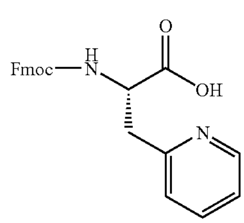 |
| 1amino1cyclohexane carboxylic acid | 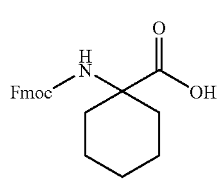 |

TABLE 2-continued

Examples of natural and non-natural amino acid building blocks.
The structures shown correspond to Fmoc-NH-$A_2$-COOH.

| Amino Acid | Structure |
| --- | --- |
| 1amino1cyclopentane carboxylic acid | 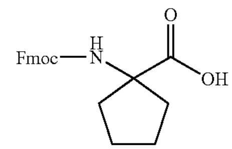 |
| 2-Abz | 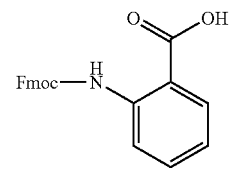 |
| 3Abz | 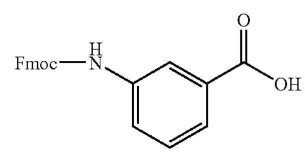 |
| 2Abu | 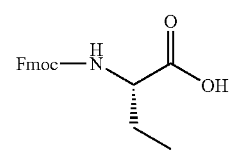 |
| 3amino3phenyl propionic acid | 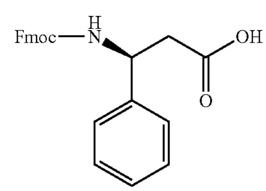 |
| dehydroAbu | 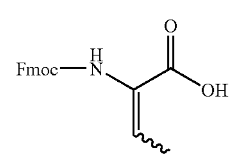 |
| ACPC | 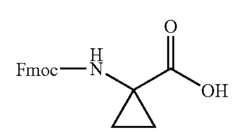 |
| Hyp | 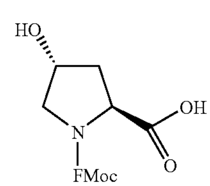 |

TABLE 2-continued

Examples of natural and non-natural amino acid building blocks.
The structures shown correspond to Fmoc-NH-A₂-COOH.

| Amino Acid | Structure |
|---|---|
| Igl | Fmoc-NH-CH(COOH)-CH₂-indanyl |
| Inp | Fmoc-N-piperidine-4-COOH |
| 1-Nal | Fmoc-NH-CH(COOH)-CH₂-(1-naphthyl) |
| 2-Nal | Fmoc-NH-CH(COOH)-CH₂-(2-naphthyl) |
| Nva | Fmoc-NH-CH(COOH)-CH₂CH₂CH₃ |
| 4-nitroPhe | Fmoc-NH-CH(COOH)-CH₂-C₆H₄-NO₂ |
| 4MethylPhe | Fmoc-NH-CH(COOH)-CH₂-C₆H₄-CH₃ |
| 4Methyl-DPhe | Fmoc-NH-CH(COOH)-CH₂-C₆H₄-CH₃ (D) |
| Phe(pI) | Fmoc-NH-CH(COOH)-CH₂-C₆H₄-I |
| Phe4NH(Boc) | Fmoc-NH-CH(COOH)-CH₂-C₆H₄-NHBoc |
| Aib | Fmoc-NH-C(CH₃)₂-COOH |
| AllylGly | Fmoc-NH-CH(COOH)-CH₂-CH=CH₂ |
| Amb | Fmoc-HN-CH₂-C₆H₄-COOH |
| Amc | Fmoc-HN-CH₂-cyclohexyl-COOH |

TABLE 2-continued

Examples of natural and non-natural amino acid building blocks.
The structures shown correspond to Fmoc-NH-A$_2$-COOH.

| Amino Acid | Structure |
|---|---|
| Bip | (structure) |
| Bpa | (structure) |
| Cba | (structure) |
| Cha | (structure) |
| deltaLeu | (structure) |
| deltaVal | (structure) |
| hPhe | (structure) |
| Phg | (structure) |
| pip | (structure) |
| Dpip | (structure) |
| propargylglycine | (structure) |
| Thz | (structure) |
| Tic | (structure) |
| Tle | (structure) |

TABLE 2-continued

Examples of natural and non-natural amino acid building blocks.
The structures shown correspond to Fmoc-NH-A$_2$-COOH.

| Amino Acid | Structure |
| --- | --- |
| 3-Nitro Tyr | 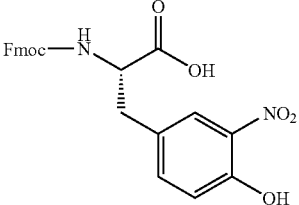 |
| leu | 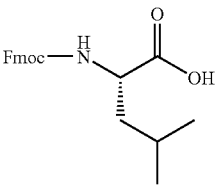 |

In yet another embodiment of the invention, R$_3$ is

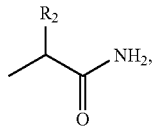

wherein R$_2$ is defined as above.

Specific compound embodiments of the invention are summarized below in Table 4.

The compounds of the instant invention contain asymmetric carbon atoms and thus exist in different stereoisomeric forms. In certain embodiments, the compounds contain an (S,S) epoxide. In other embodiments, the compounds contain an (R,R) epoxide. Compounds of the invention may be provided in at least partially purified stereochemical forms or as mixtures of enantiomers and/or diastereomers. Unless a specific stereochemistry is indicated, it should be understood that all of the optical isomers and mixtures thereof are encompassed.

In some embodiments of the invention, the compounds are provided in at least partially purified stereochemical form. An enantiomeric excess or a diasterieomeric excess exists where one enantiomer or diasteriomer, respectively, is present in larger chemical amounts than another. As used herein, the "enantiomeric ratio" is the molar ratio between two enantiomeric structures in a mixture. The "diasteriomeric ratio" is the molar ratio between two specified diasteriomeric structures in a mixture. For enantiomeric or diasteriomeric epoxide compounds of the instant invention, the enantiomeric or diasteriomeric ratio is the molar ratio between those two stereoisomers in a mixture, e.g. the ratio between an (S,S) and an (R,R) epoxide stereoisomer. In the case of compounds that are present in at least partially purified stereochemical form, the enantiomeric ratio or diasteriomeric ratio is in some embodiments at least 2. In other embodiments of the invention, the enantiomeric ratio or diasteriomeric ratio is at least 4, at least 8, at least 20, at least 50, or even higher.

When a particular stereochemical or geometric isomer is specified in a structure, or when a particular isomeric purity is indicated, the particular form can be obtained by asymmetric synthesis, synthesis from optically pure precursors, or by resolution of racemates or other mixtures of stereochemical or geometric isomers. Resolution of racemates or other mixtures may also be accomplished, for example, by conventional methods such as crystallization in the presence of a resolving agent, or chromatography, using, for example a chiral HPLC column.

As used herein, the compounds of the invention are defined to include pharmaceutically acceptable derivatives or prodrugs thereof. A "pharmaceutically acceptable derivative or prodrug" means any pharmaceutically acceptable salt, ester, salt of an ester, or other derivative of a compound of this invention, which, upon administration to a recipient, is capable of providing or provides (directly or indirectly) a compound of the invention.

Accordingly, this invention also provides prodrugs of the compounds of the invention, which are derivatives that are designed to enhance biological properties such as oral absorption, clearance, metabolism, or compartmental distribution. Such derivations are well known in the art.

As the skilled practitioner realizes, the compounds of the invention may be modified by appending appropriate functionalities to enhance selective biological properties. Such modifications are known in the art and include those which increase biological penetration into a given biological compartment (e.g., blood, lymphatic system, central nervous system), increase oral availability, increase solubility to allow administration by injection, alter metabolism, or alter rate of excretion.

Certain derivatives and prodrugs are those that increase the bioavailability of the compounds of the invention when such compounds are administered to an individual (e.g., by allowing an orally administered compound to be more readily absorbed into the blood), have more favorable clearance rates or metabolic profiles, or enhance delivery of the parent compound to a biological compartment (e.g., the brain or lymphatic system) relative to the parent species. Examples of prodrugs include derivatives in which a group that enhances aqueous solubility or active transport through the gut membrane is appended to the structure.

In some embodiments, the compounds of the invention are provided in the form of pharmaceutically acceptable salts. Compounds containing an amine may be basic in nature and accordingly may react with any number of inorganic and organic acids to form pharmaceutically acceptable acid addition salts. Acids commonly employed to form such salts include inorganic acids such as hydrochloric, hydrobromic, hydriodic, sulfuric and phosphoric acid, as well as organic acids such as para-toluenesulfonic, methanesulfonic, oxalic, para-bromophenylsulfonic, carbonic, succinic, citric, benzoic and acetic acid, and related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephathalate, sulfonate, xylenesulfonate, phenylacetate, phenylpropionate, phenylbutyrate, citrate, lactate, β-hydroxybutyrate, glycollate, maleate, tartrate, methanesulfonate, propanesulfonates, naphthalene-1-sulfonate, naphthalene-2-sulfonate, mandelate, hippurate, gluconate, lactobionate, and the like salts. In certain specific embodiments, pharmaceutically acceptable acid addition salts include those formed with mineral acids such as hydrochloric acid and hydrobromic acid, and those formed with organic acids such as fumaric acid and maleic acid.

Compounds of the instant invention that are acidic in nature may accordingly react with any number of inorganic and organic bases to form pharmaceutically acceptable base salts. Specific bases include the mineral bases, such as NaOH and KOH, but one of skill in the art would appreciate that other bases may also be used. See Ando et al., *Remington: The Science and Practice of Pharmacy,* 20th ed. 700-720 (Alfonso R. Gennaro ed.), 2000.

The pharmaceutically acceptable addition salts of the compounds of the invention may also exist as various solvates, such as with water, methanol, ethanol, dimethylformamide, and the like. Mixtures of such solvates may also be prepared. The source of such solvate may be from the solvent of crystallization, inherent in the solvent of preparation or crystallization, or adventitious to such solvent.

Synthesis of the Epoxide Inhibitors

According to another embodiment, the present invention provides methods of producing the above-defined epoxide inhibitors of cysteine proteases.

The compounds may be synthesized using conventional techniques, for example using the following solid-phase synthetic scheme. See also Verhelst and Bogyo, *ChemBioChem* 6:824-827, 2005; U.S. Provisional Patent Application No. 60/642,891, filed Jan. 10, 2005; and U.S. patent application Ser. No. 11/329,818, filed Jan. 10, 2006; which are incorporated by reference herein in their entireties. Advantageously, these compounds are synthesized from readily available starting materials.

Synthetic Scheme

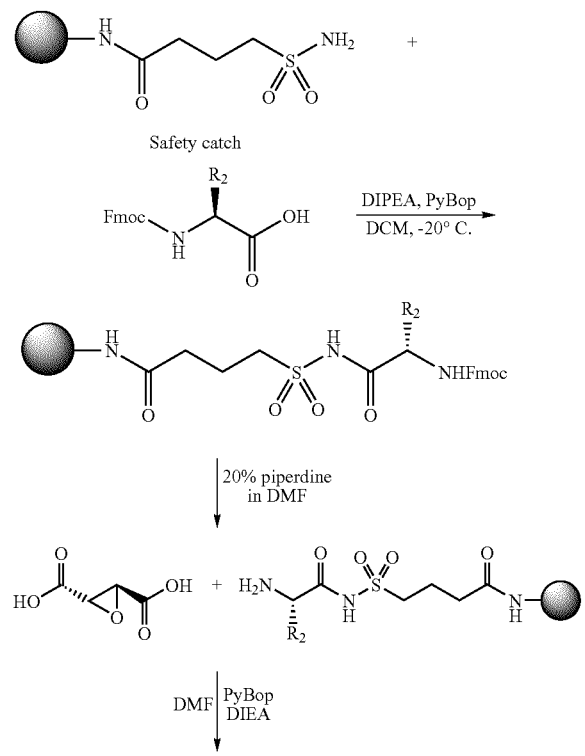

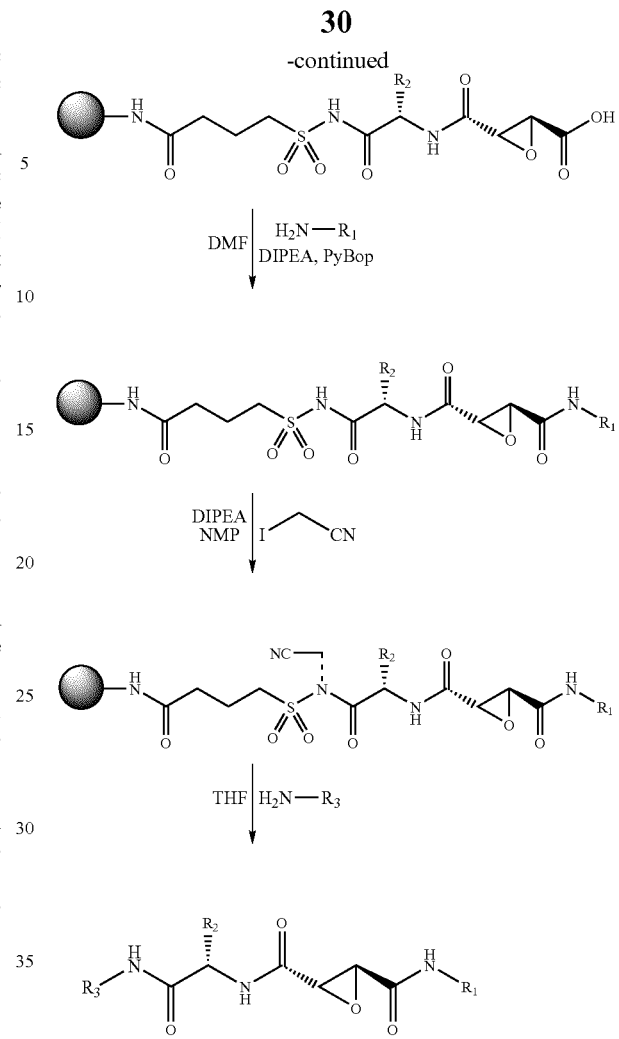

The epoxide inhibitors can be synthesized as the (2S, 3S) or (2R, 3R) isomers based on the starting epoxide used in the synthesis. The (2S, 3S) isomer is shown in the synthetic scheme above but can be easily substituted for the (2R, 3R) version. In this example, the $R_2$-containing residue is added as an α-L-amino acid, but the skilled artisan would understand that the use of other, non-natural, amino acid residues at this position is within the scope of the invention. See Table 2, above, for examples of natural and non-natural Fmoc-amino acid building blocks useful in the synthetic scheme.

As can be appreciated by the skilled artisan, the synthetic methods disclosed herein are not intended to comprise a comprehensive list of all means by which the compounds described and claimed in this application may be synthesized. Further methods will be evident to those of ordinary skill in the art. Additionally, the various synthetic steps described above may be performed in an alternate sequence or order to give the desired compounds. Synthetic chemistry transformations and methodologies useful in synthesizing the epoxide inhibitor compounds described herein are known in the art and include, for example, those described in R. Larock, *Comprehensive Organic Transformations* (1989); T. W. Greene and P. G. M. Wuts, *Protective Groups in Organic Synthesis,* 2d. Ed. (1991); L. Fieser and M. Fieser, *Fieser and Fieser's Reagents for Organic Synthesis* (1994); and L. Paquette, ed., *Encyclopedia of Reagents for Organic Synthesis* (1995).

Pharmaceutical Compositions

The compounds of the invention may be administered as a pharmaceutical composition containing, for example, a compound of the invention and a pharmaceutically acceptable carrier. Pharmaceutically acceptable carriers are well known in the art and include, for example, aqueous solutions such as water or physiologically buffered saline or other solvents or vehicles such as glycols, glycerol, oils such as olive oil or injectable organic esters. In a specific embodiment, when such pharmaceutical compositions are for human administration, the aqueous solution is pyrogen free, or substantially pyrogen free. The excipients may be chosen, for example, to effect delayed release of an agent or to selectively target one or more cells, tissues or organs. The pharmaceutical composition may be in dosage unit form such as tablet, capsule, sprinkle capsule, granule, powder, syrup, suppository, injection or the like. The composition may also be present in a transdermal delivery system, e.g., a skin patch.

A pharmaceutically acceptable carrier may contain physiologically acceptable agents that act, for example, to stabilize or to increase the absorption of a compound of the instant invention. Such physiologically acceptable agents include, for example, carbohydrates, such as glucose, sucrose or dextrans, antioxidants, such as ascorbic acid or glutathione, chelating agents, low molecular weight proteins or other stabilizers or excipients. The choice of a pharmaceutically acceptable carrier, including a physiologically acceptable agent, depends, for example, on the route of administration of the composition. The pharmaceutical composition also may comprise a liposome or other polymer matrix, which may have incorporated therein, for example, a compound of the invention. Liposomes, for example, which consist of phospholipids or other lipids, are nontoxic, physiologically acceptable and metabolizable carriers that are relatively simple to make and administer.

The phrase "pharmaceutically acceptable" is employed herein to refer to those compounds, materials, compositions, and/or dosage forms that are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition, or vehicle, such as a liquid or solid filler, diluent, excipient, solvent, or encapsulating material, involved in carrying or transporting the subject compounds from one organ, or portion of the body, to another organ, or portion of the body. Each carrier must be "acceptable" in the sense of being compatible with the other ingredients of the formulation and not injurious to the patient. Some examples of materials that can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations. See *Remington: The Science and Practice of Pharmacy*, 20th ed. (Alfonso R. Gennaro ed.), 2000.

A pharmaceutical composition containing a compound of the instant invention may be administered to a host by any of a number of routes of administration including, for example, orally (for example, drenches as in aqueous or non-aqueous solutions or suspensions, tablets, boluses, powders, granules, pastes for application to the tongue); sublingually; anally, rectally, or vaginally (for example, as a pessary, cream, or foam); parenterally (including intramuscularly, intravenously, subcutaneously, or intrathecally as, for example, a sterile solution or suspension); nasally; intraperitoneally; subcutaneously; transdermally (for example as a patch applied to the skin); or topically (for example, as a cream, ointment or spray applied to the skin). The compound may also be formulated for inhalation. In certain embodiments, a compound of the instant invention may be simply dissolved or suspended in sterile water. Details of appropriate routes of administration and compositions suitable for same can be found in, for example, U.S. Pat. Nos. 6,110,973; 5,763,493; 5,731,000; 5,541,231; 5,427,798; 5,358,970; and 4,172,896, as well as in patents cited therein.

The formulations of the present invention may conveniently be presented in unit dosage form and may be prepared by any methods well known in the art of pharmacy. The amount of active ingredient that can be combined with a carrier material to produce a single dosage form will vary depending upon the host being treated and the particular mode of administration. The amount of active ingredient that can be combined with a carrier material to produce a single dosage form will generally be that amount of the compound that produces a therapeutic effect. Generally, out of one hundred percent, this amount will range from about 1 percent to about 99 percent of active ingredient, in some embodiments from about 5 percent to about 70 percent, and in more specific embodiments from about 10 percent to about 30 percent.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary, or paste.

In solid dosage forms of the invention for oral administration (capsules, tablets, pills, dragees, powders, granules and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof, and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that may be used include polymeric substances and waxes. The active ingredient may also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions may also include adjuvants such as wetting agents, emulsifying and suspending agents, sweetening, flavoring, coloring, perfuming, and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, and tragacanth, and mixtures thereof.

Formulations of the pharmaceutical compositions of the invention for rectal, vaginal, or urethral administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Alternatively or additionally, compositions may be formulated for delivery via a catheter, stent, wire, or other intraluminal device. Delivery via such devices may be especially useful for delivery to the bladder, urethra, ureter, rectum, or intestine.

Formulations of the present invention which are suitable for vaginal administration also include pessaries, tampons, creams, gels, pastes, foams, or spray formulations containing such carriers as are known in the art to be appropriate.

Dosage forms for the topical or transdermal administration of a compound of this invention include powders, sprays, ointments, pastes, creams, lotions, gels, solutions, patches, and inhalants. The active compound may be mixed under sterile conditions with a pharmaceutically acceptable carrier, and with any preservatives, buffers, or propellants that may be required.

The ointments, pastes, creams, and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays may contain, in addition to a compound of this invention, excipients such as lactose, talc, silicic acid, aluminum hydroxide, calcium silicates, and polyamide powder, or mixtures of these substances. Sprays may additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms may be made by dissolving or dispersing the compound in the proper medium. Absorption enhancers may also be used to increase the flux of the compound across the skin. The rate of such flux may be controlled by either providing a rate controlling membrane or dispersing the compound in a polymer matrix or gel.

Ophthalmic formulations, eye ointments, powders, solutions, and the like, are also contemplated as being within the scope of this invention.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, and intrasternal injection and infusion.

Pharmaceutical compositions of this invention suitable for parenteral administration comprise one or more compounds of the invention in combination with one or more pharmaceutically acceptable sterile isotonic aqueous or nonaqueous solutions, dispersions, suspensions, or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity may be maintained, for example, by the use of coating materials, such as lecithin, by the maintenance of the required particle size in the case of dispersions, and by the use of surfactants.

These compositions may also contain adjuvants such as preservatives, wetting agents, emulsifying agents, and dispersing agents. Prevention of the action of microorganisms may be ensured by the inclusion of various antibacterial and antifungal agents, for example, paraben, chlorobutanol, phenol sorbic acid, chelators and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle.

Injectable depot forms are made by forming microencapsuled matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissue.

Methods of introduction may also be provided by rechargeable or biodegradable devices. Various slow release polymeric devices have been developed and tested in vivo in recent years for the controlled delivery of drugs. A variety of biocompatible polymers (including hydrogels), including both biodegradable and non-degradable polymers, may be used to form an implant for the sustained release of a compound at a particular target site.

Packaged Pharmaceuticals

The pharmaceutical compositions of the invention may usefully be provided as packaged pharmaceuticals. The compositions are thus included in a container, package, or dispenser, either alone or as part of a kit with labels and instructions for administration. The packaged pharmaceuticals may in some cases further comprise additional therapeutics for use in combination with the provided composition. Such therapeutics may include, e.g., one or more chemotherapeutic agents.

Use of the Compounds and Compositions

The invention further provides methods for using the compounds and compositions described herein. In one aspect, the pharmaceutical compositions of the invention are used in methods for inhibiting a papain-family cathepsin in a mammalian host. Accordingly, the methods comprise administering to the mammalian host in need thereof a pharmaceutical composition as described above.

Examples of papain-family cathepsins usefully inhibited according to the methods of the invention include, e.g., cathepsins B, C, H, K, L, S, F, O, P, V, W, X, Y, and Z. See, e.g., Schirmeister and Kaeppler, *Mini Reviews Med. Chem.* 3:361-373, 2003, and references cited therein.

The host receiving treatment according to the disclosed methods is any mammal in need of such treatment. Such mammals include, e.g., humans, ovines, bovines, equines, porcines, canines, felines, non-human primate, mice, and rats. In certain specific embodiments, the host is a human. In certain other specific embodiments, the host is a non-human mammal. In some embodiments, the host is a farm animal. In other embodiments, the host is a pet.

In another aspect, the pharmaceutical compositions of the invention are used in methods for treating or preventing a disease associated with a papain-family cathepsin in a mammalian host. Such methods may comprise, for example, administering to the mammalian host in need thereof a therapeutically-effective amount of a pharmaceutical composition as described above.

By "therapeutically effective amount" is meant the concentration of a compound that is sufficient to elicit the desired therapeutic effect (e.g., treatment or prevention of a disease associated with a papain-family cathepsin, etc.). It is generally understood that the effective amount of the compound will vary according to the weight, gender, age, and medical history of the host. Other factors that influence the effective amount may include, but are not limited to, the severity of the patient's condition, the disorder being treated, the stability of the compound, and, if desired, another type of therapeutic agent being administered with the compound of the invention. A larger total dose may be delivered by multiple administrations of the agent. Methods to determine efficacy and dosage are known to those skilled in the art. See, e.g., Roden, *Harrison's Principles of Internal Medicine*, Ch. 3, McGraw-Hill, 2004.

Actual dosage levels of the active ingredients in the pharmaceutical compositions of the invention may be varied so as to obtain an amount of the active ingredient that is effective to achieve the desired therapeutic response for a particular patient, composition, and mode of administration, without being toxic to the patient.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound that is the lowest dose effective to produce a therapeutic effect. Such an effective dose will generally depend upon the factors described above.

If desired, the effective daily dose of the active compound may be administered as one, two, three, four, five, six, or more sub-doses administered separately at appropriate intervals throughout the day, optionally, in unit dosage forms. In certain embodiments of the present invention, the active compound may be administered two or three times daily. In specific embodiments, the active compound is administered once daily.

It is contemplated that a therapeutically effective amount of the compound to be administered to a host (e.g., a mammal, in some embodiments, a human) is in the range of 1 mg/day and 100 mg/day. In certain embodiments, the therapeutically effective amount of the compound to be administered to a host is in a range of 1 mg/day and 60 mg/day. In more specific embodiments, the therapeutically effective amount of the compound to be administered to a host is in a range of 5 mg/day and 30 mg/day.

In yet another aspect, the pharmaceutical compositions of the invention are used in methods for treating or preventing particular diseases. The methods comprise, for example, administering to the mammalian host in need thereof a therapeutically-effective amount of a pharmaceutical composition as described above.

Cathepsins play a major role in the normal degradation and processing of proteins and are found in a wide variety of tissues. Thus, aberrant activity of a cathepsin, e.g., as a result of inappropriately-timed expression or enhanced activation, would be expected to have pathological consequences. In this regard, certain cathepsin proteases have been associated with a number of disease states, including immune-related diseases, inflammatory disease, tissue remodeling-related diseases, cancer and infectious diseases.

Intracellular proteolysis generates small peptides for presentation to T-lymphocytes to induce immune responses. Cathepsin S, L, F, and V have all been shown to process the invariant chain required for normal functioning of the MHC class II associated antigen processing and presentation (Nakagawa et al., *Science* 280:450-453, 1998; Shi et al., *Immunity* 10:197-206, 1999). The immune system screens for autologous cells that are virally infected or have undergone oncogenic transformation. One embodiment of the invention is a method for inhibiting antigen presentation in a cell, including exposing the cell to a compound or composition described herein.

A compound or composition of the invention may likewise be used to treat or prevent immune-related conditions. Such conditions comprise allergy, asthma, organ/tissue rejection (graft-versus-host disease) and auto-immune diseases, including, but not limited to, diabetes, lupus, rheumatoid arthritis, psoriasis, multiple sclerosis and inflammatory bowel disease (such as ulcerative colitis and Crohn's disease) (Riese et al., *J. Clin. Invest.* 101:2351-2363, 1998; Maehr et al., *J. Clin. Invest.* 115: 2934-2943, 2005). Thus, according to a further embodiment of the invention, methods are provided for suppressing the immune system of a subject, including administering to the subject an effective amount of a compound or composition described herein.

Many pathological conditions employ multiple signaling pathways. The inflammatory process plays an important role in the pathogenesis of a variety of diseases. Psoriasis is a T-cell mediated inflammatory disease that is characterized by hyperproliferation and aberrant differentiation. Protein expression and enzymatic activity of cathepsin D has been shown to increase in differentiating keratinocytes (Egberts et al., *J. Cell Science* 117: 2295-2307, 2004).

Numerous lung diseases, such as chronic obstructive pulmonary disease (COPD), bronchitis, emphysema, and a variety of other inflammatory lung disorders, including acute respiratory syndrome (ARDS), cystic fibrosis and asthma, exhibit high levels of inflammatory mediators and cells. Neutrophils accumulate in high numbers during infection and inflammation and release cathepsin G, which targets the lung epithelium. The damaged epithelial cells, in turn, release chemokines that attract more neutrophils (Hiemstra et al., *Eur. Respir. J.* 12: 1200-1208, 1998). Whereas in a murine model for lung inflammation, reduction of IL-13, a pleiotropic cytokine that is a major effector of inflammation, resulted in an associated decrease in cathepsin B (Lee et al., *J. Clin. Invest.* 116:163-173, 2006). As with lung diseases, many liver injuries involve the inflammation process. Activation of TNF-R1, the receptor for inflammatory mediator TNF-α, leads to the activation of cathepsin B (Ding et al., *J. Cell. Mol. Med.* 8:445-454, 2004).

Chronic inflammation plays an important role in Alzheimer's disease (AD), as well as other progressive neurodegenerative disorders. Microglia, the resident macrophages in the brain, release numerous proinflammatory cytokines when activated by Aβ42, a peptide associated with neuritic and vascular amyloid plaques, a pathological hallmark of AD. This Aβ42-mediated inflammatory response induces expression of cathepsin B. Cell-based studies further show that inhibition of cathepsin B leads to diminished toxic effects on primary neurons (Gan et al., *J. Biol. Chem.* 279:5565-5572, 2004). Golde et al. (*Science* 255:728-730, 1992) demonstrated that processing of the Aβ protein precursor into the active amyloidogenic derivatives occurred via the endosomal-lysosomal degradation pathway. Thereby, inhibition of the lysosomal cathepsins would inhibit amyloid plaque formation.

Atherosclerosis is an inflammatory disease that is also characterized by extensive remodeling of the extracellular matrix of the arterial wall. Macrophages, expressing cathepsins S, K, L and V, infiltrate the inflamed artery to form the atherosclerotic lesion. The abundant presence of elastolytic and collagenolytic cathepsins then weakens and ruptures the blood vessel wall (Liu et al., *Arterioscler Thromb Vasc Biol.* 24:1359-1366, 2004; Yasuda et al., *J Biol Chem* 279:36761-36770, 2004).

Thus, according to other embodiments of the invention, methods are provided for treating or preventing inflammatory diseases comprising administering to a subject an effect amount of a compound or composition described herein.

Other embodiments of the invention relate to methods for treating or preventing diseases comprising tissue remodeling or degradation. Autophagy is the cellular degradation process responsible for the turnover of unnecessary or dysfunctional organelles and cytoplasmic proteins within a cell during tissue remodeling. An increase in cathepsins B and D occurs when a cell is undergoing autophagy (Yan et al., *PNAS* 102: 13807-13812, 2005). However, in some circumstances such as muscular dystrophy, autophagy turns into excess protein catabolism resulting in the reduction in muscle proteins. In the early stages of the disease, cathepsin B is markedly increased (Takeda et al., *Biochem J.* 288: 643-648, 1992). Thereby, a cathepsin inhibitor of the invention could be used to treat or prevent muscular dystrophy, cachexia or other muscle-wasting diseases.

The skeleton is a dynamic organ which is renewed every five to seven years. The major cell types in bone tissue are osteoblasts, responsible for the synthesis of bone matrix components, and osteoclasts, the main bone-resorbing cells responsible for the physiological but also pathological degradation of the bone matrix. Cathepsin K is the major proteolytic activity in osteoclasts. Osteoporosis is characterized by bone loss and microstructural deterioration. Other conditions that also exhibit aggressive bone resorption include Paget's disease, bone fractures, abnormally increased bone turnover, osteoarthritis, perprosthetic osteolysis, osteogenesis imperfecta, metastatic bone disease, hypercalcemia of malignancy. The utility of using cathepsin inhibitors in inhibiting bone resorption is known in the literature (Votta et al., *J. Bone Miner Res.* 12:1396-1406, 1997).

Cartilage tissue shows a much slower turnover than bone. It is avascular and consists mostly of two components, triple helical type II collagen that provides tensile strength and the proteoglycan, aggrecan, that is responsible for compressive stiffness, both which are synthesized by cartilage-embedded chondrocytes. Although the collagen is highly resistant to general proteolysis, cathepsin K is capable of cleaving it at multiple sites. A major feature in many forms of arthritis, including osteoarthritis and rheumatoid arthritis, is the progressive destruction of articular cartilage. In diseased joints, lesions form, thereby initiating the inflammatory process. Ultimately, cathepsins B, L and K are released by synovial fibroblast located within the joints, resulting in cartilage degradation (Yasuda et al., *Advanced Drug Discovery Reviews* 57:973-993, 2005).

Additional embodiments of the invention relate to methods of treatment or prevention of tissue remodeling-related diseases (e.g., muscular dystrophy, bone resorption diseases and joint diseases) including administering to the subject an effective amount of a compound or composition described herein.

Cancer is a complex set of proliferative diseases that are thought to arise via multistep pathways involving inactivation of tumor suppressor proteins and activation of oncogenic peptides. Surveys of human tumors have suggested an association of certain cathepsins with malignancy (Yan et al, *Biol. Chem.* 379: 113-123, 1998; Kos et al., *Int. J. Biol. Markers* 15:84-89, 2000). Using a murine model for pancreatic islet tumors, Joyce et al. (*Cancer Cell* 5:443-453, 2004) demonstrated that cathepsin inhibitors impaired tumor growth. Furthermore, searches for prognostic molecular markers in pancreatic adenocarcinoma and breast cancer have identified cathepsin D as being upregulated (Shen et al., *Cancer Res.* 64:9018-9026, 2004; Esteva et al., *Breast Cancer Res.* 6:109-118, 2004). Other embodiments of the invention thus relate to methods for the treatment or prevention of cancer, comprising administering to a subject an effective amount of a compound or composition described herein.

In another embodiment of the invention, the disclosed compounds and compositions are used in the treatment or prevention of infections, such as viral or parasitic infections. Severe acute respiratory syndrome (SARS) is an acute respiratory illness caused by a coronavirus (SARS-CoV). SAR-CoV infection was blocked by inhibitors of cathepsin L (Simmons et al., *PNAS* 102:11876-11881, 2005). *Leishmania (L.)* are the etiological agents of a variety of disease manifestations. Both *L. donovani* and *L. chagasi* pose serious health problems in many tropical and subtropical countries. This parasite possesses a developmentally regulated cathepsin L-like cysteine protease that is expressed only in the infectious amastigote stages, which is during macrophage infection and intra-macrophage survival of the parasite (Mundodi et al., *BMC Molecular Biology* 6:3, 2005). Thus, inhibiting the L-like cathepsin could prevent or reduce the severity of an infection caused by a parasite selected from *Plasmodium* sps. (including *P. falciparum, P. vivax, P. malariae,* and *P. ovale*, which cause malaria), *Trypanosoma* sps. (including *T. cruzi*, which causes Chagas' disease, and *T. brucei* which causes African sleeping sickness), *Leishmania* sps. (including *L. amazonensis, L. donovani, L. infantum, L. mexicana,* etc.), *Pneumocystis carinii* (a protozoan known to cause pneumonia in AIDS and other immunosuppressed patients), *Toxoplasma gondii, Entamoeba histolytica, Entamoeba invadens,* and *Giardia lamblia*.

As described above, the methods of the invention may in some embodiments be used for treating or preventing cancer. Such methods may, in certain embodiments, further comprise administration of a chemotherapeutic agent. Chemotherapeutic agents that may be coadministered with pharmaceutical compositions of the instant invention include: alemtuzumab, aminoglutethimide, amsacrine, anastrozole, asparaginase, bcg, bevacizumab, bicalutamide, bleomycin, bortezomib, buserelin, busulfan, campothecin, capecitabine, carboplatin, carmustine, CeaVac, cetuximab, chlorambucil, cisplatin, cladribine, clodronate, colchicine, cyclophosphamide, cyproterone, cytarabine, dacarbazine, daclizumab, dactinomycin, daunorubicin, dienestrol, diethylstilbestrol, docetaxel, doxorubicin, edrecolomab, epirubicin, epratuzumab, erlotinib, estradiol, estramustine, etoposide, exemestane, filgrastim, fludarabine, fludrocortisone, fluorouracil, fluoxymesterone, flutamide, gemcitabine, gemtuzumab, genistein, goserelin, huJ591, hydroxyurea, ibritumomab, idarubicin, ifosfamide, IGN-101, imatinib, interferon, irinotecan, ironotecan, letrozole, leucovorin, leuprolide, levamisole, lintuzumab, lomustine, MDX-210, mechlorethamine, medroxyprogesterone, megestrol, melphalan, mercaptopurine, mesna, methotrexate, mitomycin, mitotane, mitoxantrone, mitumomab, nilutamide, nocodazole, octreotide, oxaliplatin, paclitaxel, pamidronate, pentostatin, pertuzumab, plicamycin, porfimer, procarbazine, raltitrexed, rituximab, streptozocin, sunitinib, suramin, tamoxifen, temozolomide, teniposide, testosterone, thioguanine, thiotepa, titanocene dichloride, topotecan, tositumomab, trastuzumab, tretinoin, vatalanib, vinblastine, vincristine, vindesine, and vinorelbine.

Other useful chemotherapeutic agents for combination with the compounds of the present invention include MDX-010; MAb, AME; ABX-EGF; EMD 72 000; apolizumab; labetuzumab; ior-t1; MDX-220; MRA; H-11 scFv; Oregovomab; huJ591 MAb, BZL; visilizumab; TriGem; TriAb; R3; MT-201; G-250, unconjugated; ACA-125; Onyvax-105; CDP-860; BrevaRex MAb; AR54; IMC-1C11; GlioMAb-H; ING-1; Anti-LCG MAbs; MT-103; KSB-303; Therex; KW-2871; Anti-HMI.24; Anti-PTHrP; 2C4 antibody; SGN-30; TRAIL-RI MAb, CAT; Prostate cancer antibody; H22xKi-4; ABX-MA1; Imuteran; and Monopharm-C.

These chemotherapeutic agents may be categorized by their mechanism of action into, for example, the following groups: anti-metabolites/anti-cancer agents, such as pyrimidine analogs (e.g., 5-fluorouracil, floxuridine, capecitabine, gemcitabine and cytarabine) and purine analogs, folate antagonists and related inhibitors (e.g., mercaptopurine, thioguanine, pentostatin and 2-chlorodeoxyadenosine (cladribine)); antiproliferative/antimitotic agents including natural products such as vinca alkaloids (e.g., vinblastine, vincristine, and vinorelbine), microtubule disruptors such as taxane (paclitaxel, docetaxel), vincristin, vinblastin, nocodazole, epothilones and navelbine, epidipodophyllotoxins (teniposide), DNA damaging agents (e.g., actinomycin, amsacrine, anthracyclines, bleomycin, busulfan, camptothecin, carboplatin, chlorambucil, cisplatin, cyclophosphamide, cytoxan, dactinomycin, daunorubicin, docetaxel, doxorubicin, epirubicin, hexamethylmelamineoxaliplatin, iphosphamide, melphalan, merchlorethamine, mitomycin, mitoxantrone, nitrosourea, paclitaxel, plicamycin, procarbazine, teniposide, triethylenethiophosphoramide and etoposide (VP16)); antibiotics such as dactinomycin (actinomycin D), daunorubicin, doxorubicin (adriamycin), idarubicin, anthracyclines, mitoxantrone, bleomycins, plicamycin (mithramycin) and mitomycin; enzymes (e.g., L-asparaginase, which systemically metabolizes L-asparagine and deprives cells which do not have the capacity to synthesize their own asparagine); antiplatelet agents; antiproliferative/antimitotic alkylating agents such as nitrogen mustards (e.g., mechlorethamine, cyclophosphamide and analogs, melphalan, chlorambucil), ethylenimines and methylmelamines (e.g., hexamethylmelamine and thiotepa), alkyl sulfonates—busulfan, nitrosoureas (e.g., carmustine (BCNU) and analogs, streptozocin), trazenes—dacarbazinine (DTIC); antiproliferative/antimitotic antimetabolites such as folic acid analogs (e.g., methotrexate); platinum coordination complexes (e.g., cisplatin, carboplatin), procarbazine, hydroxyurea, mitotane, aminoglutethimide; hormones, hormone analogs (e.g., estrogen, tamoxifen, goserelin, bicalutamide, nilutamide) and aromatase inhibitors (e.g., letrozole, anastrozole); anticoagulants (e.g., heparin, synthetic heparin salts and other inhibitors of thrombin); fibrinolytic agents (such as tissue plasminogen activator, streptokinase and urokinase), aspirin, COX-2 inhibitors, dipyridamole, ticlopidine, clopidogrel, abciximab; antimigratory agents; antisecretory agents (e.g., breveldin); immunosuppressives (e.g., cyclosporine, tacrolimus (FK-506), sirolimus (rapamycin), azathioprine, mycophenolate mofetil); anti-angiogenic compounds (e.g., TNP-470, genistein) and growth factor inhibitors (e.g., vascular endothelial growth factor (VEGF) inhibitors, fibroblast growth factor (FGF) inhibitors, epidermal growth factor (EGF) inhibitors); angiotensin receptor blocker; nitric oxide donors; anti-sense oligonucleotides; antibodies (e.g., trastuzumab and others listed above); cell cycle inhibitors and differentiation inducers (e.g., tretinoin); mTOR inhibitors, topoisomerase inhibitors (e.g., doxorubicin (adriamycin), amsacrine, camptothecin, daunorubicin, dactinomycin, eniposide, epirubicin, etoposide, idarubicin, irinotecan (CPT-11) and mitoxantrone, topotecan, irinotecan), corticosteroids (e.g., cortisone, dexamethasone, hydrocortisone, methylpednisolone, prednisone, and prenisolone); growth factor signal transduction kinase inhibitors; mitochondrial dysfunction inducers and caspase activators; chromatin disruptors.

The pharmaceutical compositions of the instant invention may be coadministered with chemotherapeutic agents either singly or in combination. Many combinatorial therapies have been developed, including but not limited to those listed in Table 3.

TABLE 3

Exemplary combinatorial therapies for the treatment of cancer.

| Name | Therapeutic agents |
| --- | --- |
| ABV | Doxorubicin, Bleomycin, Vinblastine |
| ABVD | Doxorubicin, Bleomycin, Vinblastine, Dacarbazine |
| AC (Breast) | Doxorubicin, Cyclophosphamide |
| AC (Sarcoma) | Doxorubicin, Cisplatin |
| AC (Neuroblastoma) | Cyclophosphamide, Doxorubicin |
| ACE | Cyclophosphamide, Doxorubicin, Etoposide |
| ACe | Cyclophosphamide, Doxorubicin |
| AD | Doxorubicin, Dacarbazine |
| AP | Doxorubicin, Cisplatin |
| ARAC-DNR | Cytarabine, Daunorubicin |
| B-CAVe | Bleomycin, Lomustine, Doxorubicin, Vinblastine |
| BCVPP | Carmustine, Cyclophosphamide, Vinblastine, Procarbazine, Prednisone |
| BEACOPP | Bleomycin, Etoposide, Doxorubicin, Cyclophosphamide, Vincristine, Procarbazine, Prednisone, Filgrastim |
| BEP | Bleomycin, Etoposide, Cisplatin |
| BIP | Bleomycin, Cisplatin, Ifosfamide, Mesna |
| BOMP | Bleomycin, Vincristine, Cisplatin, Mitomycin |
| CA | Cytarabine, Asparaginase |
| CABO | Cisplatin, Methotrexate, Bleomycin, Vincristine |
| CAF | Cyclophosphamide, Doxorubicin, Fluorouracil |
| CAL-G | Cyclophosphamide, Daunorubicin, Vincristine, Prednisone, Asparaginase |
| CAMP | Cyclophosphamide, Doxorubicin, Methotrexate, Procarbazine |
| CAP | Cyclophosphamide, Doxorubicin, Cisplatin |
| CaT | Carboplatin, Paclitaxel |
| CAV | Cyclophosphamide, Doxorubicin, Vincristine |
| CAVE ADD | CAV and Etoposide |

TABLE 3-continued

Exemplary combinatorial therapies for the treatment of cancer.

| Name | Therapeutic agents |
|---|---|
| CA-VP16 | Cyclophosphamide, Doxorubicin, Etoposide |
| CC | Cyclophosphamide, Carboplatin |
| CDDP/VP-16 | Cisplatin, Etoposide |
| CEF | Cyclophosphamide, Epirubicin, Fluorouracil |
| CEPP(B) | Cyclophosphamide, Etoposide, Prednisone, with or without/Bleomycin |
| CEV | Cyclophosphamide, Etoposide, Vincristine |
| CF | Cisplatin, Fluorouracil or Carboplatin Fluorouracil |
| CHAP | Cyclophosphamide or Cyclophosphamide, Altretamine, Doxorubicin, Cisplatin |
| ChlVPP | Chlorambucil, Vinbiastine, Procarbazine, Prednisone |
| CHOP | Cyclophosphamide, Doxorubicin, Vincristine, Prednisone |
| CHOP-BLEO | Add Bleomycin to CHOP |
| CISCA | Cyclophosphamide, Doxorubicin, Cisplatin |
| CLD-BOMP | Bleomycin, Cisplatin, Vincristine, Mitomycin |
| CMF | Methotrexate, Fluorouracil, Cyclophosphamide |
| CMFP | Cyclophosphamide, Methotrexate, Fluorouracil, Prednisone |
| CMFVP | Cyclophosphamide, Methotrexate, Fluorouracil, Vincristine, Prednisone |
| CMV | Cisplatin, Methotrexate, Vinblastine |
| CNF | Cyclophosphamide, Mitoxantrone, Fluorouracil |
| CNOP | Cyclophosphamide, Mitoxantrone, Vincristine, Prednisone |
| COB | Cisplatin, Vincristine, Bleomycin |
| CODE | Cisplatin, Vincristine, Doxorubicin, Etoposide |
| COMLA | Cyclophosphamide, Vincristine, Methotrexate, Leucovorin, Cytarabine |
| COMP | Cyclophosphamide, Vincristine, Methotrexate, Prednisone |
| Cooper Regimen | Cyclophosphamide, Methotrexate, Fluorouracil, Vincristine, Prednisone |
| COP | Cyclophosphamide, Vincristine, Prednisone |
| COPE | Cyclophosphamide, Vincristine, Cisplatin, Etoposide |
| COPP | Cyclophosphamide, Vincristine, Procarbazine, Prednisone |
| CP(Chronic lymphocytic leukemia) | Chlorambucil, Prednisone |
| CP (Ovarian Cancer) | Cyclophosphamide, Cisplatin |
| CT | Cisplatin, Paclitaxel |
| CVD | Cisplatin, Vinblastine, Dacarbazine |
| CVI | Carboplatin, Etoposide, Ifosfamide, Mesna |
| CVP | Cyclophosphamide, Vincristine, Prednisome |
| CVPP | Lomustine, Procarbazine, Prednisone |
| CYVADIC | Cyclophosphamide, Vincristine, Doxorubicin, Dacarbazine |
| DA | Daunorubicin, Cytarabine |
| DAT | Daunorubicin, Cytarabine, Thioguanine |
| DAV | Daunorubicin, Cytarabine, Etoposide |
| DCT | Daunorubicin, Cytarabine, Thioguanine |
| DHAP | Cisplatin, Cytarabine, Dexamethasone |
| DI | Doxorubicin, Ifosfamide |
| DTIC/Tamoxifen | Dacarbazine, Tamoxifen |
| DVP | Daunorubicin, Vincristine, Prednisone |
| EAP | Etoposide, Doxorubicin, Cisplatin |
| EC | Etoposide, Carboplatin |
| EFP | Etoposie, Fluorouracil, Cisplatin |
| ELF | Etoposide, Leucovorin, Fluorouracil |
| EMA 86 | Mitoxantrone, Etoposide, Cytarabine |
| EP | Etoposide, Cisplatin |
| EVA | Etoposide, Vinblastine |
| FAC | Fluorouracil, Doxorubicin, Cyclophosphamide |
| FAM | Fluorouracil, Doxorubicin, Mitomycin |
| FAMTX | Methotrexate, Leucovorin, Doxorubicin |
| FAP | Fluorouracil, Doxorubicin, Cisplatin |
| F-CL | Fluorouracil, Leucovorin |
| FEC | Fluorouracil, Cyclophosphamide, Epirubicin |
| FED | Fluorouracil, Etoposide, Cisplatin |
| FL | Flutamide, Leuprolide |
| FZ | Flutamide, Goserelin acetate implant |
| HDMTX | Methotrexate, Leucovorin |
| Hexa-CAF | Altretamine, Cyclophosphamide, Methotrexate, Fluorouracil |
| ICE-T | Ifosfamide, Carboplatin, Etoposide, Paclitaxel, Mesna |
| IDMTX/6-MP | Methotrexate, Mercaptopurine, Leucovorin |
| IE | Ifosfamide, Etoposie, Mesna |
| IfoVP | Ifosfamide, Etoposide, Mesna |
| IPA | Ifosfamide, Cisplatin, Doxorubicin |
| M-2 | Vincristine, Carmustine, Cyclophosphamide, Prednisone, Melphalan |
| MAC-III | Methotrexate, Leucovorin, Dactinomycin, Cyclophosphamide |
| MACC | Methotrexate, Doxorubicin, Cyclophosphamide, Lomustine |
| MACOP-B | Methotrexate, Leucovorin, Doxorubicin, Cyclophosphamide, Vincristine, Bleomycin, Prednisone |
| MAID | Mesna, Doxorubicin, Ifosfamide, Dacarbazine |
| m-BACOD | Bleomycin, Doxorubicin, Cyclophosphamide, Vincristine, Dexamethasone, Methotrexate, Leucovorin |
| MBC | Methotrexate, Bleomycin, Cisplatin |
| MC | Mitoxantrone, Cytarabine |
| MF | Methotrexate, Fluorouracil, Leucovorin |
| MICE | Ifosfamide, Carboplatin, Etoposide, Mesna |
| MINE | Mesna, Ifosfamide, Mitoxantrone, Etoposide |
| mini-BEAM | Carmustine, Etoposide, Cytarabine, Melphalan |
| MOBP | Bleomycin, Vincristine, Cisplatin, Mitomycin |
| MOP | Mechlorethamine, Vincristine, Procarbazine |
| MOPP | Mechlorethamine, Vincristine, Procarbazine, Prednisone |
| MOPP/ABV | Mechlorethamine, Vincristine, Procarbazine, Prednisone, Doxorubicin, Bleomycin, Vinblastine |
| MP (multiple myeloma) | Melphalan, Prednisone |
| MP (prostate cancer) | Mitoxantrone, Prednisone |
| MTX/6-MO | Methotrexate, Mercaptopurine |
| MTX/6-MP/VP | Methotrexate, Mercaptopurine, Vincristine, Prednisone |
| MTX-CDDPAdr | Methotrexate, Leucovorin, Cisplatin, Doxorubicin |
| MV (breast cancer) | Mitomycin, Vinblastine |
| MV (acute myelocytic leukemia) | Mitoxantrone, Etoposide |
| M-VAC Methotrexate | Vinblastine, Doxorubicin, Cisplatin |
| MVP Mitomycin | Vinblastine, Cisplatin |
| MVPP | Mechlorethamine, Vinblastine, Procarbazine, Prednisone |
| NFL | Mitoxantrone, Fluorouracil, Leucovorin |
| NOVP | Mitoxantrone, Vinblastine, Vincristine |
| OPA | Vincristine, Prednisone, Doxorubicin |
| OPPA | Add Procarbazine to OPA. |
| PAC | Cisplatin, Doxorubicin |
| PAC-I | Cisplatin, Doxorubicin, Cyclophosphamide |
| PA-CI | Cisplatin, Doxorubicin |
| PC | Paclitaxel, Carboplatin or Paclitaxel, Cisplatin |
| PCV | Lomustine, Procarbazine, Vincristine |
| PE | Paclitaxel, Estramustine |
| PFL | Cisplatin, Fluorouracil, Leucovorin |
| POC | Prednisone, Vincristine, Lomustine |
| ProMACE | Prednisone, Methotrexate, Leucovorin, Doxorubicin, Cyclophosphamide, Etoposide |
| ProMACE/cytaBOM | Prednisone, Doxorubicin, Cyclophosphamide, Etoposide, Cytarabine, Bleomycin, Vincristine, Methotrexate, Leucovorin, Cotrimoxazole |
| PRoMACE/MOPP | Prednisone, Doxorubicin, Cyclophosphamide, Etoposide, Mechlorethamine, Vincristine, Procarbazine, Methotrexate, Leucovorin |
| Pt/VM | Cisplatin, Teniposide |
| PVA | Prednisone, Vincristine, Asparaginase |
| PVB | Cisplatin, Vinblastine, Bleomycin |
| PVDA | Prednisone, Vincristine, Daunorubicin, Asparaginase |
| SMF | Streptozocin, Mitomycin, Fluorouracil |
| TAD | Mechlorethamine, Doxorubicin, Vinblastine, Vincristine, Bleomycin, Etoposide, Prednisone |

TABLE 3-continued

Exemplary combinatorial therapies for the treatment of cancer.

| Name | Therapeutic agents |
|---|---|
| TCF | Paclitaxel, Cisplatin, Fluorouracil |
| TIP | Paclitaxel, Ifosfamide, Mesna, Cisplatin |
| TTT | Methotrexate, Cytarabine, Hydrocortisone |
| Topo/CTX | Cyclophosphamide, Topotecan, Mesna |
| VAB-6 | Cyclophosphamide, Dactinomycin, Vinblastine, Cisplatin, Bleomycin |
| VAC | Vincristine, Dactinomycin, Cyclophosphamide |
| VACAdr | Vincristine, Cyclophosphamide, Doxorubicin, Dactinomycin, Vincristine |
| VAD | Vincristine, Doxorubicin, Dexamethasone |
| VATH | Vinblastine, Doxorubicin, Thiotepa, Flouxymesterone |
| VBAP | Vincristine, Carmustine, Doxorubicin, Prednisone |
| VBCMP | Vincristine, Carmustine, Melphalan, Cyclophosphamide, Prednisone |
| VC | Vinorelbine, Cisplatin |
| VCAP | Vincristine, Cyclophosphamide, Doxorubicin, Prednisone |
| VD | Vinorelbine, Doxorubicin |
| VelP | Vinblastine, Cisplatin, Ifosfamide, Mesna |
| VIP | Etoposide, Cisplatin, Ifosfamide, Mesna |
| VM | Mitomycin, Vinblastine |
| VMCP | Vincristine, Melphalan, Cyclophosphamide, Prednisone |
| VP | Etoposide, Cisplatin |
| V-TAD | Etoposide, Thioguanine, Daunorubicin, Cytarabine |
| 5 + 2 | Cytarabine, Daunorubicin, Mitoxantrone |
| 7 + 3 | Cytarabine with/, Daunorubicin or Idarubicin or Mitoxantrone |
| "8 in 1" | Methylprednisolone, Vincristine, Lomustine, Procarbazine, Hydroxyurea, Cisplatin, Cytarabine, Dacarbazine |

In addition to conventional chemotherapeutics, the epoxide inhibitors described herein may also be used with antisense RNA, RNAi, or other polynucleotides to inhibit the expression of the cellular components that contribute to unwanted cellular proliferation that are targets of conventional chemotherapy. Such targets are, merely to illustrate, growth factors, growth factor receptors, cell cycle regulatory proteins, transcription factors, or signal transduction kinases.

Combination therapies comprising the epoxide inhibitors of the instant invention and a conventional chemotherapeutic agent may be advantageous over combination therapies known in the art because the combination allows the conventional chemotherapeutic agent to exert greater effect at lower dosage. In a specific embodiment, the effective dose ($ED_{50}$) for a chemotherapeutic agent, or combination of conventional chemotherapeutic agents, when used in combination with an epoxide inhibitor of the instant invention is at least 2 fold less than the $ED_{50}$ for the chemotherapeutic agent alone, and even more preferably at 5-fold, 10-fold, or even 25-fold less. Conversely, the therapeutic index (TI) for such chemotherapeutic agent or combination of such chemotherapeutic agent when used in combination with an epoxide inhibitor of the instant invention can be at least 2-fold greater than the TI for conventional chemotherapeutic regimen alone, and even more preferably at 5-fold, 10-fold, or even 25-fold greater.

It will be readily apparent to one of ordinary skill in the relevant arts that other suitable modifications and adaptations to the methods and applications described herein may be made without departing from the scope of the invention or any embodiment thereof. Having now described the present invention in detail, the same will be more clearly understood by reference to the following Examples, which are included herewith for purposes of illustration only and are not intended to be limiting of the invention.

EXAMPLES

Structure and Function of Epoxide Inhibitors

Examples of compounds that have been synthesized according to the above scheme, or by similar methods, are shown in Table 4. Also included in the table for comparison are known compounds JPMOEt and JPMOH (also known as JPM-565). See Meara and Rich, *J. Med. Chem.* 39:3357-3366, 1996; Bogyo et al, *Chem. Biol.* 7:27-38, 2000; and Joyce et al., *Cancer Cell* 5:443-453, 2004. The table also lists cathepsin targets and measured $IC_{50}$ values for specific compounds. To determine these values, 1 mg/ml of rat liver lysate was incubated with a series of concentrations of the inhibitor for 20 minutes. Then, 1 ul of a radiolabled general cathepsin probe, DCG-04, was added to the solutions and incubated for 1 hour. After fixing and drying the gel, the residual enzyme activity was measured using ImageJ software. The measurements were then transferred to GraphPad Prism 4 to calculate the $IC_{50}$ values.

Three compound libraries were synthesized in which the $R_1$ position was varied through a series of 19 amines. (The structures of the amines used are shown above in Table 1.) Three libraries were constructed in which the $R_2$ position was leucine, 4-methyl-phenylalanine, or nitro-tyrosine. The $R_3$ positions in the first libraries were either tyrosine or Ig1 (see Table 2). Most of the compounds in the initial libraries used to identify lead compounds were synthesized using a standard amide linkage to a Rink resin and therefore contained an amide at $R_3$. One library of compounds in which $R_1$ was tyramine and $R_2$ was leucine was used to scan $R_3$ with the set of 19 amines. These compounds were synthesized as shown in the scheme above and contain no amide at $R_3$. Briefly, Rink resin was suspended in DMF for 15 minutes. Fmoc deprotection of the resin was achieved with 20% piperidine in DMF for 20 minutes. Subsequently, the resin was washed with DMF (3×). The desired amino acid (3 eq), DIC (3 eq) and HOBt (3 eq) were dissolved in DMF (at 0.4 M) and added to the resin. Resin was shaken for 1.5 hours followed by washing with DMF (3×) and DCM (3×). The above steps were repeated to elongate the desired peptide sequence of the molecule. After deprotection of the last residue, the resin was reacted with ethyl-(p-nitrophenyl)-oxirane-2,3-dicarboxylate (2S,3S) or (2R,3R) conformations (3 eq.; 0.4 M in DMF) for a 1.5 hour. Next, resin was suspended in THF for 15 minutes, solvent was drained and a 1:4 solution of 1M KOH in ethanol and THF was added. The resin was reacted for 1 hour, after which the solvent was drained. The resin was washed with 1% acetic acid in ethanol, ethanol (3×) and DCM (3×). A 0.4M solution of the desired amine (3 eq), PyBop (3 eq) and DIEA (6 eq) was then added to the resin. The reaction mixture was shaken for 1.5 hours. To cleave the product from the resin, the resin was incubated in 95/2.5/2.5 solution of TFA/water/TIS for 1 hour. The resulting solution was then collected, concentrated under reduced pressure and the residue was subjected to HPLC purification.

TABLE 4

Examples of structure and activity of epoxide inhibitors.

| Cpd # | Structure | Target | IC$_{50}$, CatZ (μM) | IC$_{50}$, CatB (μM) | IC$_{50}$, CatH (μM) | IC$_{50}$, CatC (μM) | Exp. mass (M + H)$^+$ | Actual mass (M + H)$^+$ |
|---|---|---|---|---|---|---|---|---|
| JPMOEt | 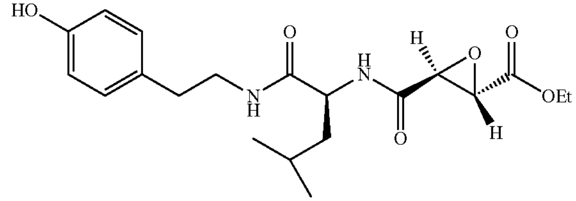 [SMILES: CCOC(=O)[C@H]1O[C@@H]1C(=O)N[C@@H](CC(C)C)C(=O)NCCc1ccc(O)cc1] | General | 0.2 | 0.04 | 4.65 | 8.9 | | |
| JPMOH | 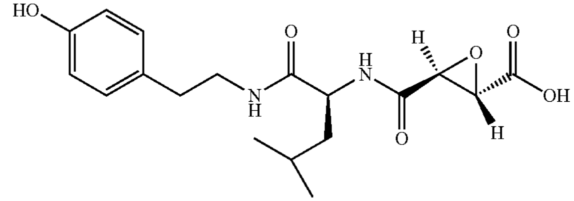 [SMILES: CC(C)C[C@H](NC(=O)[C@H]1O[C@@H]1C(=O)O)C(=O)NCCc1ccc(O)cc1] | General | 0.1 | 0.4 | 0.58 | 1 | | |
| 1 | 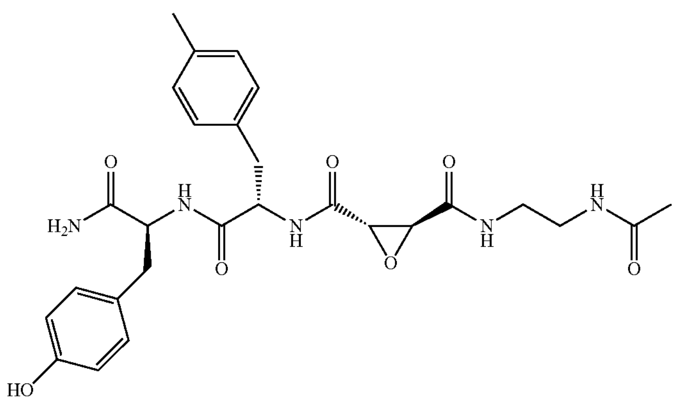 [SMILES: CC(=O)NCCNC(=O)[C@H]1O[C@@H]1C(=O)N[C@@H](Cc1ccc(C)cc1)C(=O)N[C@@H](Cc1ccc(O)cc1)C(N)=O] | Cat B | | | | | 540.2 | 540.5 |

TABLE 4-continued

Examples of structure and activity of epoxide inhibitors.

| Cpd # | Structure | Target | IC$_{50}$, CatZ (μM) | IC$_{50}$, CatB (μM) | IC$_{50}$, CatH (μM) | IC$_{50}$, CatC (μM) | Exp. mass (M + H)$^+$ | Actual mass (M + H)$^+$ |
|---|---|---|---|---|---|---|---|---|
| 2 | 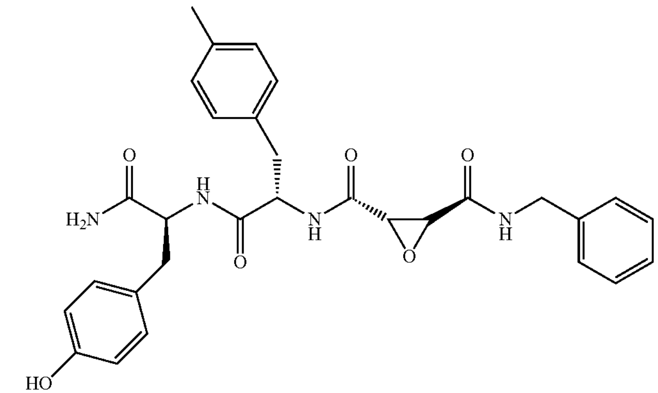 | Cat B | | | | | 545.2 | 545.4 |
| 3 | 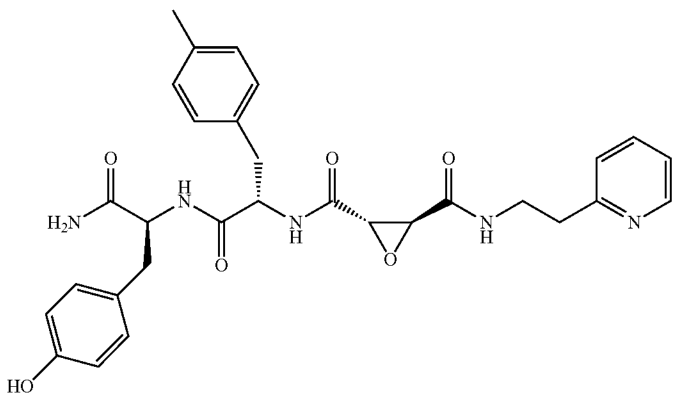 [SMILES: Cc1ccc(C[C@H](NC(=O)[C@H]2O[C@@H]2C(=O)NCCc2ccccn2)C(=O)N[C@@H](Cc2ccc(O)cc2)C(N)=O)cc1] | Cat B | | | | | 560.2 | 560.3 |

TABLE 4-continued
Examples of structure and activity of epoxide inhibitors.
| Cpd # | Structure | Target | IC$_{50}$, CatZ (μM) | IC$_{50}$, CatB (μM) | IC$_{50}$, CatH (μM) | IC$_{50}$, CatC (μM) | Exp. mass (M + H)$^+$ | Actual mass (M + H)$^+$ |
|---|---|---|---|---|---|---|---|---|
| 4 | 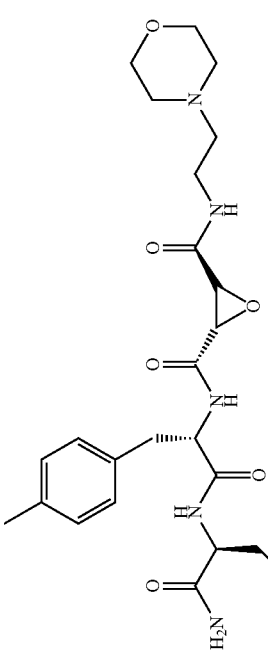 | Cat B | | | | | 568.3 | 568.5 |
| 5 | 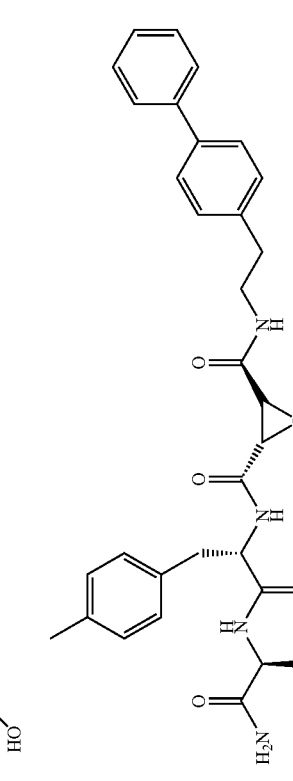 | Cat B | | | | | 635.3 | 635.6 |

TABLE 4-continued

Examples of structure and activity of epoxide inhibitors.

| Cpd # | Structure | Target | IC$_{50}$, CatZ (μM) | IC$_{50}$, CatB (μM) | IC$_{50}$, CatH (μM) | IC$_{50}$, CatC (μM) | Exp. mass (M + H)$^+$ | Actual mass (M + H)$^+$ |
|---|---|---|---|---|---|---|---|---|
| 6 | 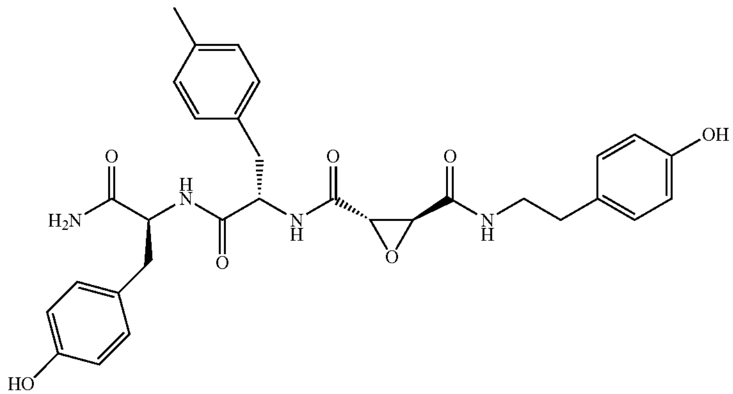 [SMILES: Cc1ccc(C[C@H](NC(=O)[C@H]2O[C@@H]2C(=O)NCCc2ccc(O)cc2)C(=O)N[C@@H](Cc2ccc(O)cc2)C(N)=O)cc1] | Cat B | | | | | 575.2 | 575.3 |
| 7 | 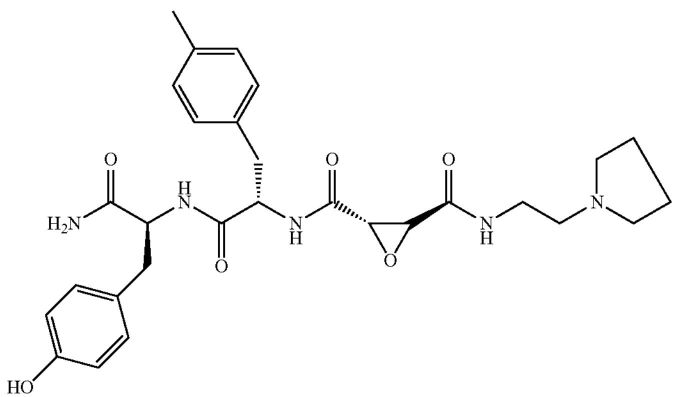 | Cat B | | | | | 552.3 | 552.5 |

TABLE 4-continued
Examples of structure and activity of epoxide inhibitors.
| Cpd # | Structure | Target | IC$_{50}$, CatZ (μM) | IC$_{50}$, CatB (μM) | IC$_{50}$, CatH (μM) | IC$_{50}$, CatC (μM) | Exp. mass (M + H)$^+$ | Actual mass (M + H)$^+$ |
|---|---|---|---|---|---|---|---|---|
| 8 | 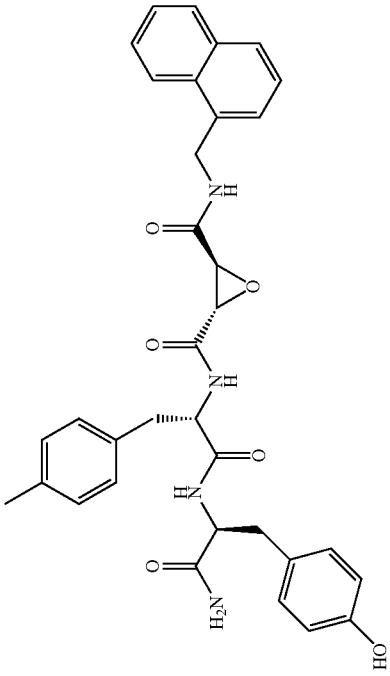 | Cat B | | | | | 595.2 | 595.5 |
| 9 | 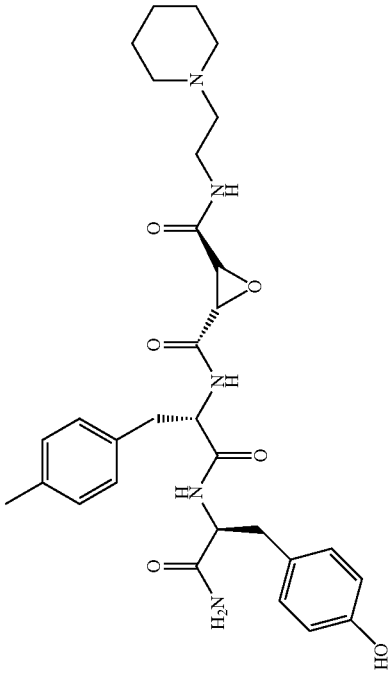 | Cat B | | | | | 566.3 | 566.5 |

TABLE 4-continued

Examples of structure and activity of epoxide inhibitors.

| Cpd # | Structure | Target | IC$_{50}$, CatZ (μM) | IC$_{50}$, CatB (μM) | IC$_{50}$, CatH (μM) | IC$_{50}$, CatC (μM) | Exp. mass (M + H)$^+$ | Actual mass (M + H)$^+$ |
|---|---|---|---|---|---|---|---|---|
| 10 | 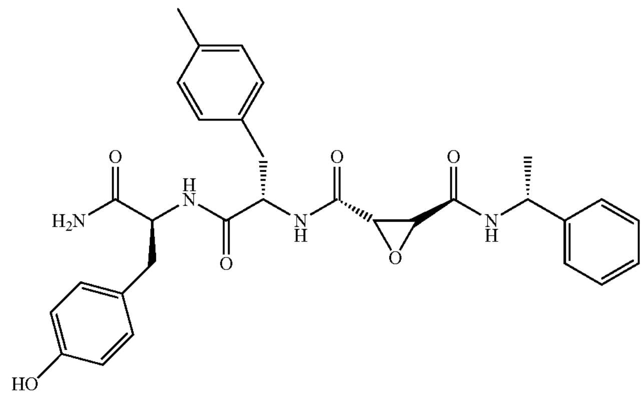 | Cat B | | | | | 559.2 | 559.5 |
| 11 | 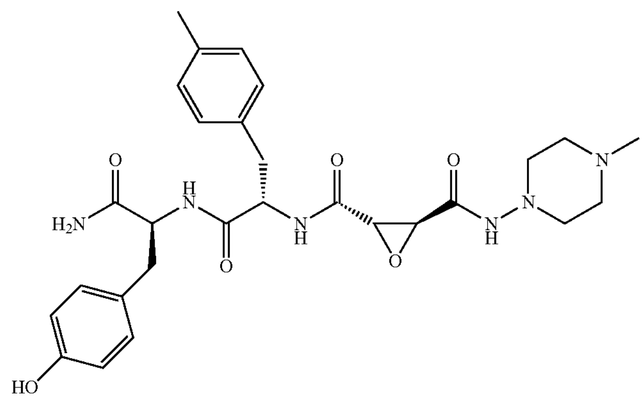 | Cat B | | | | | 553.3 | 553.6 |

TABLE 4-continued

Examples of structure and activity of epoxide inhibitors.

| Cpd # | Structure | Target | IC$_{50}$, CatZ (μM) | IC$_{50}$, CatB (μM) | IC$_{50}$, CatH (μM) | IC$_{50}$, CatC (μM) | Exp. mass (M + H)$^+$ | Actual mass (M + H)$^+$ |
|---|---|---|---|---|---|---|---|---|
| 12 | 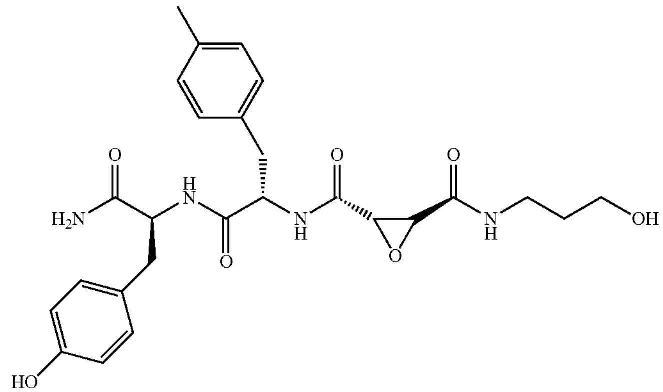 | Cat B | | | | | 513.2 | 513.5 |
| 13 | 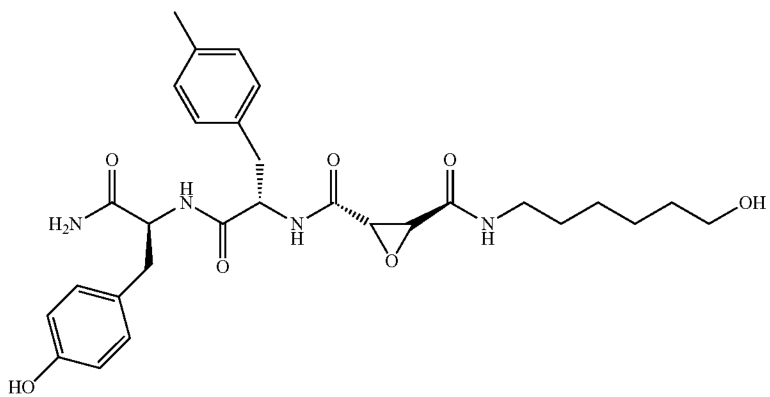 | Cat B | | | | | 555.3 | 555.5 |

TABLE 4-continued

Examples of structure and activity of epoxide inhibitors.

| Cpd # | Structure | Target | IC$_{50}$, CatZ (μM) | IC$_{50}$, CatB (μM) | IC$_{50}$, CatH (μM) | IC$_{50}$, CatC (μM) | Exp. mass (M + H)$^+$ | Actual mass (M + H)$^+$ |
|---|---|---|---|---|---|---|---|---|
| 14 | 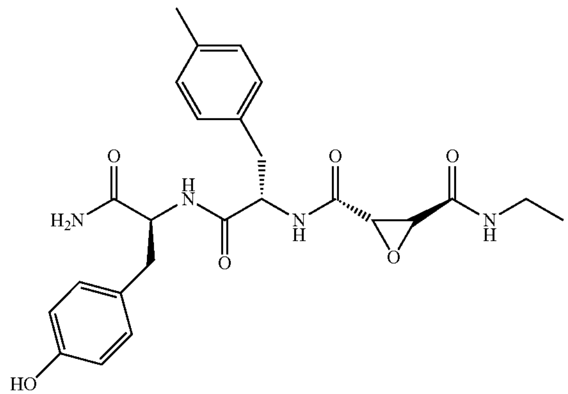 | Cat B | | | | | 483.2 | 483.3 |
| 15 | 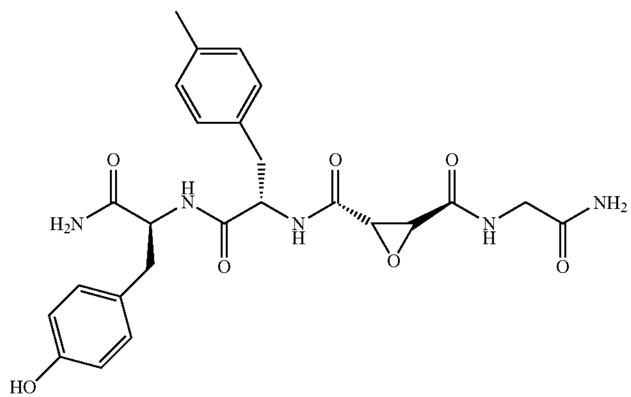 | Cat B | | | | | 512.2 | 512.6 |

TABLE 4-continued
Examples of structure and activity of epoxide inhibitors.
| Cpd # | Structure | Target | IC$_{50}$, CatZ (μM) | IC$_{50}$, CatB (μM) | IC$_{50}$, CatH (μM) | IC$_{50}$, CatC (μM) | Exp. mass (M + H)$^+$ | Actual mass (M + H)$^+$ |
|---|---|---|---|---|---|---|---|---|
| 16 | 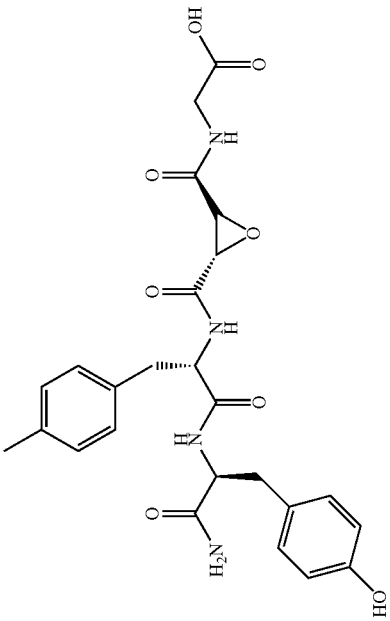 | Cat Z[1] | 0.1 | 10 | >10 | >10 | 513.2 | 513.3 |
| 17 | 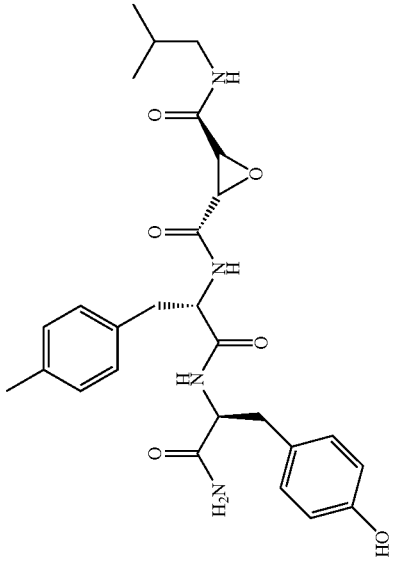 | Cat B | | | | | | |

TABLE 4-continued

Examples of structure and activity of epoxide inhibitors.

| Cpd # | Structure | Target | IC$_{50}$, CatZ (μM) | IC$_{50}$, CatB (μM) | IC$_{50}$, CatH (μM) | IC$_{50}$, CatC (μM) | Exp. mass (M + H)$^+$ | Actual mass (M + H)$^+$ |
|---|---|---|---|---|---|---|---|---|
| 18 | 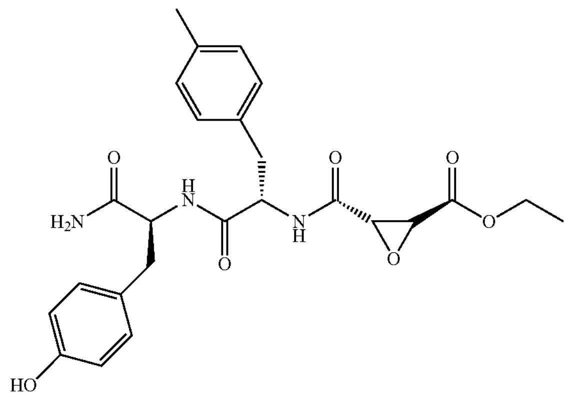 | Cat B | | | | | | |
| 19 | 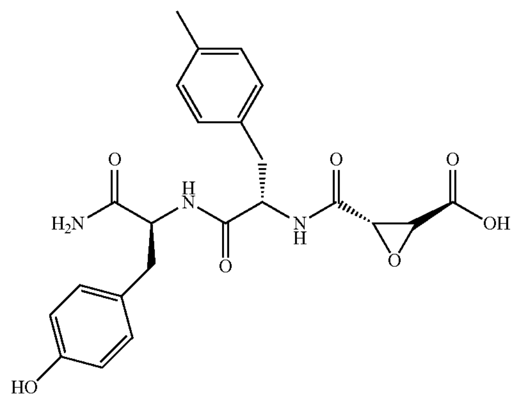 | Cat B | | | | | | |

TABLE 4-continued

Examples of structure and activity of epoxide inhibitors.

| Cpd # | Structure | Target | IC$_{50}$, CatZ (µM) | IC$_{50}$, CatB (µM) | IC$_{50}$, CatH (µM) | IC$_{50}$, CatC (µM) | Exp. mass (M + H)$^+$ | Actual mass (M + H)$^+$ |
|---|---|---|---|---|---|---|---|---|
| 20 | 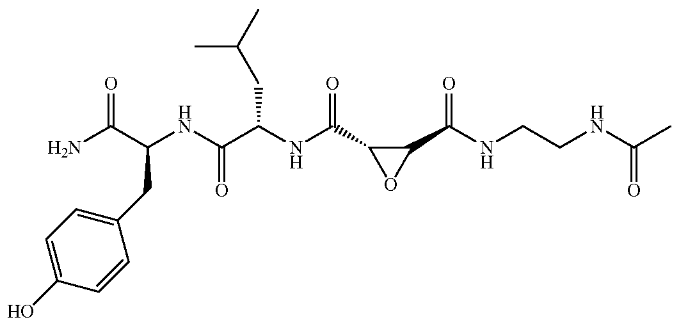 | Cat B | | | | | 492.2 | 492.3 |
| 21 | 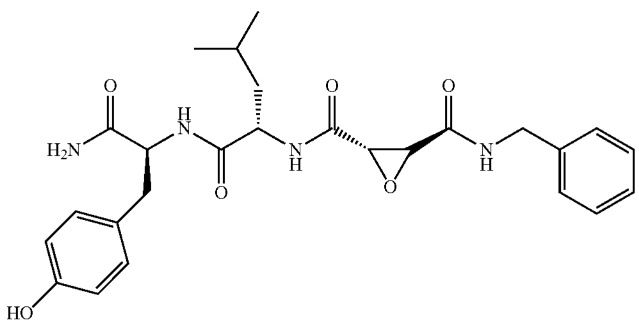 | Cat B | | | | | 497.2 | 497.4 |
| 22 | 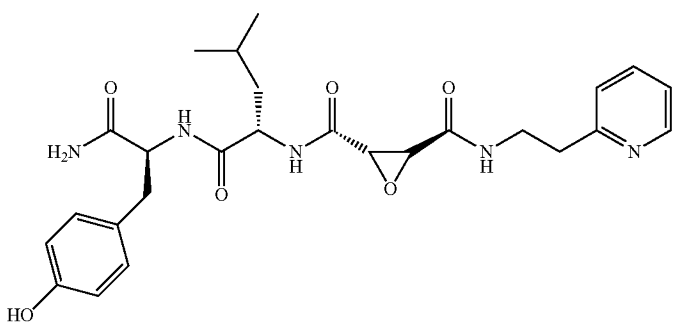 | Cat B | | | | | 512.2 | 512.5 |

TABLE 4-continued

Examples of structure and activity of epoxide inhibitors.

| Cpd # | Structure | Target | IC$_{50}$, CatZ (μM) | IC$_{50}$, CatB (μM) | IC$_{50}$, CatH (μM) | IC$_{50}$, CatC (μM) | Exp. mass (M + H)$^+$ | Actual mass (M + H)$^+$ |
|---|---|---|---|---|---|---|---|---|
| 23 | 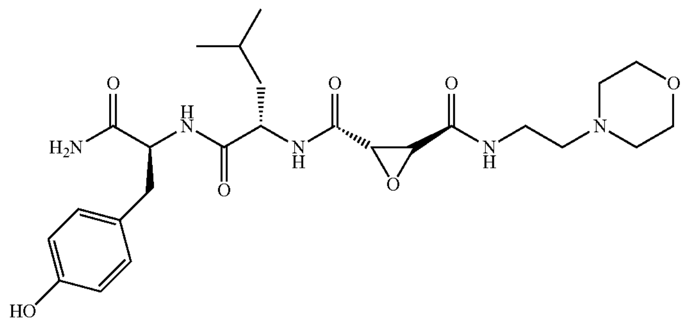 | Cat B | | | | | 520.3 | 520.3 |
| 24 | 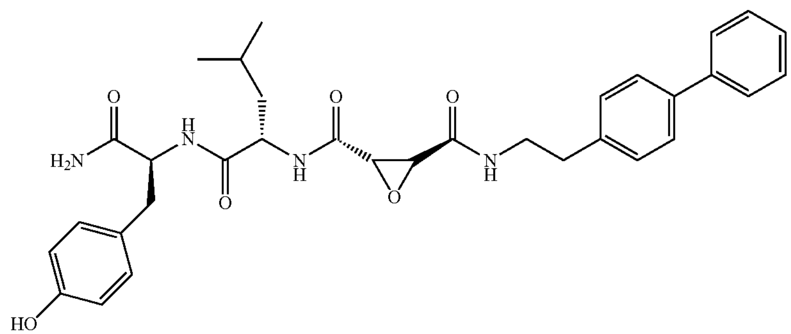 | Cat B | | | | | | |
| 25 | 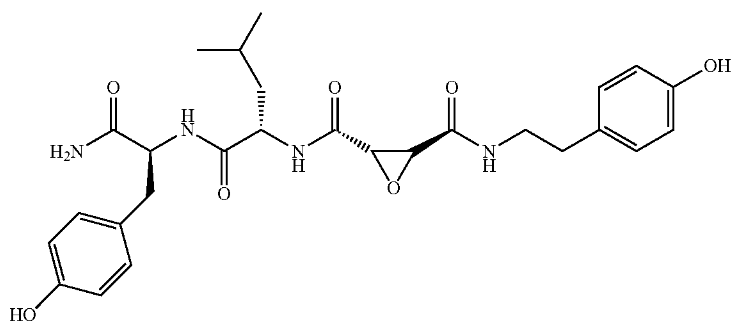 | Cat B | >10 | 0.02 | 21 | 11 | | |

TABLE 4-continued

Examples of structure and activity of epoxide inhibitors.

| Cpd # | Structure | Target | IC$_{50}$, CatZ (µM) | IC$_{50}$, CatB (µM) | IC$_{50}$, CatH (µM) | IC$_{50}$, CatC (µM) | Exp. mass (M + H)$^+$ | Actual mass (M + H)$^+$ |
|---|---|---|---|---|---|---|---|---|
| 26 | 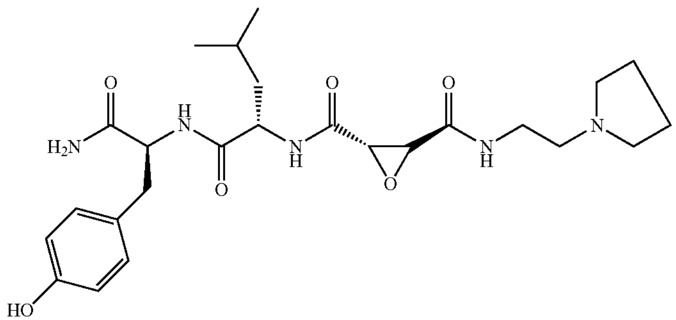 | Cat B | | | | | | |
| 27 | 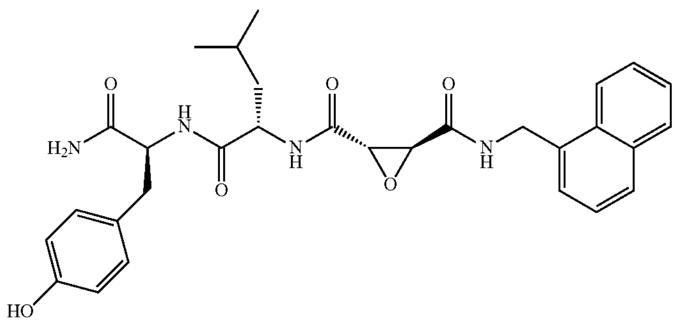 [SMILES: CC(C)C[C@H](NC(=O)[C@H]1O[C@@H]1C(=O)NCc1cccc2ccccc12)C(=O)N[C@@H](Cc1ccc(O)cc1)C(N)=O] | Cat B | | | | | 547.2 | 547.5 |
| 28 | 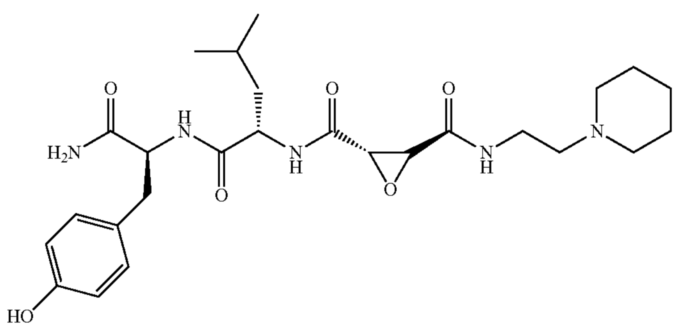 | Cat B | | | | | 518.3 | 518.5 |

TABLE 4-continued
Examples of structure and activity of epoxide inhibitors.
| Cpd # | Structure | Target | IC$_{50}$, CatZ (μM) | IC$_{50}$, CatB (μM) | IC$_{50}$, CatH (μM) | IC$_{50}$, CatC (μM) | Exp. mass (M + H)$^+$ | Actual mass (M + H)$^+$ |
|---|---|---|---|---|---|---|---|---|
| 29 | 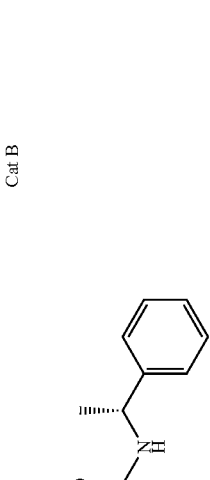 | Cat B | | | | | 511.2 | 511.3 |
| 30 | 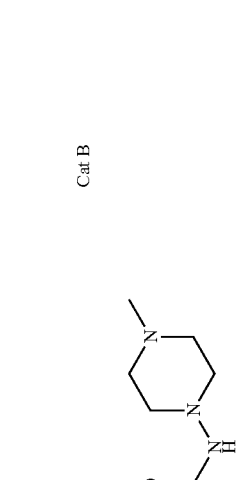 | Cat B | | | | | | |
| 31 | 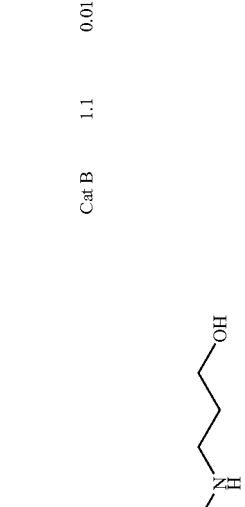 | Cat B | 1.1 | 0.01 | 5.45 | 11 | | |

TABLE 4-continued

Examples of structure and activity of epoxide inhibitors.

| Cpd # | Structure | Target | IC$_{50}$, CatZ (μM) | IC$_{50}$, CatB (μM) | IC$_{50}$, CatH (μM) | IC$_{50}$, CatC (μM) | Exp. mass (M + H)$^+$ | Actual mass (M + H)$^+$ |
|---|---|---|---|---|---|---|---|---|
| 32 | 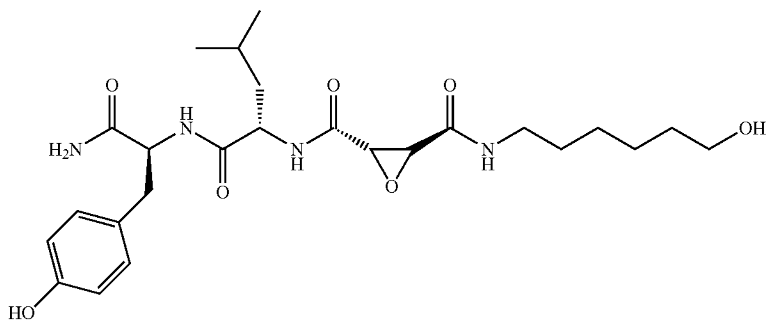 | Cat B | | | | | 507.3 | 507.3 |
| 33 | 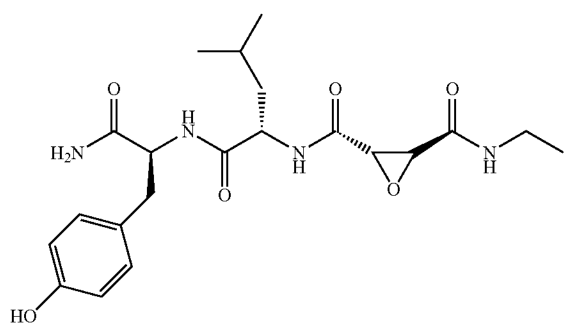 | Cat B | | | | | 435.2 | 435.3 |
| 34 | 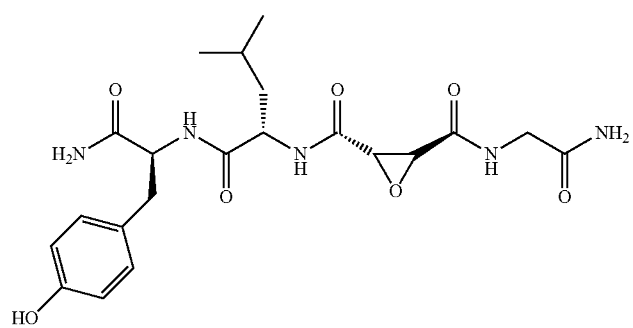 | Cat B | | | | | 464.2 | 464.1 |

TABLE 4-continued
Examples of structure and activity of epoxide inhibitors.
| Cpd # | Structure | Target | IC$_{50}$, CatZ (μM) | IC$_{50}$, CatB (μM) | IC$_{50}$, CatH (μM) | IC$_{50}$, CatC (μM) | Exp. mass (M + H)$^+$ | Actual mass (M + H)$^+$ |
|---|---|---|---|---|---|---|---|---|
| 35 | 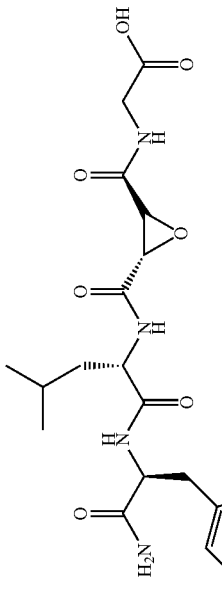 | Cat B | | | | | | |
| 36 | 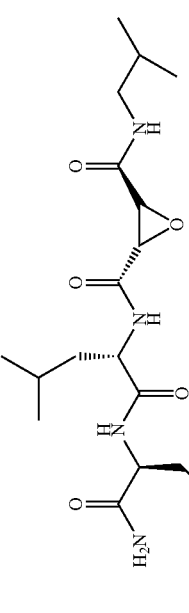 | Cat B | | | | | 463.2 | 463.4 |
| 37 | 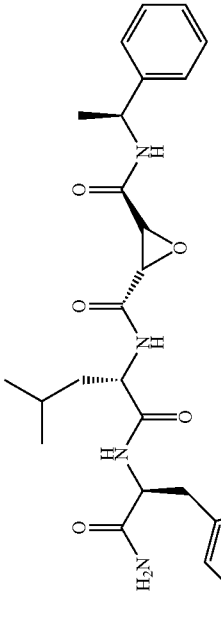 | Cat B | | | | | 511.2 | 511.1 |

TABLE 4-continued

Examples of structure and activity of epoxide inhibitors.

| Cpd # | Structure | Target | IC$_{50}$, CatZ (μM) | IC$_{50}$, CatB (μM) | IC$_{50}$, CatH (μM) | IC$_{50}$, CatC (μM) | Exp. mass (M + H)$^+$ | Actual mass (M + H)$^+$ |
|---|---|---|---|---|---|---|---|---|
| 38 | 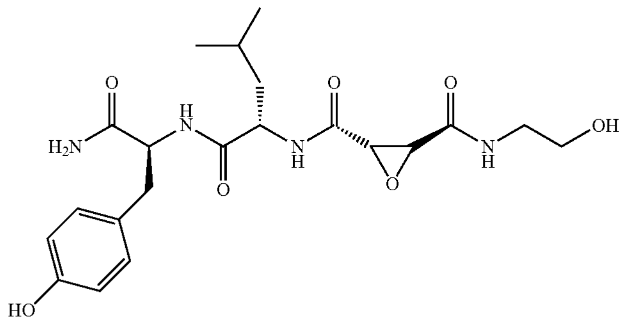 | Cat B | | | | | | |
| 39 | 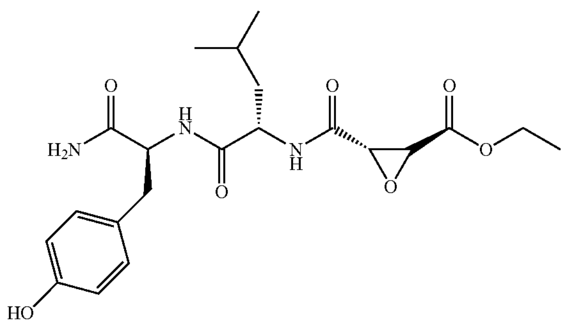 | General | | | | | 435.2 | |
| 40 | 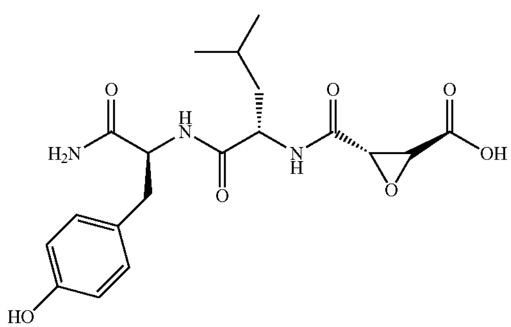 | General | 0.1 | 0.02 | 5.45 | 0.2 | 408.2 | 408.3 |

TABLE 4-continued

Examples of structure and activity of epoxide inhibitors.

| Cpd # | Structure | Target | IC$_{50}$, CatZ (μM) | IC$_{50}$, CatB (μM) | IC$_{50}$, CatH (μM) | IC$_{50}$, CatC (μM) | Exp. mass (M + H)$^+$ | Actual mass (M + H)$^+$ |
|---|---|---|---|---|---|---|---|---|
| 41 | 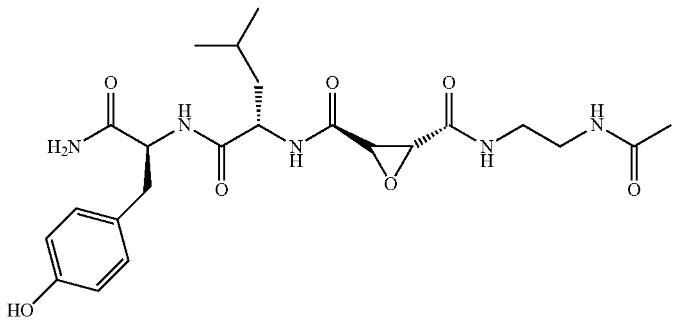 | Cat B | | | | | 492.2 | 492.3 |
| 42 | 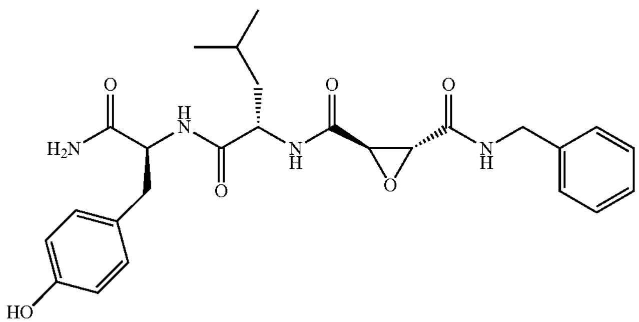 [SMILES: CC(C)C[C@H](NC(=O)[C@@H]1O[C@H]1C(=O)NCc1ccccc1)C(=O)N[C@@H](Cc1ccc(O)cc1)C(N)=O] | Cat B | | | | | | |
| 43 | 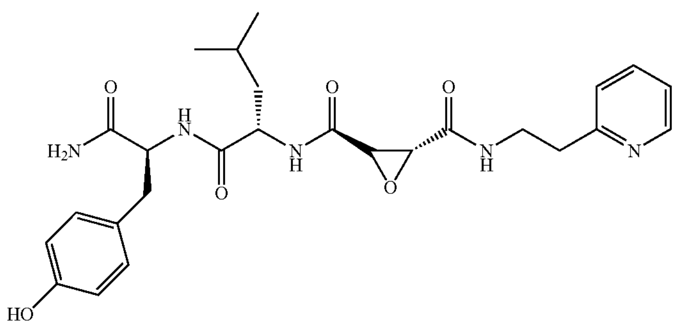 | Cat B | | | | | | |

TABLE 4-continued

Examples of structure and activity of epoxide inhibitors.

| Cpd # | Structure | Target | IC$_{50}$, CatZ (μM) | IC$_{50}$, CatB (μM) | IC$_{50}$, CatH (μM) | IC$_{50}$, CatC (μM) | Exp. mass (M + H)$^+$ | Actual mass (M + H)$^+$ |
|---|---|---|---|---|---|---|---|---|
| 44 | 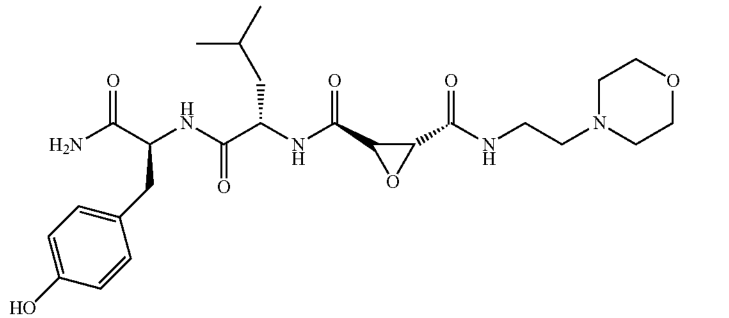 | N/D | | | | | | |
| 45 | 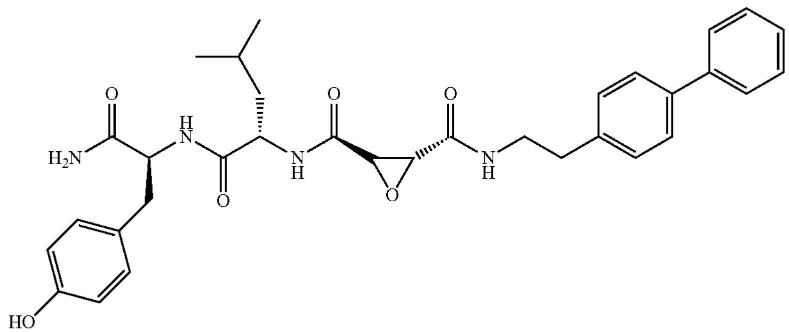 | Cat B | | | | | | |
| 46 | 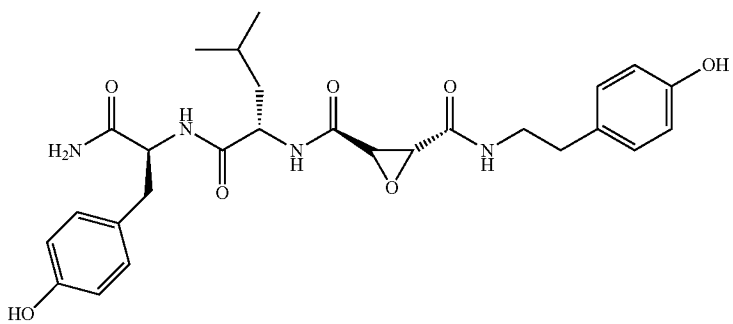 | Cat B | >10 | 0.01 | >50 | >50 | | |

TABLE 4-continued
Examples of structure and activity of epoxide inhibitors.
| Cpd # | Structure | Target | IC$_{50}$, CatZ (µM) | IC$_{50}$, CatB (µM) | IC$_{50}$, CatH (µM) | IC$_{50}$, CatC (µM) | Exp. mass (M + H)$^+$ | Actual mass (M + H)$^+$ |
|---|---|---|---|---|---|---|---|---|
| 47 | 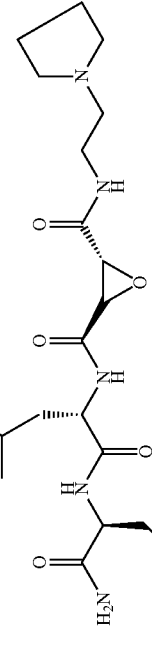 | N/D | | | | | 504.3 | 504.2 |
| 48 | 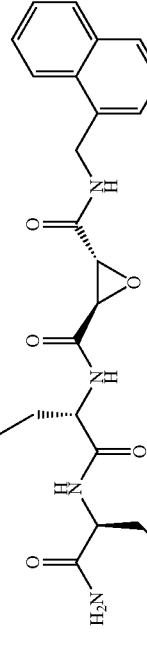 | Cat B | | | | | | |
| 49 | 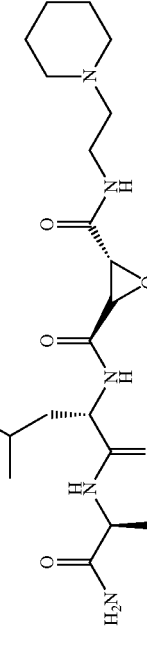 | Cat B | | | | | 518.3 | 518.5 |

TABLE 4-continued

Examples of structure and activity of epoxide inhibitors.

| Cpd # | Structure | Target | IC$_{50}$, CatZ (μM) | IC$_{50}$, CatB (μM) | IC$_{50}$, CatH (μM) | IC$_{50}$, CatC (μM) | Exp. mass (M + H)$^+$ | Actual mass (M + H)$^+$ |
|---|---|---|---|---|---|---|---|---|
| 50 | 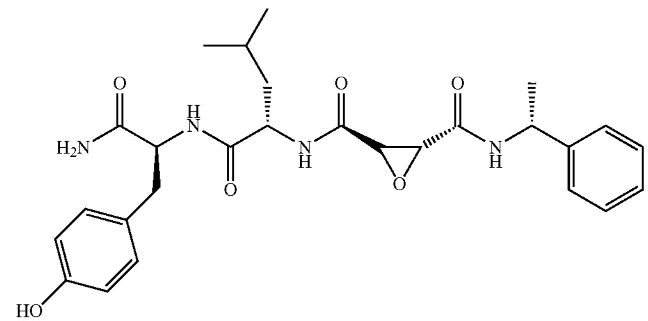 | Cat B | | | | | | |
| 51 | 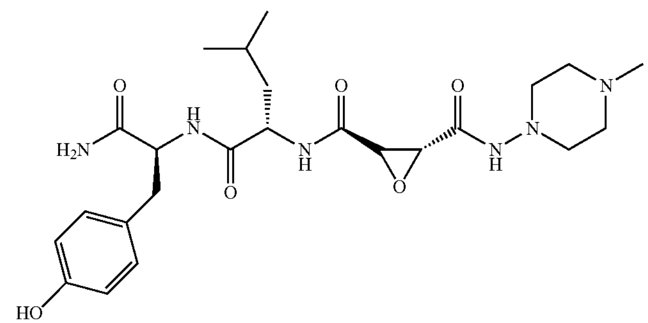 | N/D | | | | | 505.3 | 505.4 |
| 52 | 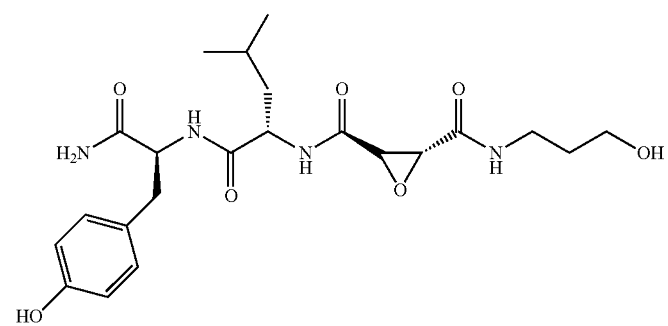 | Cat B | 1.8 | 0.05 | >50 | >50 | 465.2 | 465.3 |

TABLE 4-continued
Examples of structure and activity of epoxide inhibitors.
| Cpd # | Structure | Target | IC$_{50}$, CatZ (μM) | IC$_{50}$, CatB (μM) | IC$_{50}$, CatH (μM) | IC$_{50}$, CatC (μM) | Exp. mass (M + H)$^+$ | Actual mass (M + H)$^+$ |
|---|---|---|---|---|---|---|---|---|
| 53 | 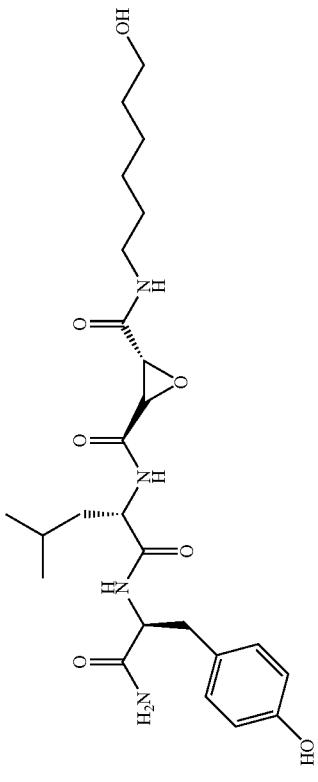 | Cat B | | | | | | |
| 54 | 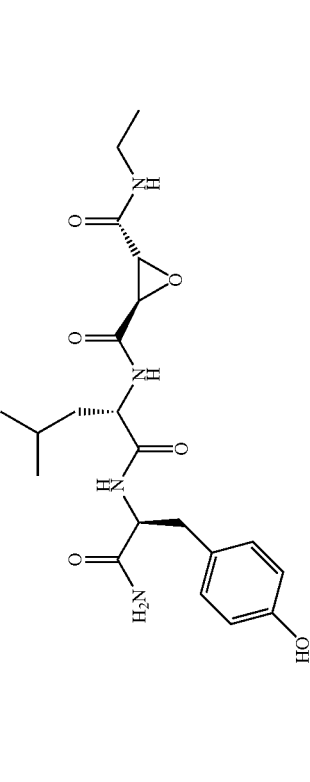 | N/D | | | | | | |
| 55 | 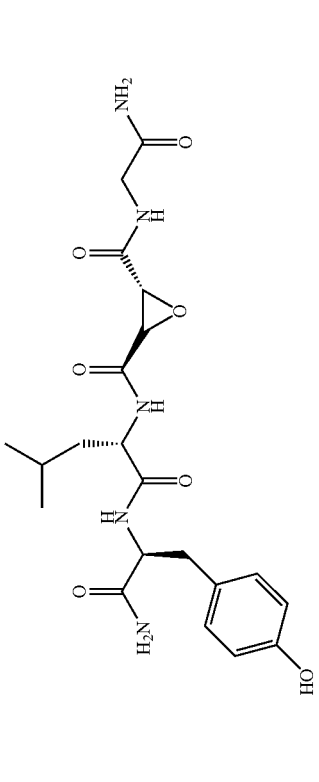 | N/D | | | | | 464.2 | 464.1 |

TABLE 4-continued

Examples of structure and activity of epoxide inhibitors.

| Cpd # | Structure | Target | IC$_{50}$, CatZ (µM) | IC$_{50}$, CatB (µM) | IC$_{50}$, CatH (µM) | IC$_{50}$, CatC (µM) | Exp. mass (M + H)$^+$ | Actual mass (M + H)$^+$ |
|---|---|---|---|---|---|---|---|---|
| 56 | 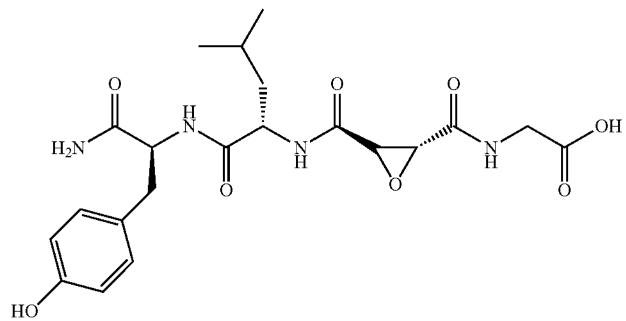 | N/D | | | | | 465.2 | 465.3 |
| 57 | 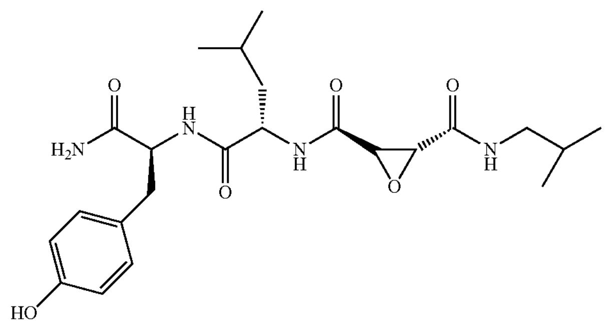 | Cat B | | | | | | |
| 58 | 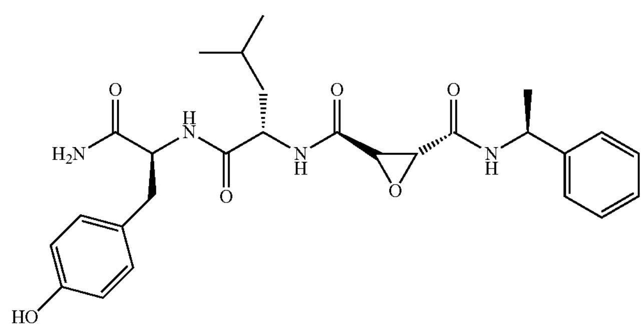 | Cat B | | | | | | |

TABLE 4-continued

Examples of structure and activity of epoxide inhibitors.

| Cpd # | Structure | Target | IC$_{50}$, CatZ (μM) | IC$_{50}$, CatB (μM) | IC$_{50}$, CatH (μM) | IC$_{50}$, CatC (μM) | Exp. mass (M + H)$^+$ | Actual mass (M + H)$^+$ |
|---|---|---|---|---|---|---|---|---|
| 59 | 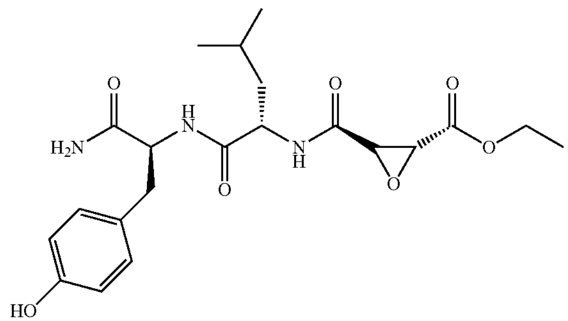 | Cat B | | | | | | |
| 60 | 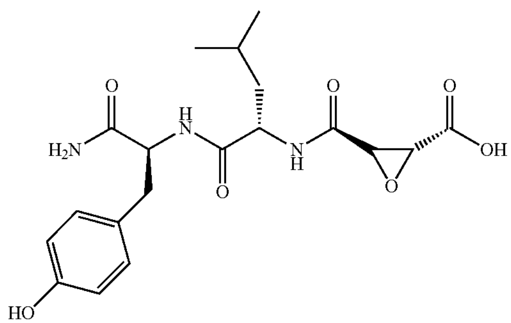 | Cat B & Z | 0.1 | 0.4 | >25 | >25 | 408.2 | 408.3 |
| 61 | 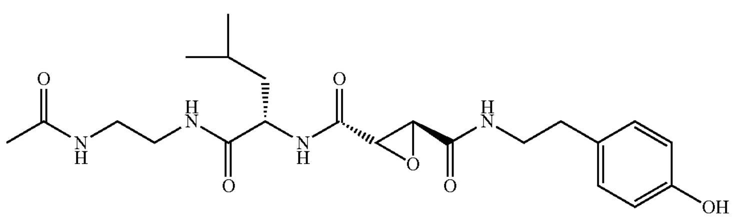 | N/D | | | | | 449.2 | 449.3 |

TABLE 4-continued

Examples of structure and activity of epoxide inhibitors.

| Cpd # | Structure | Target | IC$_{50}$, CatZ (μM) | IC$_{50}$, CatB (μM) | IC$_{50}$, CatH (μM) | IC$_{50}$, CatC (μM) | Exp. mass (M + H)$^+$ | Actual mass (M + H)$^+$ |
|---|---|---|---|---|---|---|---|---|
| 62 | 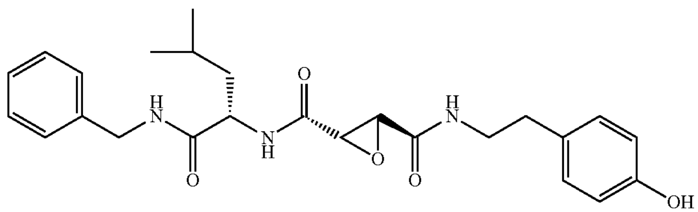 | N/D | | | | | 454.2 | 454.2 |
| 63 | 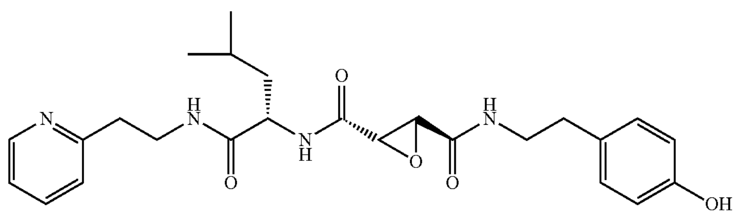 | Cat B & Z | >10 | 0.31 | >10 | >10 | 469.2 | 469.2 |
| 64 | 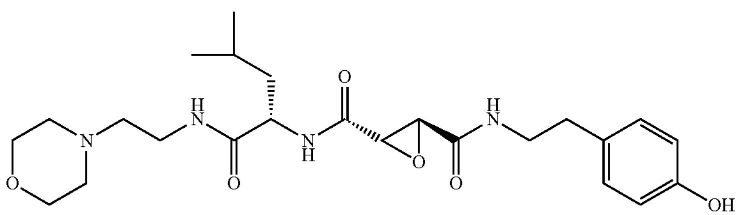 | N/D | | | | | 477.3 | 477.3 |
| 65 | 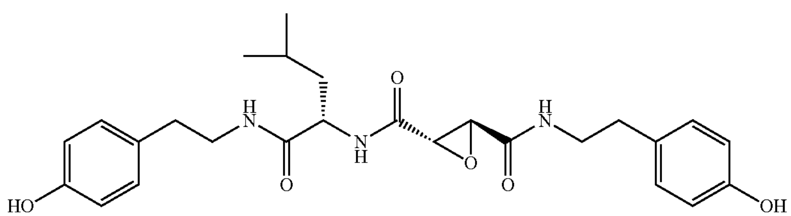 [SMILES: CC(C)C[C@H](NC(=O)[C@H]1O[C@@H]1C(=O)NCCc1ccc(O)cc1)C(=O)NCCc1ccc(O)cc1] | N/D | | | | | 484.2 | 484.5 |

TABLE 4-continued

Examples of structure and activity of epoxide inhibitors.

| Cpd # | Structure | Target | IC$_{50}$, CatZ (μM) | IC$_{50}$, CatB (μM) | IC$_{50}$, CatH (μM) | IC$_{50}$, CatC (μM) | Exp. mass (M + H)$^+$ | Actual mass (M + H)$^+$ |
|---|---|---|---|---|---|---|---|---|
| 66 | 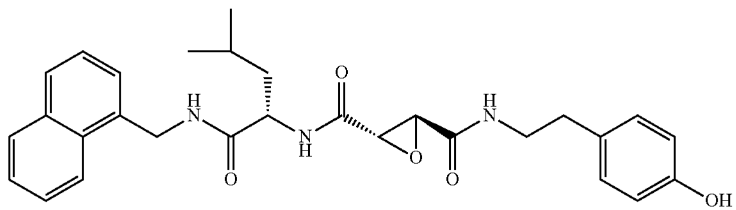 [SMILES: CC(C)C[C@H](NC(=O)[C@H]1O[C@@H]1C(=O)NCCc1ccc(O)cc1)C(=O)NCc1cccc2ccccc12] | General | 0.8 | 0.32 | 6.2 | 5.69 | 504.2 | 504.2 |
| 67 | 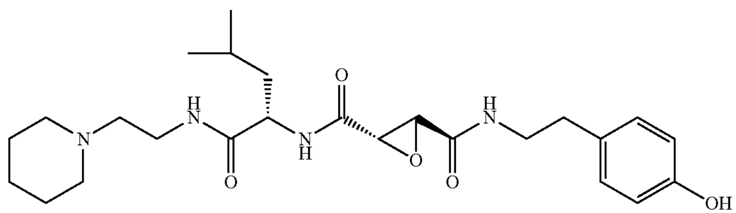 | Cat B | | | | | 475.3 | 475.3 |
| 68 | 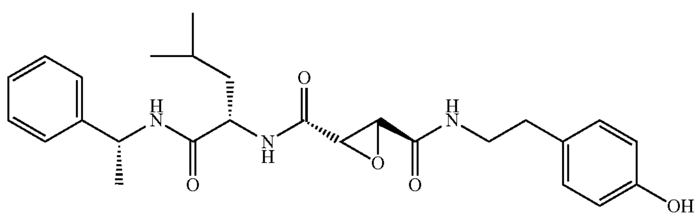 | N/D | | | | | 468.2 | 468.3 |
| 69 | 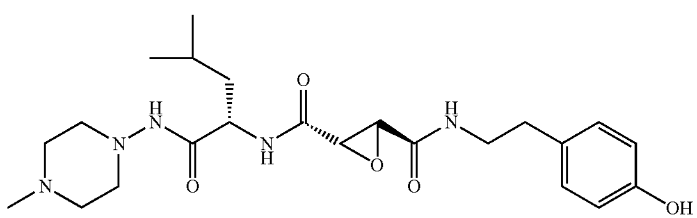 | N/D | | | | | 462.3 | 462.4 |

TABLE 4-continued

Examples of structure and activity of epoxide inhibitors.

| Cpd # | Structure | Target | IC$_{50}$, CatZ (μM) | IC$_{50}$, CatB (μM) | IC$_{50}$, CatH (μM) | IC$_{50}$, CatC (μM) | Exp. mass (M + H)$^+$ | Actual mass (M + H)$^+$ |
|---|---|---|---|---|---|---|---|---|
| 70 | 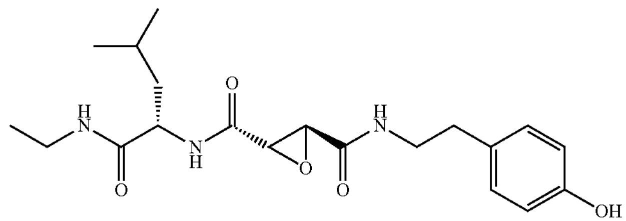 | N/D | | | | | 392.2 | 392.1 |
| 71 | 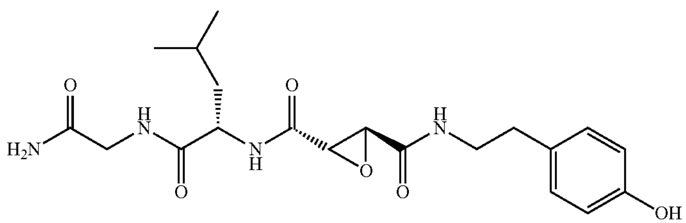 | N/D | | | | | 421.2 | 421.2 |
| 72 | 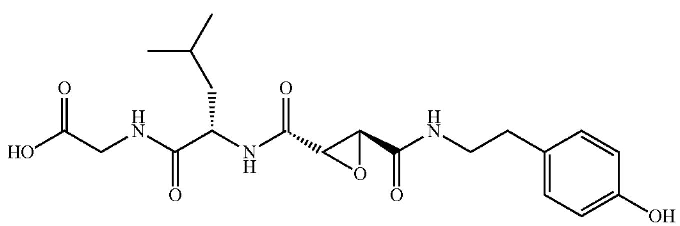 | N/D | | | | | 422.2 | 422.0 |
| 73 | 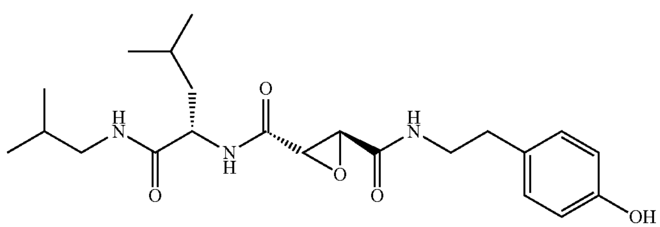 | N/D | | | | | 420.2 | 420.1 |

TABLE 4-continued

Examples of structure and activity of epoxide inhibitors.

| Cpd # | Structure | Target | IC$_{50}$, CatZ (μM) | IC$_{50}$, CatB (μM) | IC$_{50}$, CatH (μM) | IC$_{50}$, CatC (μM) | Exp. mass (M + H)$^+$ | Actual mass (M + H)$^+$ |
|---|---|---|---|---|---|---|---|---|
| 74 | 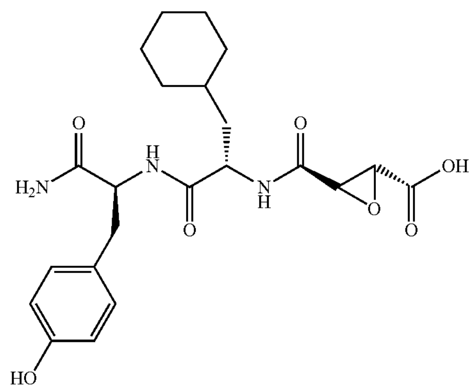 | Cat B & Z | 0.3 | 1.95 | >25 | >25 | 448.2 | 448.2 |
| 75 | 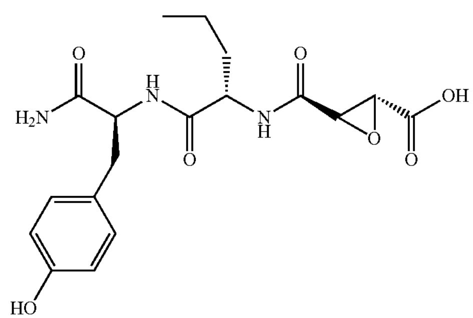 | Cat B & Z | 0.2 | 0.27 | >25 | >25 | 394.2 | 394.3 |

TABLE 4-continued

Examples of structure and activity of epoxide inhibitors.

| Cpd # | Structure | Target | IC$_{50}$, CatZ (μM) | IC$_{50}$, CatB (μM) | IC$_{50}$, CatH (μM) | IC$_{50}$, CatC (μM) | Exp. mass (M + H)⁺ | Actual mass (M + H)⁺ |
|---|---|---|---|---|---|---|---|---|
| 76 | 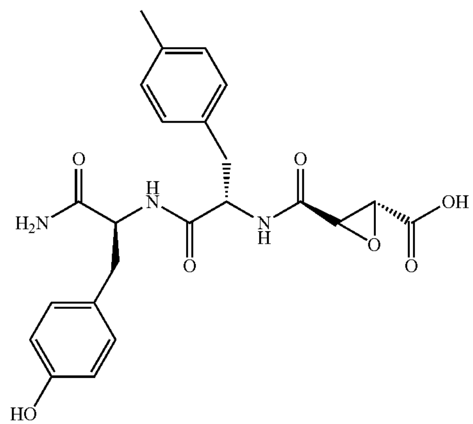 | Cat Z | 0.2 | 6.8 | >25 | >25 | 456.2 | 456.3 |
| 77 | 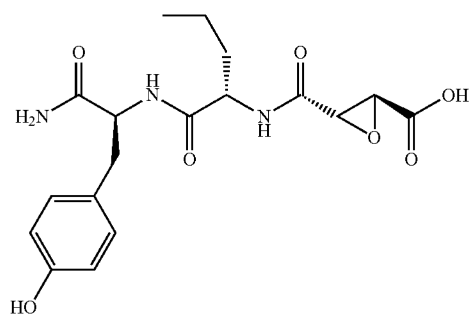 | General | 0.1 | 0.03 | 0.74 | 0.45 | 394.2 | 394.3 |

TABLE 4-continued
Examples of structure and activity of epoxide inhibitors.
| Cpd # | Structure | Target | IC$_{50}$, CatZ (μM) | IC$_{50}$, CatB (μM) | IC$_{50}$, CatH (μM) | IC$_{50}$, CatC (μM) | Exp. mass (M + H)$^+$ | Actual mass (M + H)$^+$ |
|---|---|---|---|---|---|---|---|---|
| 78 | 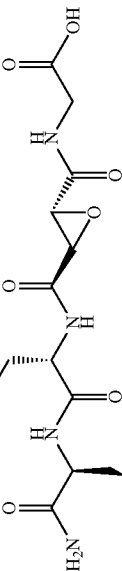 | Cat B | 1 | 0.28 | >10 | >10 | 451.2 | 451.3 |
| 79 | 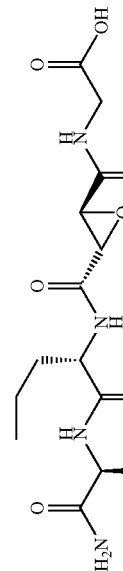 | Cat B | 1.3 | 0.19 | 5.85 | 19.3 | 451.2 | 451.2 |
| 80 | 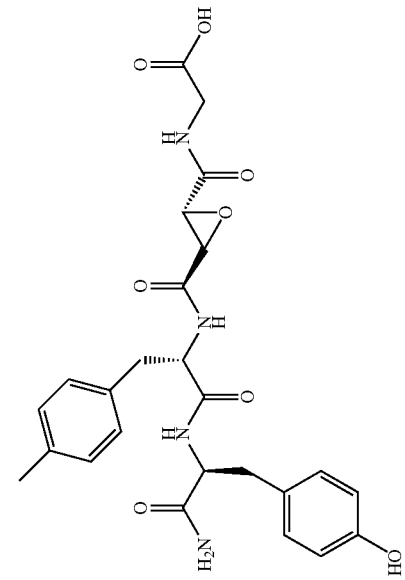 | Cat B & Z | 0.8 | >10 | >10 | >10 | 513.2 | 513.5 |

TABLE 4-continued

Examples of structure and activity of epoxide inhibitors.

| Cpd # | Structure | Target | IC$_{50}$, CatZ (μM) | IC$_{50}$, CatB (μM) | IC$_{50}$, CatH (μM) | IC$_{50}$, CatC (μM) | Exp. mass (M + H)$^+$ | Actual mass (M + H)$^+$ |
|---|---|---|---|---|---|---|---|---|
| 81 | 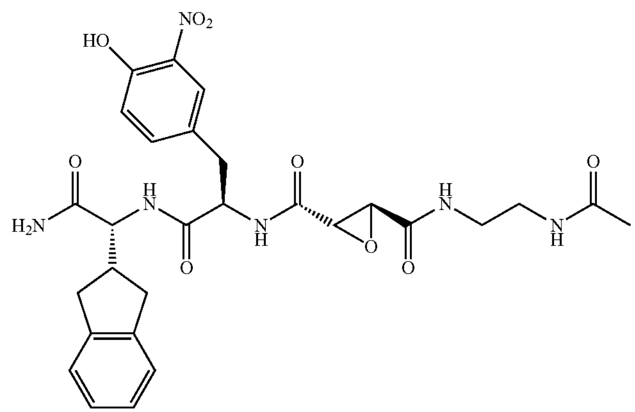 | N/D | | | | | | |
| 82 | 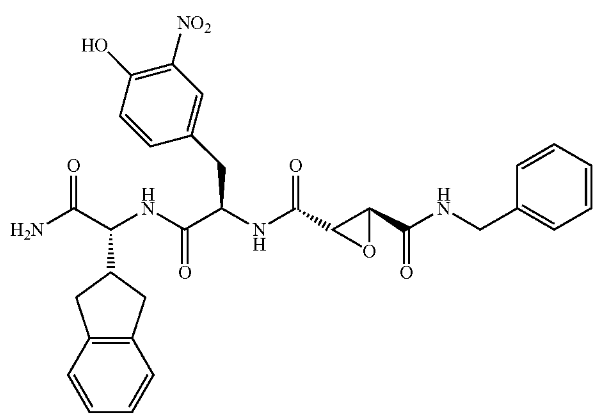 | N/D | | | | | | |

TABLE 4-continued

Examples of structure and activity of epoxide inhibitors.

| Cpd # | Structure | Target | IC$_{50}$, CatZ (μM) | IC$_{50}$, CatB (μM) | IC$_{50}$, CatH (μM) | IC$_{50}$, CatC (μM) | Exp. mass (M + H)$^+$ | Actual mass (M + H)$^+$ |
|---|---|---|---|---|---|---|---|---|
| 83 | 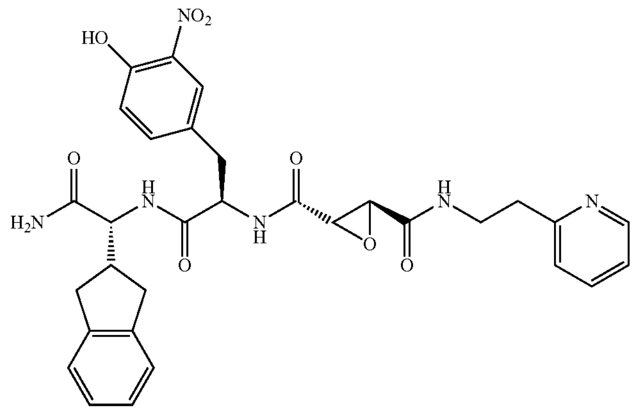 | N/D | | | | | | |
| 84 | 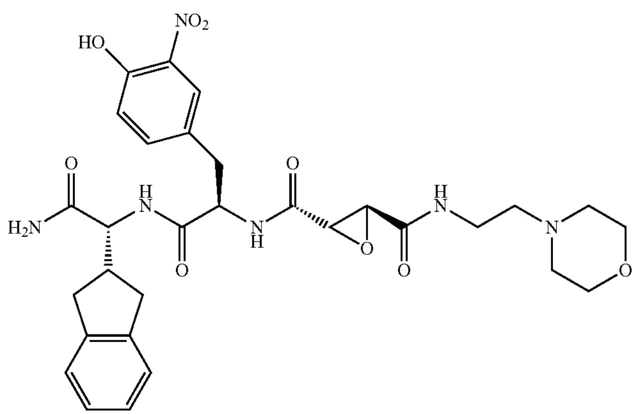 | N/D | | | | | | |

TABLE 4-continued

Examples of structure and activity of epoxide inhibitors.

| Cpd # | Structure | Target | IC$_{50}$, CatZ (μM) | IC$_{50}$, CatB (μM) | IC$_{50}$, CatH (μM) | IC$_{50}$, CatC (μM) | Exp. mass (M + H)$^+$ | Actual mass (M + H)$^+$ |
|---|---|---|---|---|---|---|---|---|
| 85 | 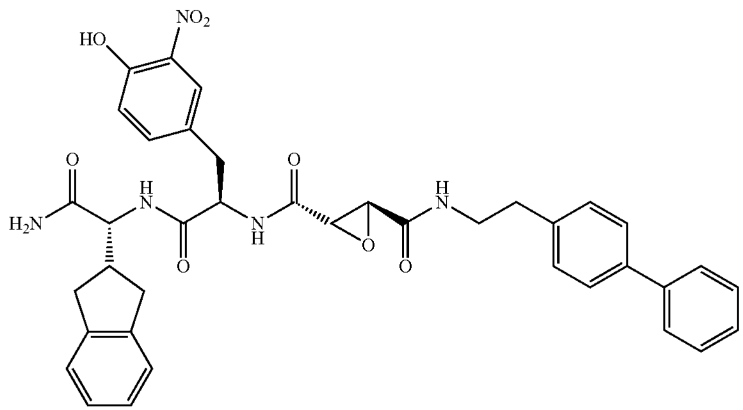 | N/D | | | | | | |
| 86 | 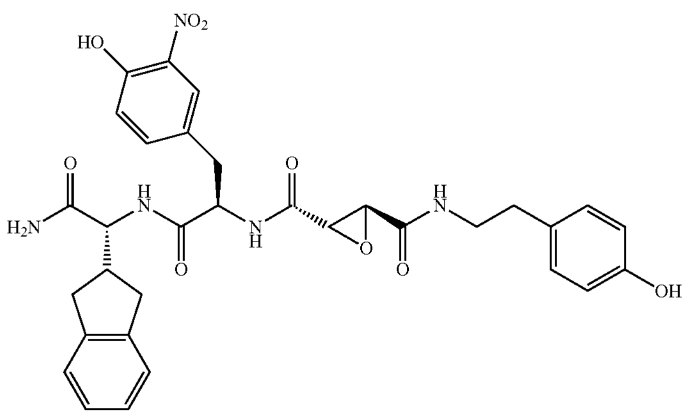 | N/D | | | | | | |

TABLE 4-continued

Examples of structure and activity of epoxide inhibitors.

| Cpd # | Structure | Target | IC$_{50}$, CatZ (μM) | IC$_{50}$, CatB (μM) | IC$_{50}$, CatH (μM) | IC$_{50}$, CatC (μM) | Exp. mass (M + H)$^+$ | Actual mass (M + H)$^+$ |
|---|---|---|---|---|---|---|---|---|
| 87 | 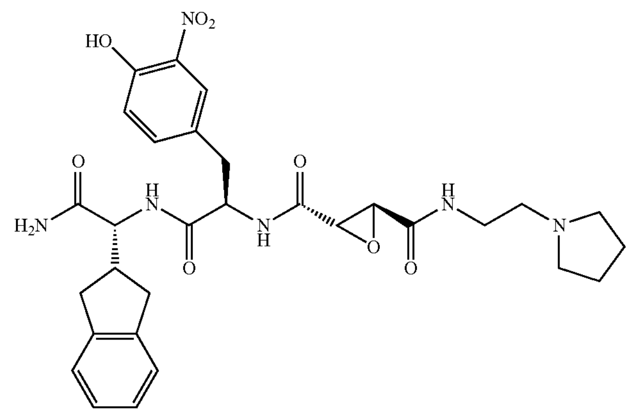 | N/D | | | | | | |
| 88 | 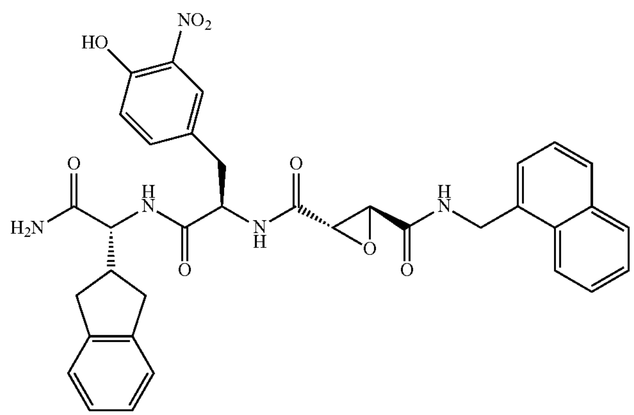 [SMILES: NC(=O)[C@H](NC(=O)[C@@H](Cc1ccc(O)c([N+](=O)[O-])c1)NC(=O)[C@H]1O[C@@H]1C(=O)NCc1cccc2ccccc12)C1Cc2ccccc2C1] | N/D | | | | | | |

TABLE 4-continued

Examples of structure and activity of epoxide inhibitors.

| Cpd # | Structure | Target | IC$_{50}$, CatZ (µM) | IC$_{50}$, CatB (µM) | IC$_{50}$, CatH (µM) | IC$_{50}$, CatC (µM) | Exp. mass (M + H)$^+$ | Actual mass (M + H)$^+$ |
|---|---|---|---|---|---|---|---|---|
| 89 | 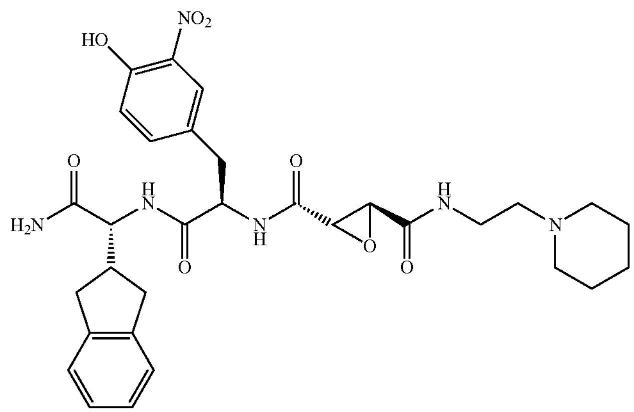 | N/D | | | | | | |
| 90 | 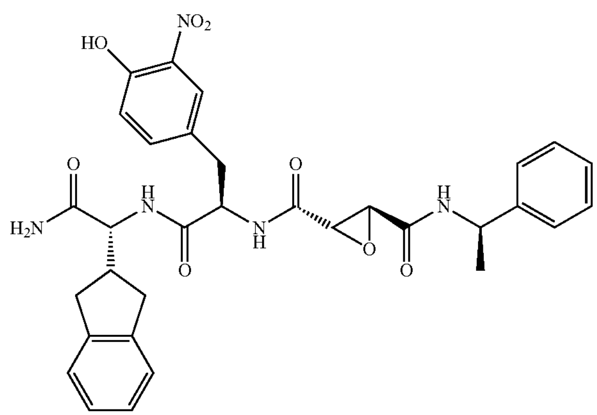 | N/D | | | | | | |

TABLE 4-continued

Examples of structure and activity of epoxide inhibitors.

| Cpd # | Structure | Target | IC$_{50}$, CatZ (μM) | IC$_{50}$, CatB (μM) | IC$_{50}$, CatH (μM) | IC$_{50}$, CatC (μM) | Exp. mass (M + H)$^+$ | Actual mass (M + H)$^+$ |
|---|---|---|---|---|---|---|---|---|
| 91 | 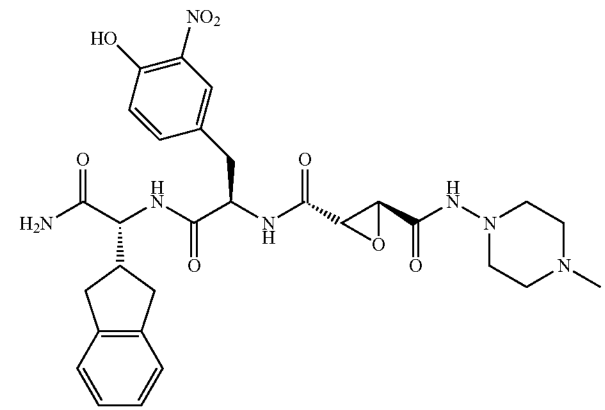 | N/D | | | | | | |
| 92 | 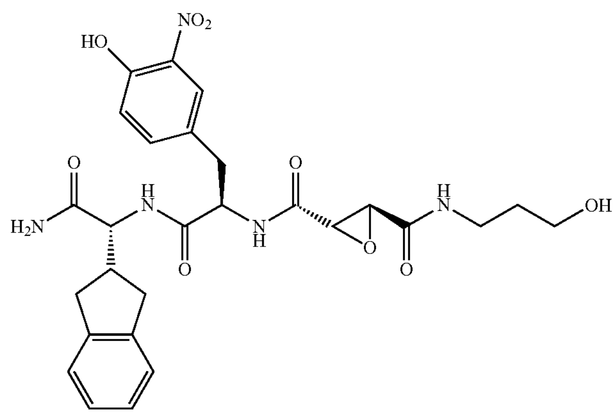 | N/D | | | | | | |

TABLE 4-continued

Examples of structure and activity of epoxide inhibitors.

| Cpd # | Structure | Target | IC$_{50}$, CatZ (μM) | IC$_{50}$, CatB (μM) | IC$_{50}$, CatH (μM) | IC$_{50}$, CatC (μM) | Exp. mass (M + H)$^+$ | Actual mass (M + H)$^+$ |
|---|---|---|---|---|---|---|---|---|
| 93 | 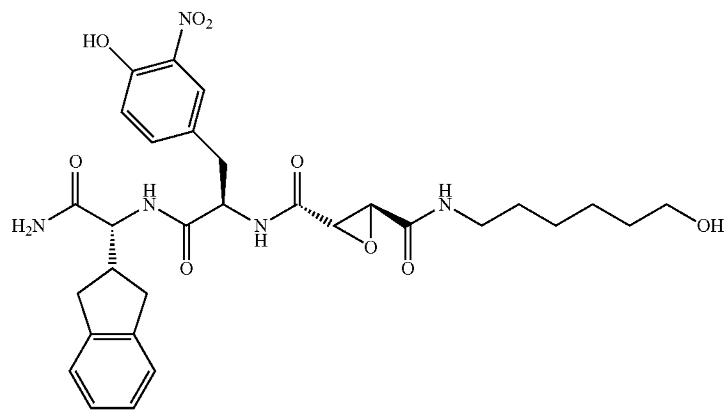 | N/D | | | | | | |
| 94 | 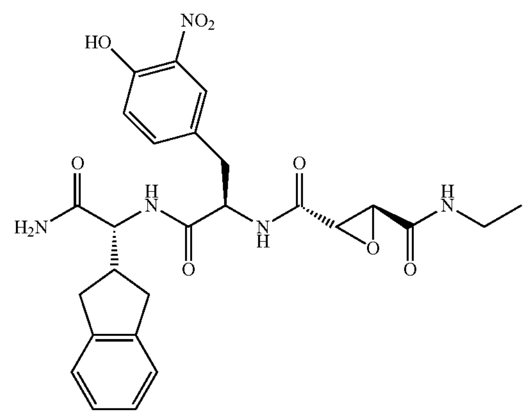 | N/D | | | | | | |

TABLE 4-continued

Examples of structure and activity of epoxide inhibitors.

| Cpd # | Structure | Target | IC$_{50}$, CatZ (μM) | IC$_{50}$, CatB (μM) | IC$_{50}$, CatH (μM) | IC$_{50}$, CatC (μM) | Exp. mass (M + H)$^+$ | Actual mass (M + H)$^+$ |
|---|---|---|---|---|---|---|---|---|
| 95 | 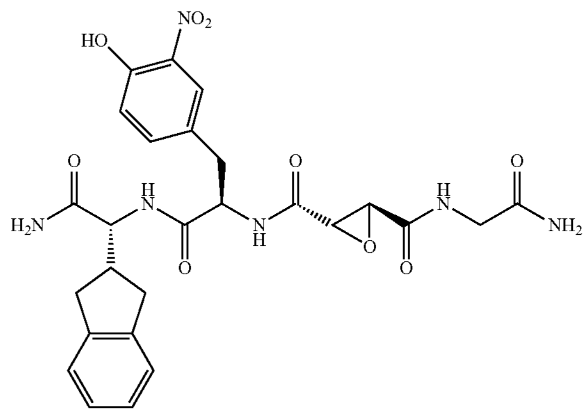 | N/D | | | | | | |
| 96 | 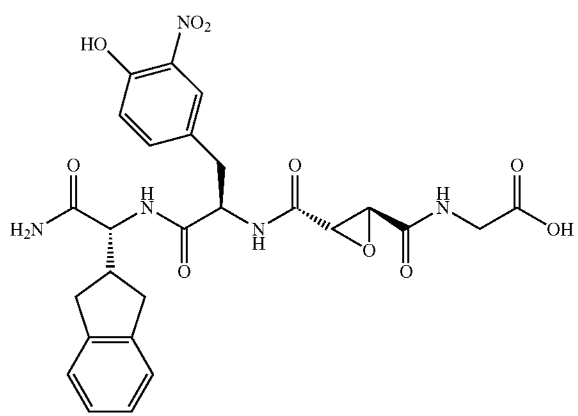 | N/D | | | | | | |

TABLE 4-continued

Examples of structure and activity of epoxide inhibitors.

| Cpd # | Structure | Target | IC$_{50}$, CatZ (μM) | IC$_{50}$, CatB (μM) | IC$_{50}$, CatH (μM) | IC$_{50}$, CatC (μM) | Exp. mass (M + H)$^+$ | Actual mass (M + H)$^+$ |
|---|---|---|---|---|---|---|---|---|
| 97 | 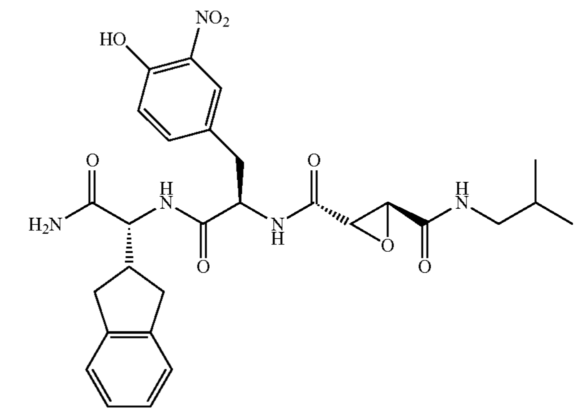 | N/D | | | | | | |
| 98 | 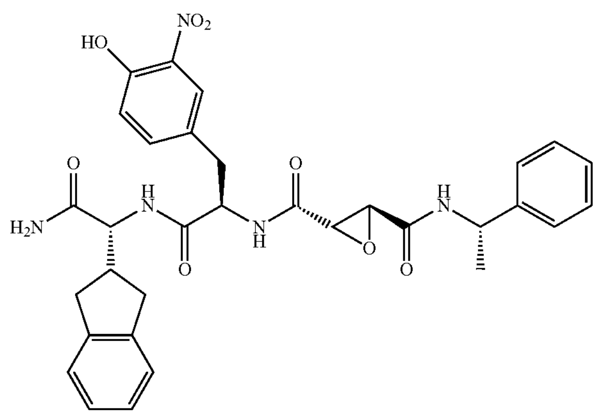 | N/D | | | | | | |

TABLE 4-continued

Examples of structure and activity of epoxide inhibitors.

| Cpd # | Structure | Target | IC$_{50}$, CatZ (μM) | IC$_{50}$, CatB (μM) | IC$_{50}$, CatH (μM) | IC$_{50}$, CatC (μM) | Exp. mass (M + H)$^+$ | Actual mass (M + H)$^+$ |
|---|---|---|---|---|---|---|---|---|
| 99 | 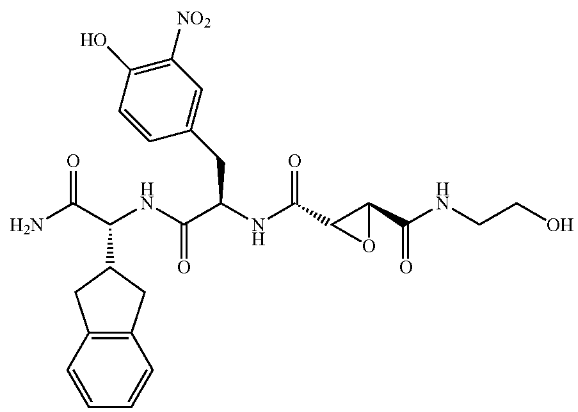 | N/D | | | | | | |
| 100 | 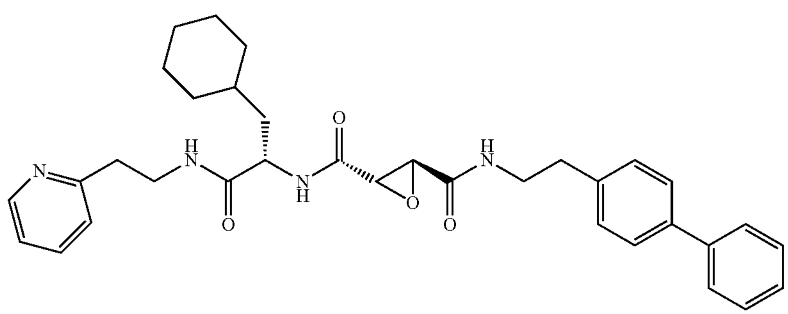 | | | | | | 569.3 | 569.0 |

TABLE 4-continued

Examples of structure and activity of epoxide inhibitors.

| Cpd # | Structure | Target | IC$_{50}$, CatZ (μM) | IC$_{50}$, CatB (μM) | IC$_{50}$, CatH (μM) | IC$_{50}$, CatC (μM) | Exp. mass (M + H)$^+$ | Actual mass (M + H)$^+$ |
|---|---|---|---|---|---|---|---|---|
| 101 | 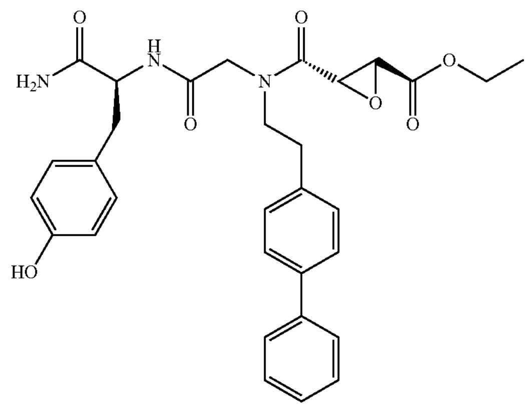 | | | | | | 560.2 | 560.1 |
| 102 | 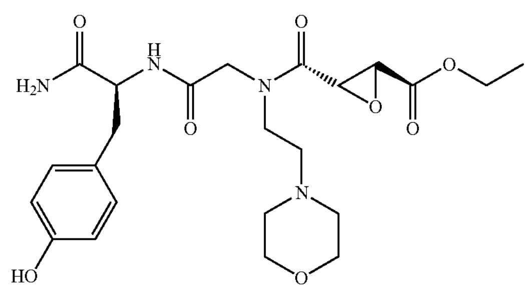 | | | | | | 493.2 | 493.3 |
| 103 | 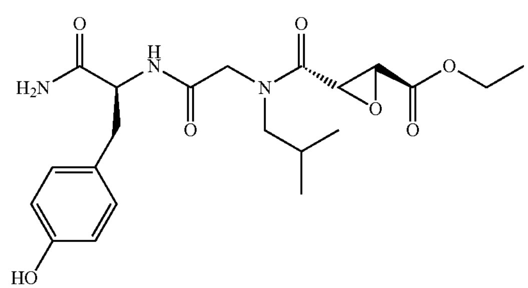 | Cat B | | | | | 436.2 | 436.3 |

TABLE 4-continued

Examples of structure and activity of epoxide inhibitors.

| Cpd # | Structure | Target | IC$_{50}$, CatZ (μM) | IC$_{50}$, CatB (μM) | IC$_{50}$, CatH (μM) | IC$_{50}$, CatC (μM) | Exp. mass (M + H)$^+$ | Actual mass (M + H)$^+$ |
|---|---|---|---|---|---|---|---|---|
| 104 | 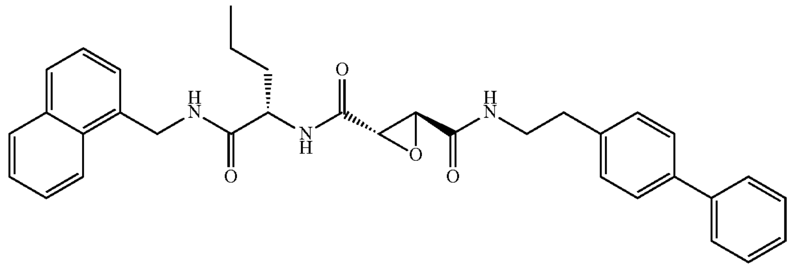 [SMILES: CCC[C@H](NC(=O)[C@H]1O[C@@H]1C(=O)NCCc1ccc(-c2ccccc2)cc1)C(=O)NCc1cccc2ccccc12] | | | | | | 550.3 | 550.3 |
| 105 | 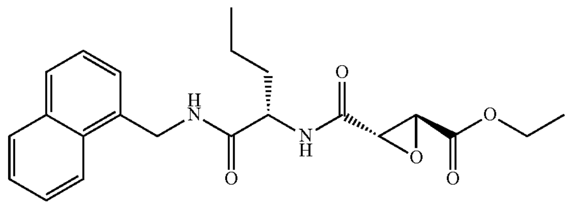 [SMILES: CCC[C@H](NC(=O)[C@H]1O[C@@H]1C(=O)OCC)C(=O)NCc1cccc2ccccc12] | General | | | | | 399.2 | 399.3 |
| 106 | 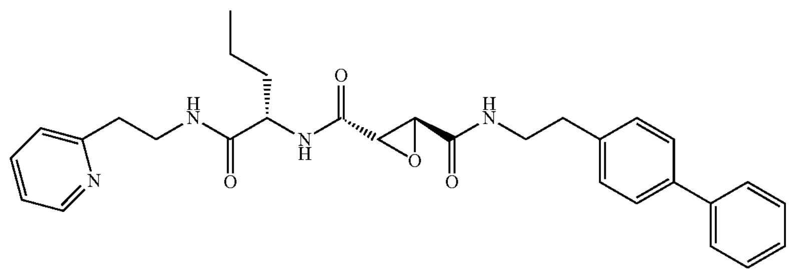 | Cat B | | | | | 515.3 | 515.4 |

TABLE 4-continued

Examples of structure and activity of epoxide inhibitors.

| Cpd # | Structure | Target | IC$_{50}$, CatZ (μM) | IC$_{50}$, CatB (μM) | IC$_{50}$, CatH (μM) | IC$_{50}$, CatC (μM) | Exp. mass (M + H)$^+$ | Actual mass (M + H)$^+$ |
|---|---|---|---|---|---|---|---|---|
| 107 | 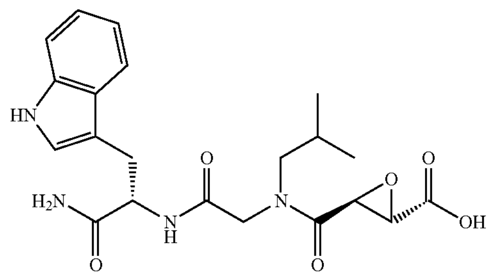 | | | | | | 431.2 | 431.4 |
| 108 | 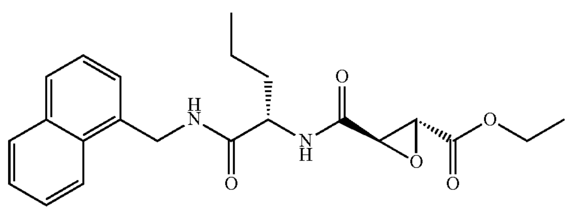 [SMILES: CCC[C@H](NC(=O)[C@@H]1O[C@H]1C(=O)OCC)C(=O)NCc1cccc2ccccc12] | | | | | | 399.2 | 398.9 |
| 109 | 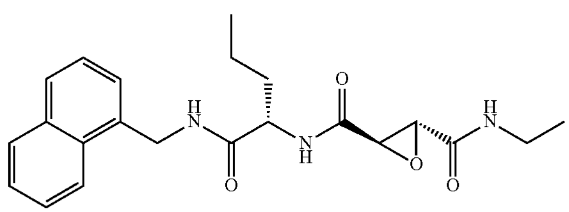 [SMILES: CCC[C@H](NC(=O)[C@@H]1O[C@H]1C(=O)NCC)C(=O)NCc1cccc2ccccc12] | | | | | | | |
| 110 | 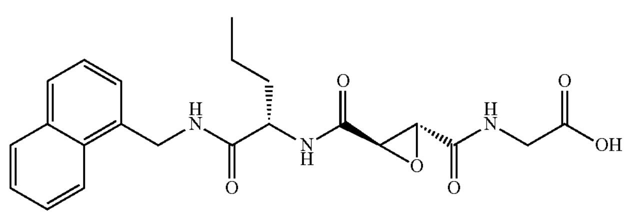 [SMILES: CCC[C@H](NC(=O)[C@@H]1O[C@H]1C(=O)NCC(=O)O)C(=O)NCc1cccc2ccccc12] | | | | | | | |

TABLE 4-continued

Examples of structure and activity of epoxide inhibitors.

| Cpd # | Structure | Target | IC$_{50}$, CatZ (μM) | IC$_{50}$, CatB (μM) | IC$_{50}$, CatH (μM) | IC$_{50}$, CatC (μM) | Exp. mass (M + H)$^+$ | Actual mass (M + H)$^+$ |
|---|---|---|---|---|---|---|---|---|
| 111 | 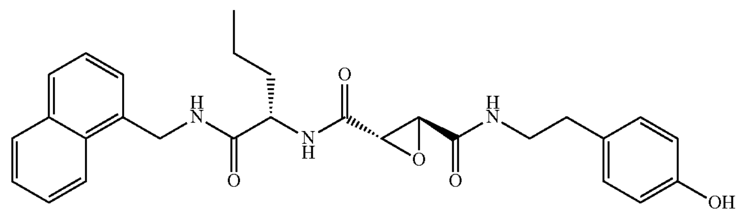 [SMILES: CCC[C@H](NC(=O)[C@H]1O[C@@H]1C(=O)NCCc1ccc(O)cc1)C(=O)NCc1cccc2ccccc12] | Cat Z | | | | | 490.2 | 490.3 |
| 112 | 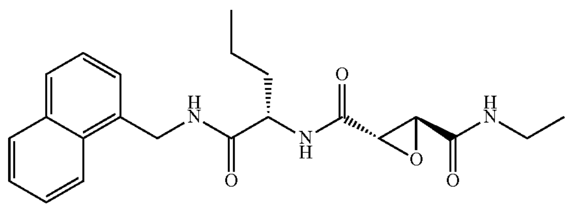 [SMILES: CCC[C@H](NC(=O)[C@H]1O[C@@H]1C(=O)NCC)C(=O)NCc1cccc2ccccc12] | | | | | | | |
| 113 | 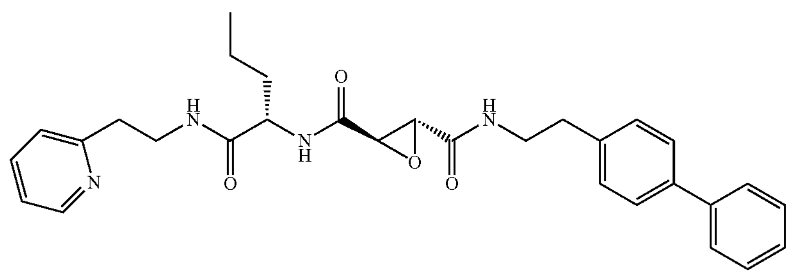 [SMILES: CCC[C@H](NC(=O)[C@@H]1O[C@H]1C(=O)NCCc1ccc(-c2ccccc2)cc1)C(=O)NCCc1ccccn1] | | | | | | 515.3 | 515.4 |
| 114 | 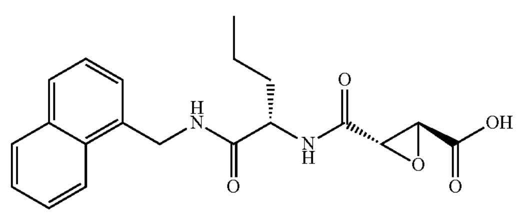 [SMILES: CCC[C@H](NC(=O)[C@H]1O[C@@H]1C(=O)O)C(=O)NCc1cccc2ccccc12] | General | | | | | | |

TABLE 4-continued

Examples of structure and activity of epoxide inhibitors.

| Cpd # | Structure | Target | IC$_{50}$, CatZ (µM) | IC$_{50}$, CatB (µM) | IC$_{50}$, CatH (µM) | IC$_{50}$, CatC (µM) | Exp. mass (M + H)$^+$ | Actual mass (M + H)$^+$ |
|---|---|---|---|---|---|---|---|---|
| 115 | 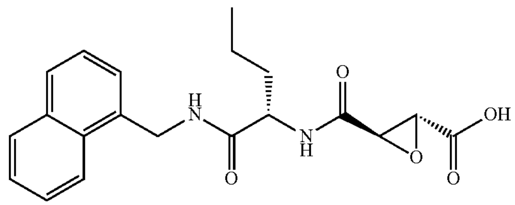 [SMILES: CCC[C@H](NC(=O)[C@@H]1O[C@H]1C(=O)O)C(=O)NCc1cccc2ccccc12] | Cat Z | | | | | | |
| 116 | 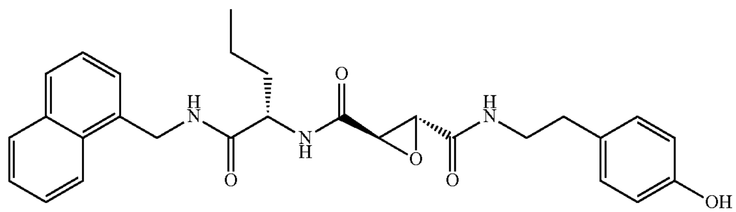 [SMILES: CCC[C@H](NC(=O)[C@@H]1O[C@H]1C(=O)NCCc1ccc(O)cc1)C(=O)NCc1cccc2ccccc12] | | | | | | | |
| 117 | 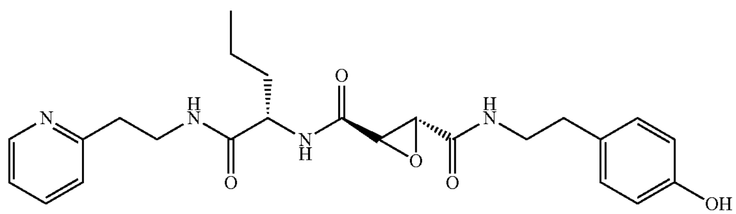 | | | | | | | |
| 118 | 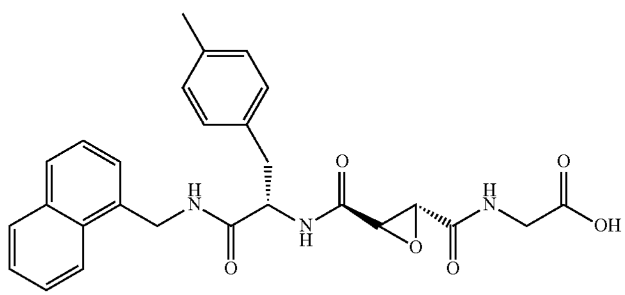 | | | | | | | |

TABLE 4-continued

Examples of structure and activity of epoxide inhibitors.

| Cpd # | Structure | Target | IC$_{50}$, CatZ (μM) | IC$_{50}$, CatB (μM) | IC$_{50}$, CatH (μM) | IC$_{50}$, CatC (μM) | Exp. mass (M + H)$^+$ | Actual mass (M + H)$^+$ |
|---|---|---|---|---|---|---|---|---|
| 119 | 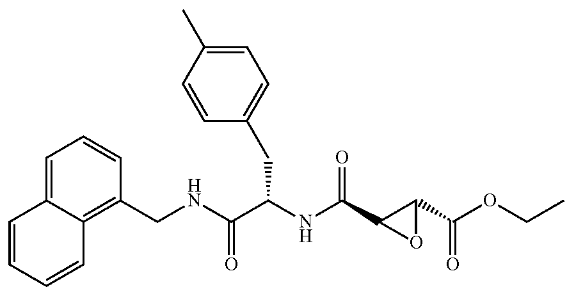 | Cat Z | | | | | | |
| 120 | 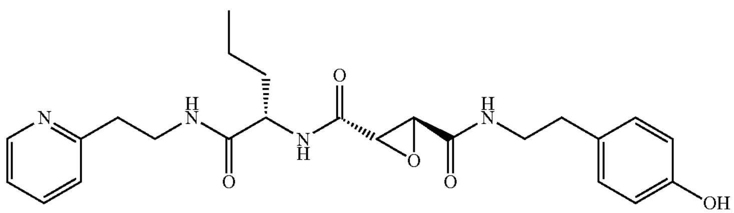 | Cat B | | | | | | |
| 121 | 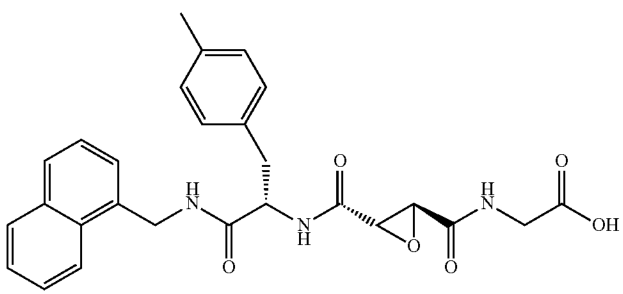 | Cat Z | | | | | | |

TABLE 4-continued

Examples of structure and activity of epoxide inhibitors.

| Cpd # | Structure | Target | IC$_{50}$, CatZ (µM) | IC$_{50}$, CatB (µM) | IC$_{50}$, CatH (µM) | IC$_{50}$, CatC (µM) | Exp. mass (M + H)$^+$ | Actual mass (M + H)$^+$ |
|---|---|---|---|---|---|---|---|---|
| 122 | 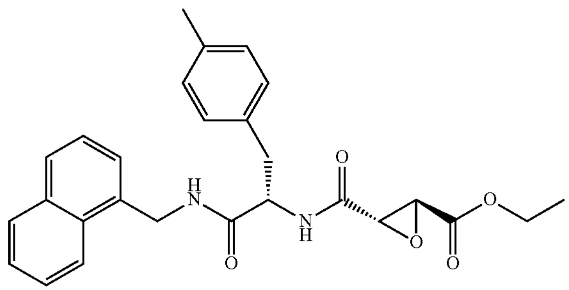 [SMILES: CCOC(=O)[C@H]1O[C@@H]1C(=O)N[C@@H](Cc1ccc(C)cc1)C(=O)NCc1cccc2ccccc12] | Cat Z | | | | | | |
| 123 | 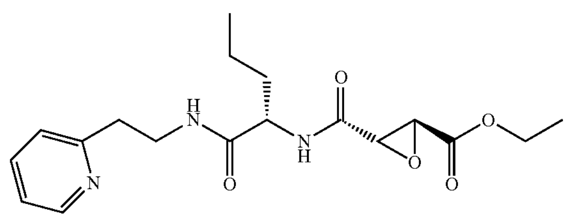 | General | | | | | | |
| 124 | 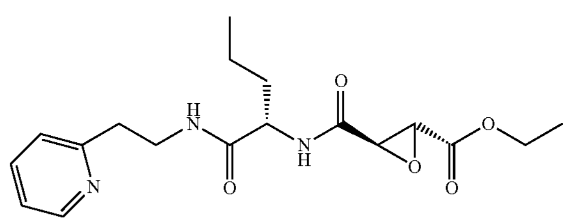 | General | | | | | | |

TABLE 4-continued

Examples of structure and activity of epoxide inhibitors.

| Cpd # | Structure | Target | IC$_{50}$, CatZ (μM) | IC$_{50}$, CatB (μM) | IC$_{50}$, CatH (μM) | IC$_{50}$, CatC (μM) | Exp. mass (M + H)$^+$ | Actual mass (M + H)$^+$ |
|---|---|---|---|---|---|---|---|---|
| 125 | 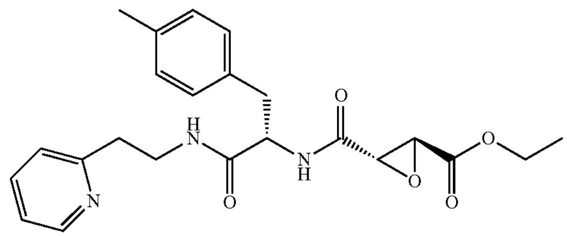 [SMILES: CCOC(=O)[C@H]1O[C@@H]1C(=O)N[C@@H](Cc1ccc(C)cc1)C(=O)NCCc1ccccn1] | N/D | | | | | | |
| 126 | 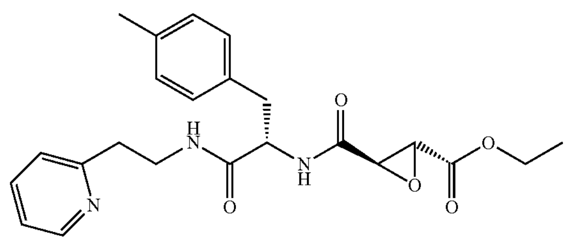 | General | | | | | | |

[1]Cathepsin Z ("Cat Z") is also known as Cathepsin X ("Cat X") and Cathepsin P ("Cat P").
These terms are used interchangeably herein.

Profiling of Libraries in Crude Rat Liver Extracts.

As shown in FIG. 1, compounds in which the $R_1$ position was varied through 19 amines were added to total rat liver extracts at the indicated concentrations for 30 minutes and then $^{125}$I-labeled JPM-OEt was added for 30 minutes. The library compounds all contained a tyrosine residue at the $R_3$ position. They contained either a leucine residue (top and middle panels) or a 4-methylphenylalanine residue (bottom panel) at the $A_2$ position. The amine at $R_1$ is indicated above each panel, with numbering as defined in Table 1. Samples were analyzed by SDS-PAGE followed by autoradiography. Controls (C) are shown where DMSO was added in place of the inhibitor. The parent compounds JPM-OEt (Et) and JPM-565 (OH) are also included as positive controls. Note the loss of reactivity for all (2R,3R) compounds and the change in specificity of JPM analogs in which the (2R,3R) (middle panel—OH and Et) is used in place of the (2S,3S) (top panel—OH and Et) epoxides. Also note that most of the $R_1$ amines produce highly selective cathepsin B inhibitors (except for amine 6 and 17).

Competition in Rat Liver Homogenates for Two Cathepsin B Specific Compounds.

The results shown in FIG. 2 demonstrate that (R,R)-epoxide compounds 46 and 52 retain similar potency for cathepsin B compared to parent compound JPM-565, which was shown to have efficacy in the RIP-Tag cancer model. Joyce et al., Cancer Cell 5:443-453, 2004. The compounds show little or no activity against other cathepsin targets at concentrations as high as 50 micromolar.

Characterization of Additional Inhibitor Compounds.

FIGS. 3 and 4 show additional competition assays with other compounds of the invention at various concentrations. The compounds were added to total rat liver extracts at the indicated concentrations, as described above, and the mixtures were subsequently treated with $^{125}$I-labeled JPM-OEt to label proteins with residual activity. The in vivo pharmacokinetic properties, potency, and selectivity of some of these compounds are further described in Sadaghiani et al., Chem. Biol. 14:499-511, 2007, which is incorporated herein by reference in its entirety.

Summary

The results summarized in Table 4 demonstrate that the R,R conformation generally shifts the selectivity toward endopeptidases (B, X) relative to exopeptidases (H, C), whereas the (S,S) conformation typically shows general inhibition toward all cathepsins. The results further allow the identification of prime-side modifications (i.e., $R_1$ variants) that drive selectivity towards either cathepsin B or Z or show general reactivity towards the entire family. Also identified are $R_3$ elements that can be used to drive selectivity for cathepsin B or that make inhibitors targeting all family members generally.

All of the above-cited references and publications are incorporated by reference herein in their entireties.

Those skilled in the art will recognize, or be able to ascertain using no more than routine experimentation, numerous equivalents to the specific method and reagents described herein. Such equivalents are considered to be within the scope of this invention and are covered by the following claims.

What is claimed is:
1. A compound selected from:

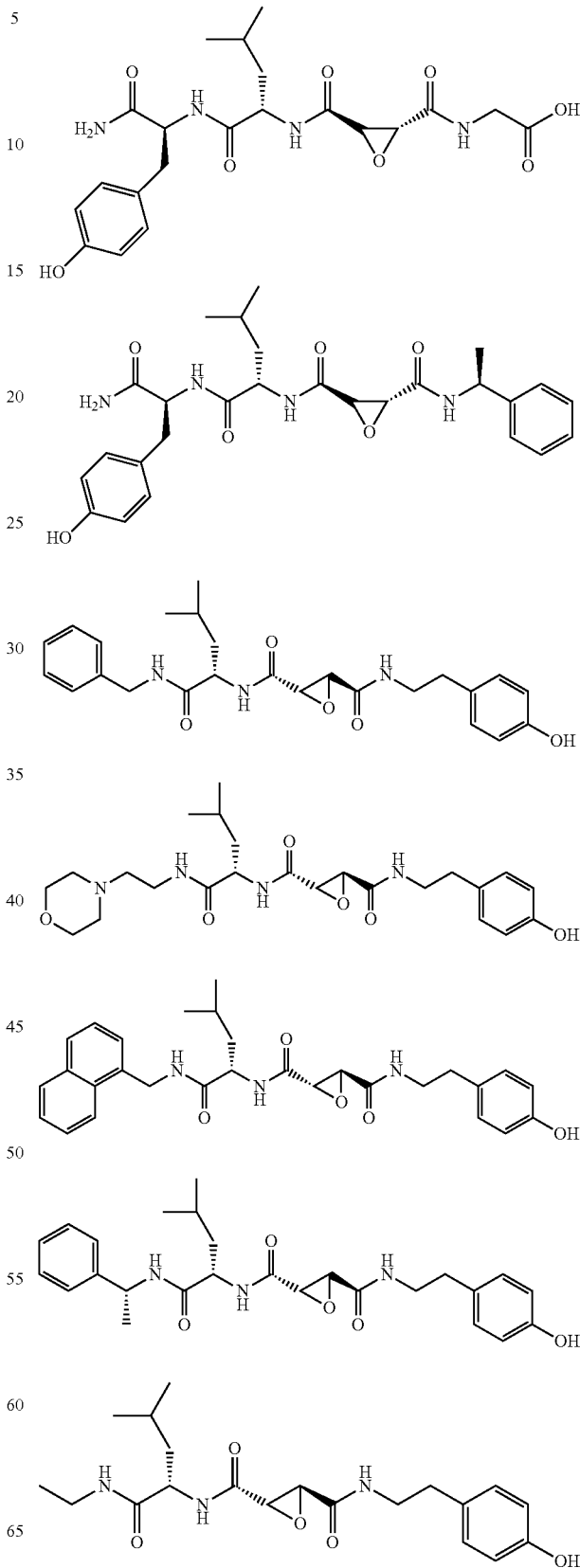

145
-continued
146
-continued
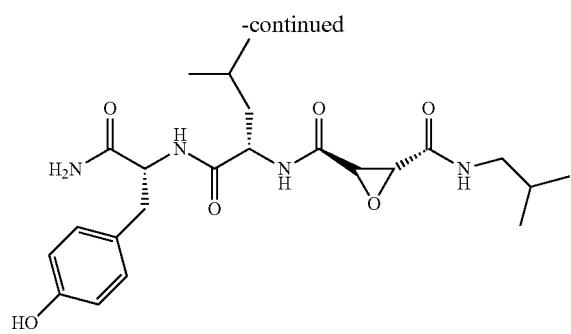
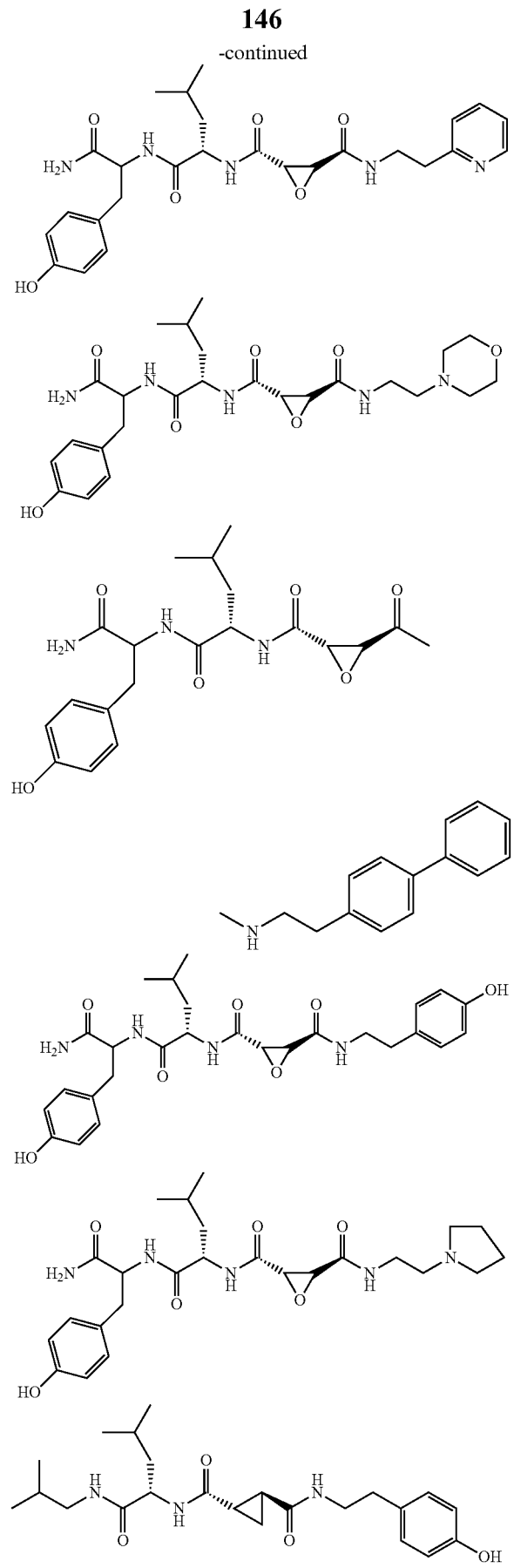

147
-continued
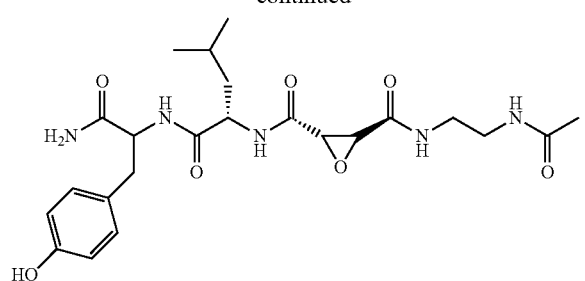
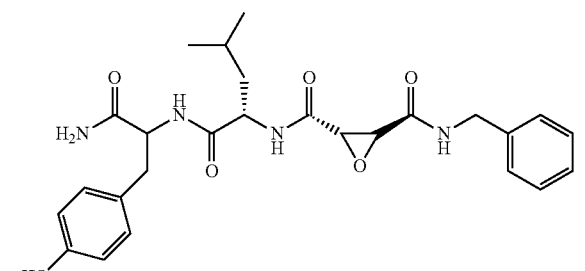
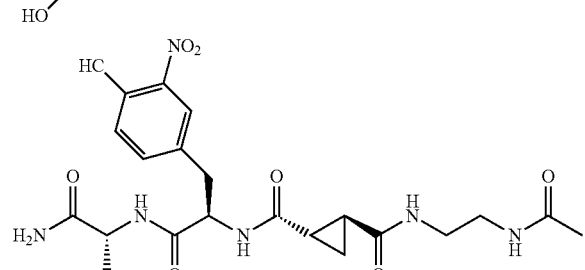
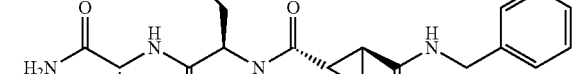
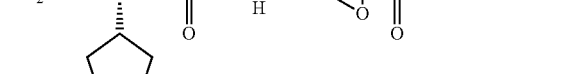
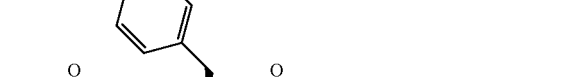
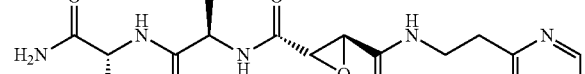
148
-continued
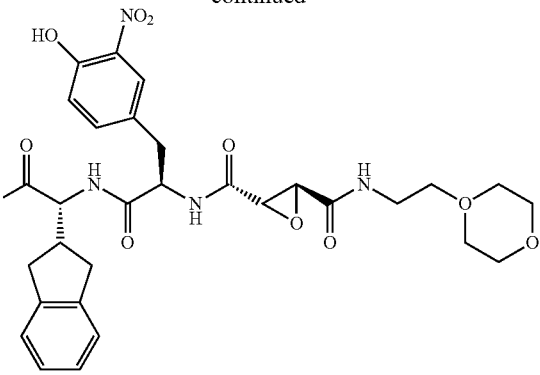
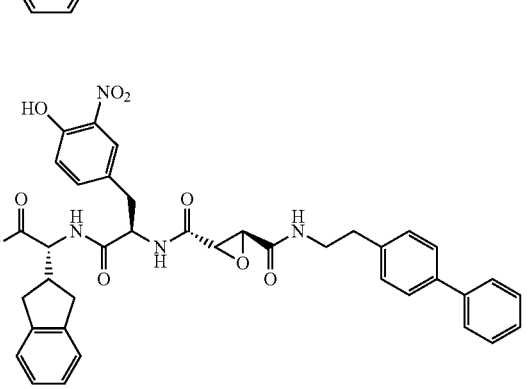
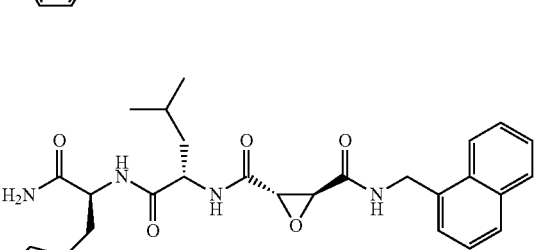
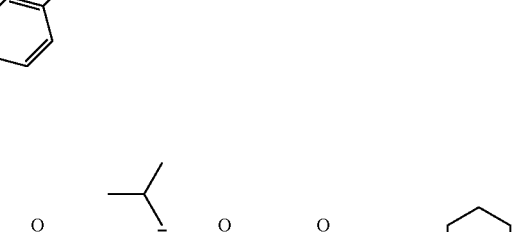
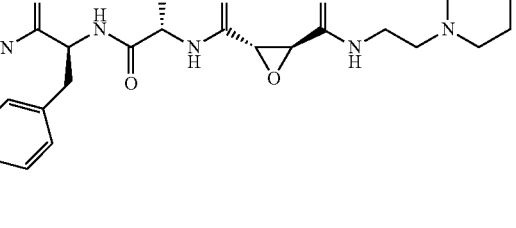
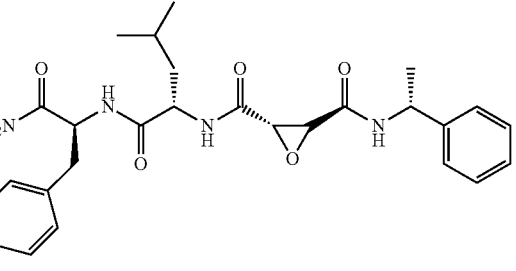

149
-continued
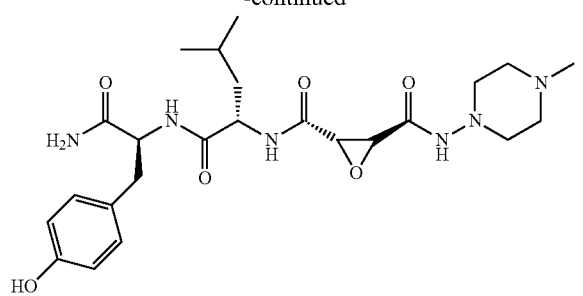
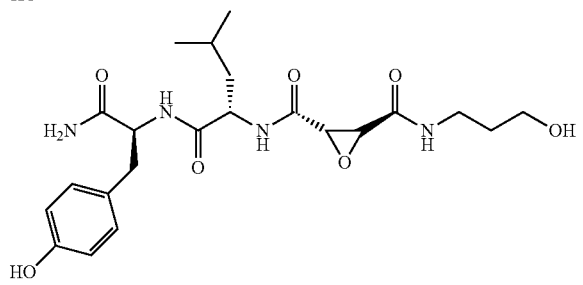
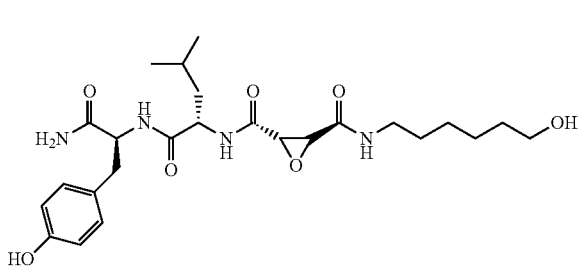
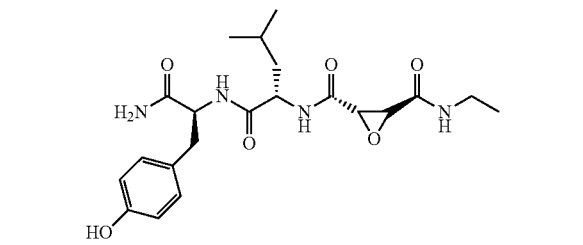
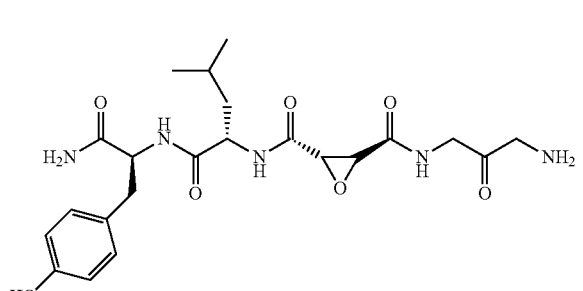
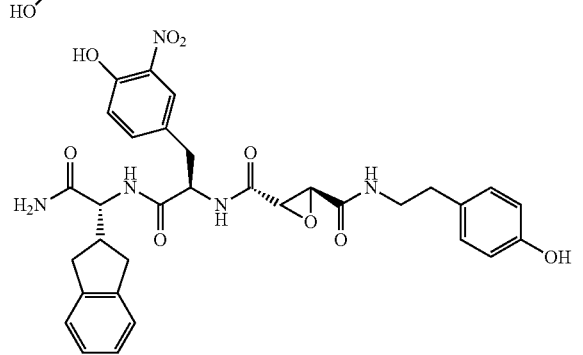
150
-continued
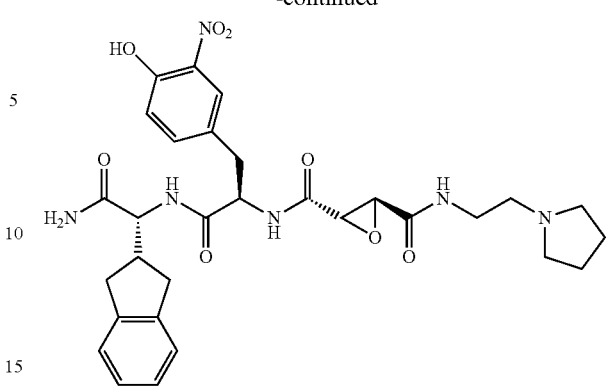
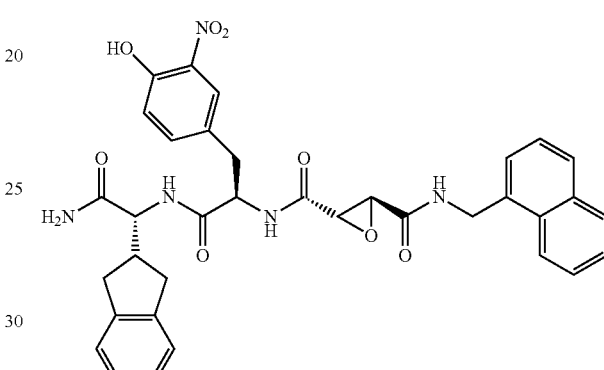
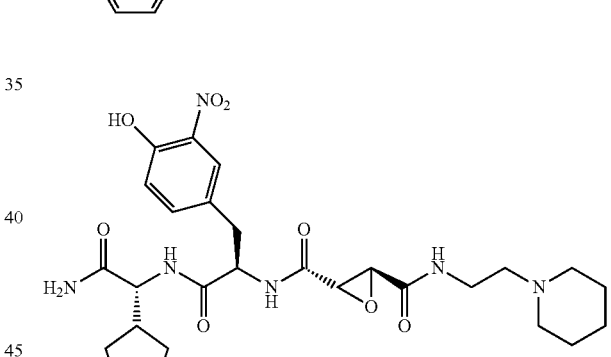
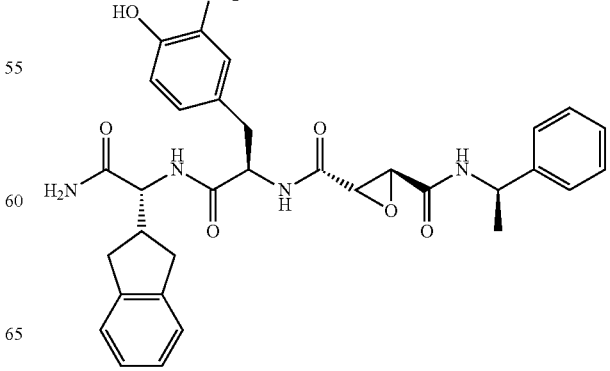

151
-continued
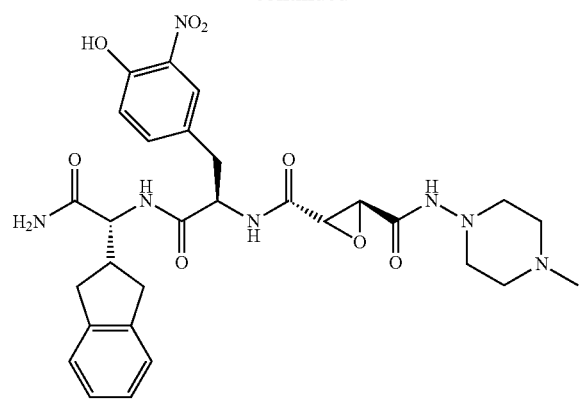
152
-continued
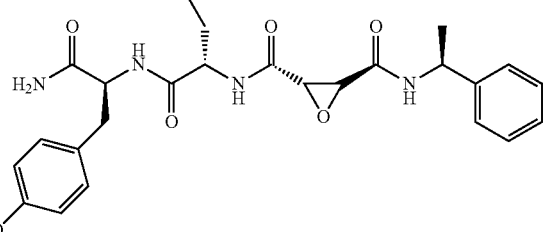
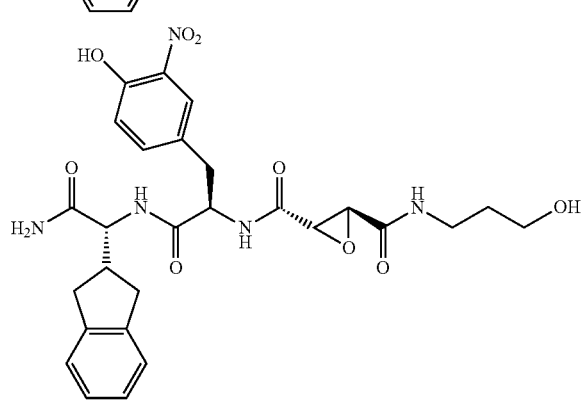
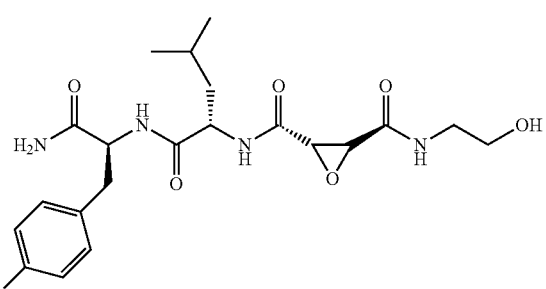
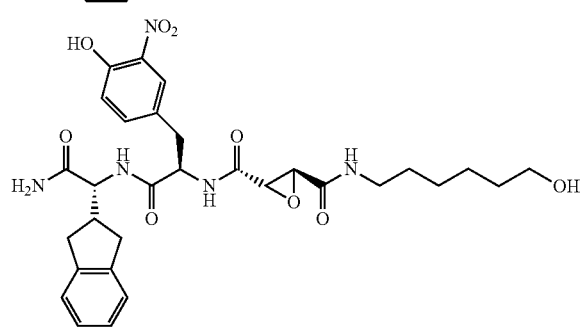
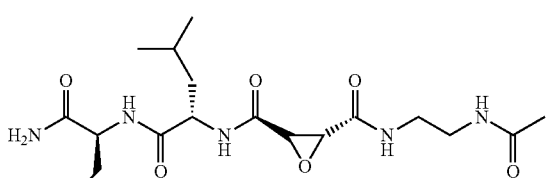
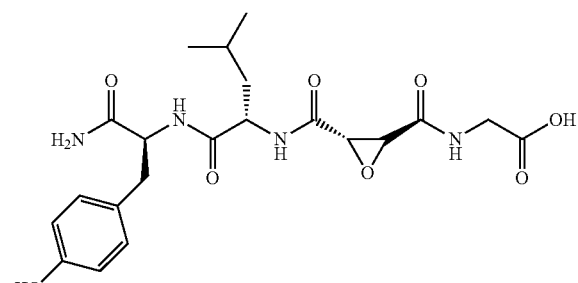
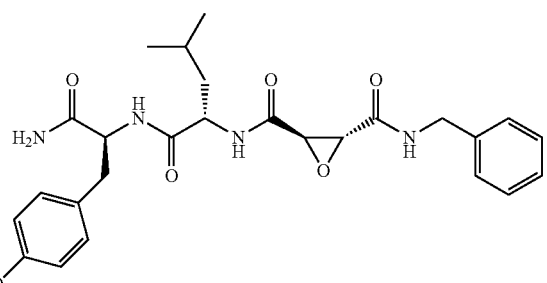
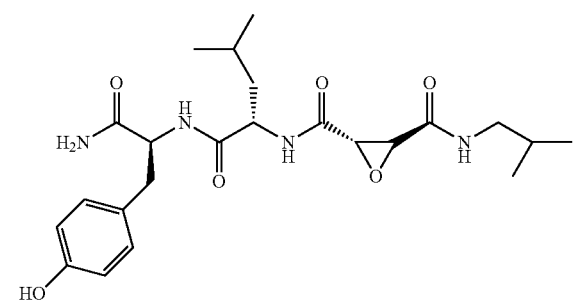
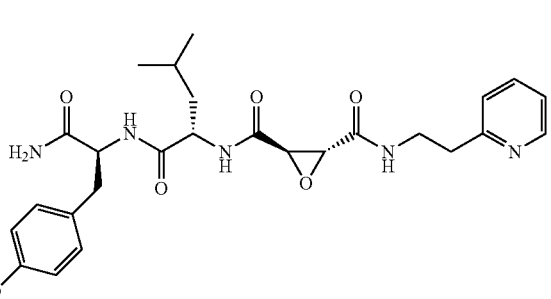

153
-continued
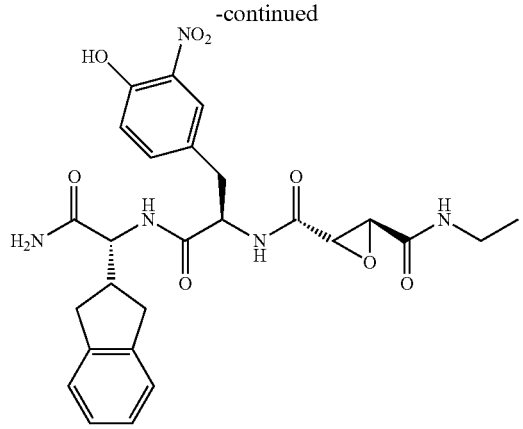
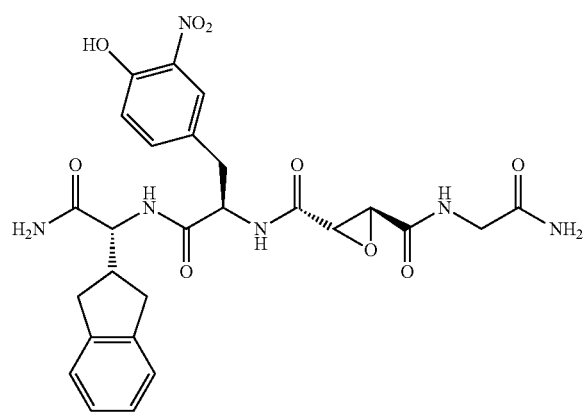
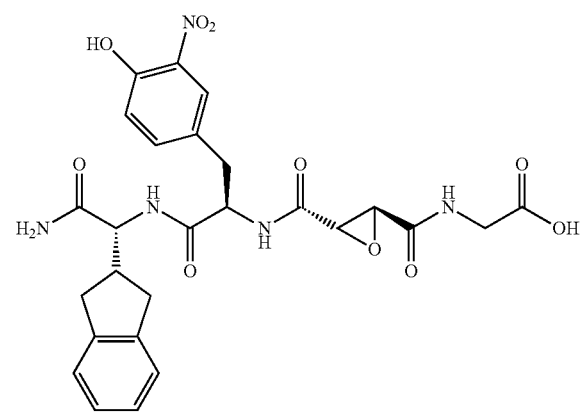
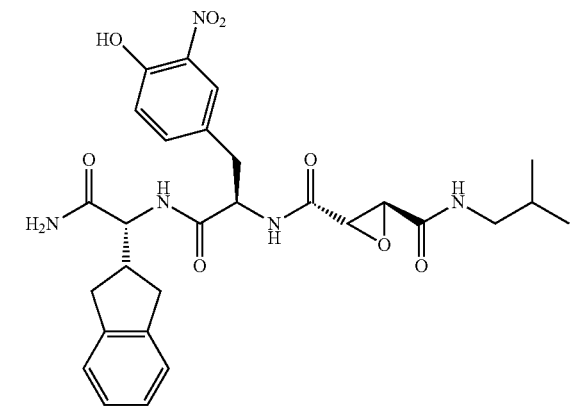
154
-continued
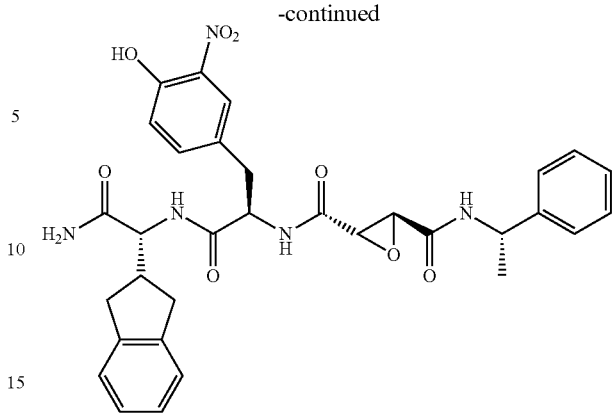
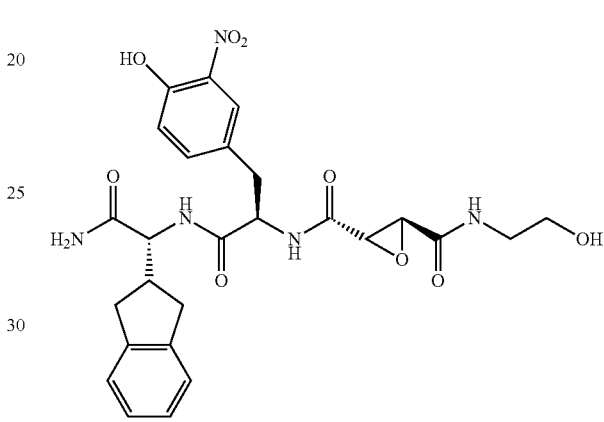
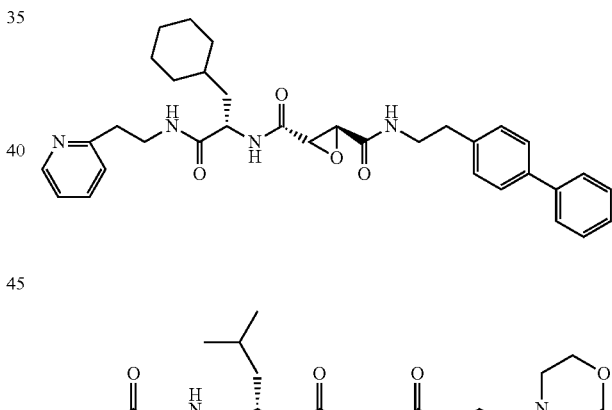
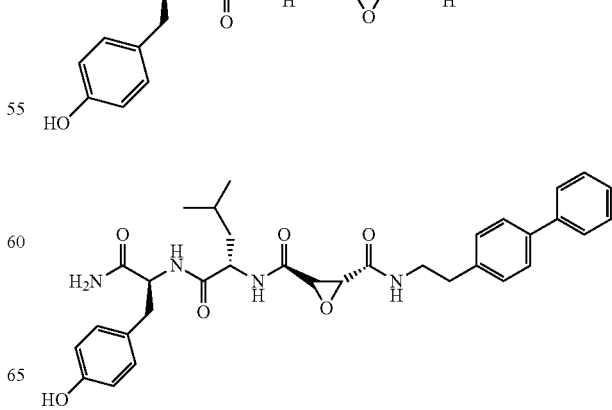

155
-continued
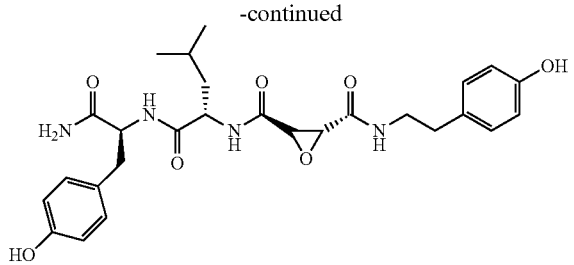
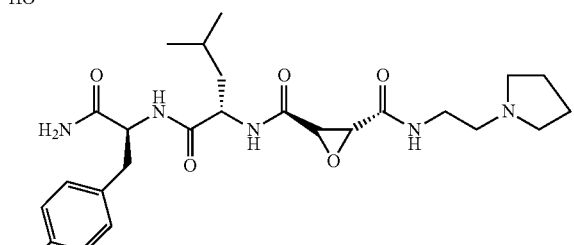
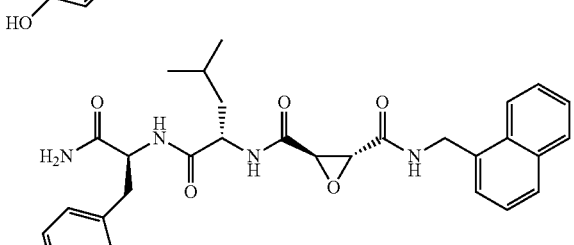
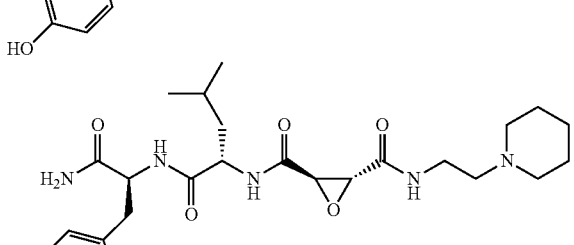
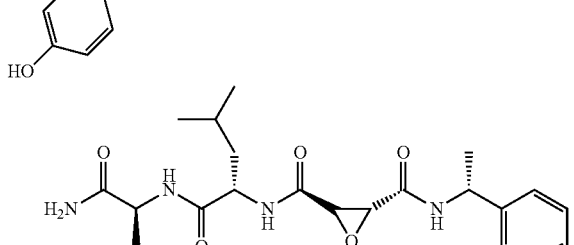
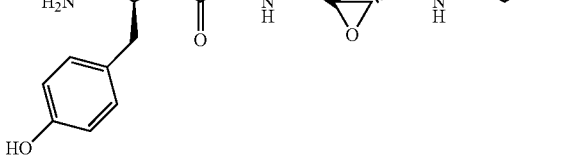
156
-continued
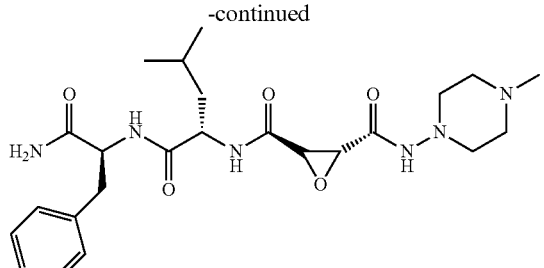
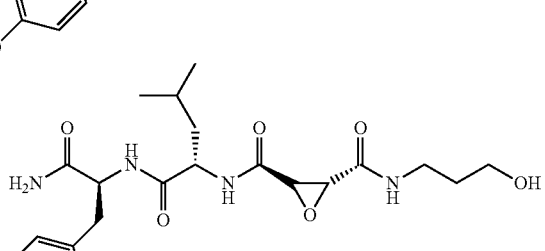
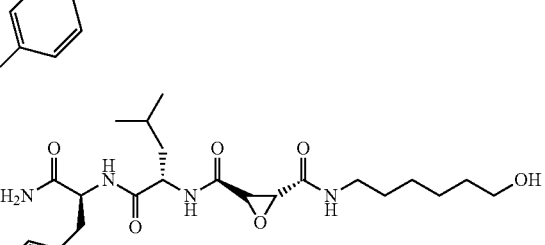
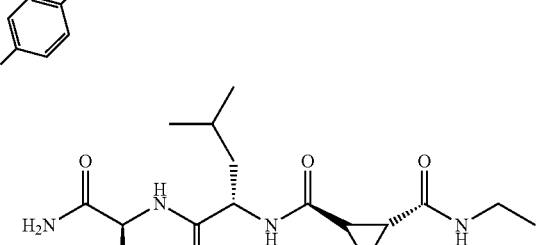
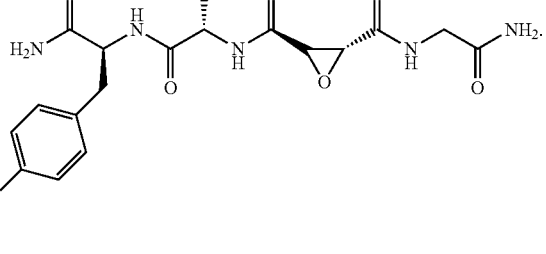
2. A pharmaceutical composition comprising a compound of claim 1 and a pharmaceutically acceptable carrier.
3. A packaged pharmaceutical comprising the pharmaceutical composition of claim 2 and instructions for using the composition.
\* \* \* \* \*